US008648605B2

(12) United States Patent
Nakamura et al.

(10) Patent No.: US 8,648,605 B2
(45) Date of Patent: Feb. 11, 2014

(54) SENSOR, SENSOR SYSTEM, PORTABLE SENSOR SYSTEM, METHOD OF ANALYZING METAL IONS, MOUNTING SUBSTRATE, METHOD OF ANALYZING PLATING PREVENTING CHEMICAL SPECIES, METHOD OF ANALYZING PRODUCED COMPOUND, AND METHOD OF ANALYZING MONOVALENT COPPER CHEMICAL SPECIES

(75) Inventors: Hidehiro Nakamura, Tsukuba (JP); Tooru Nakamura, Ibaraki (JP); Yutaka Hayashi, Ibaraki (JP); Yuji Kawanishi, Ibaraki (JP)

(73) Assignees: Hitachi Chemical Company, Ltd., Tokyo (JP); National Institute of Advanced Industrial Science and Technology, Tokyo (JP)

(*) Notice: Subject to any disclaimer, the term of this patent is extended or adjusted under 35 U.S.C. 154(b) by 783 days.

(21) Appl. No.: 12/680,447

(22) PCT Filed: Sep. 26, 2008

(86) PCT No.: PCT/JP2008/067384
§ 371 (c)(1),
(2), (4) Date: Mar. 26, 2010

(87) PCT Pub. No.: WO2009/041554
PCT Pub. Date: Apr. 2, 2009

(65) Prior Publication Data
US 2010/0253361 A1    Oct. 7, 2010

(30) Foreign Application Priority Data

Sep. 28, 2007 (JP) ............................... P2007-255997
Dec. 27, 2007 (JP) ............................... P2007-337684

(51) Int. Cl.
*G01N 27/62* (2006.01)
(52) U.S. Cl.
USPC ...................... 324/464; 324/444; 204/403.01

(58) Field of Classification Search
USPC ............................... 324/444, 464; 204/403.01
See application file for complete search history.

(56) References Cited

U.S. PATENT DOCUMENTS 4,963,245 A * 10/1990 Weetall ........................... 506/9
5,273,640 A * 12/1993 Kusanagi et al. ............. 204/401

(Continued)

FOREIGN PATENT DOCUMENTS

JP    3-505785    12/1991
JP    10-325821   12/1998

(Continued)

OTHER PUBLICATIONS

Presentation of Publications and the like by a third party dated Apr. 25, 2012 (notified to Applicants on May 15, 2012), for JP Application No. 2009-534393.
Japanese Official Action issued on Jan. 17, 2012, for JP Application No. 2009-534393.
Japanese Official Action dated Feb. 5, 2013, for JP Application No. 2009-534393.

(Continued)

*Primary Examiner* — Arleen M Vazquez
(74) *Attorney, Agent, or Firm* — Antonelli, Terry, Stout & Kraus, LLP.

(57) ABSTRACT

This invention provides a sensor having such a structure that the area in which a sensor electrode comes into contact with a liquid, a mist or a gas containing an analyte has been previously specified. The sensor comprises at least an electroconductive first electrode, an electroconductive second electrode, electroconductive first and second wirings connected to the first and second electrodes, and an insulating part for insulating the first and second wirings from each other and from a liquid, a mist or a gas containing the analyte. The insulating part is formed of an organic material. In the first and second electrodes, at least the surface, which comes into contact with a liquid, a mist or a gas containing the analyte, is formed of a material which is insoluble in a liquid or a mist containing the analyte, or is not attacked by a gas containing the analyte.

37 Claims, 37 Drawing Sheets

(56) References Cited

U.S. PATENT DOCUMENTS

| | | |
|---|---|---|
| 6,959,618 B1 * | 11/2005 | Larsen .................. 73/865.5 |
| 2002/0072084 A1 | 6/2002 | Meserol et al. |
| 2006/0162956 A1 | 7/2006 | Nakamura et al. |
| 2008/0010819 A1 | 1/2008 | Nakamura et al. |
| 2008/0289868 A1 | 11/2008 | Nakamura et al. |

FOREIGN PATENT DOCUMENTS

| | | |
|---|---|---|
| JP | 11-248669 | 9/1999 |
| JP | 2003-227811 | 8/2003 |
| JP | 2004-518965 | 6/2004 |
| JP | 2006-58020 | 3/2006 |
| JP | 2007-147643 | 6/2007 |
| WO | WO 02/065087 | 8/2002 |
| WO | WO 03/056889 A1 | 7/2003 |
| WO | WO 2007/049607 A1 | 5/2007 |

OTHER PUBLICATIONS

Transmittal of International Preliminary Report on Patentability dated May 14, 2010, for Application No. PCT/JP2008/067384.

H. Ohira, et al., "Proposal of Printed Circuit Board by New Manufacturing Process (B2it)", $9^{th}$ Proceedings of JIEP (Japan Institute of Electronics Packaging) Annual Meeting, ISSN0915-0043, 15A-10, pp. 55 and 56 (Mar. 1995).

T. Mori, et al., "Application and Miniaturization of Substrate by Interlayer Connection Technique Using Bump", $10^{th}$ Proceedings of JIEP Annual Meeting, ISSN0915-0043, 15A-09, pp. 79 and 80 (Mar. 1996).

"Introduction of Research Results in Technology Techno Report (2002)", Osaka Municipal Technical Research Institute, Published Jul. 2003, p. 14.

Communication mailed Jun. 4 2013, in connection with Taiwanese Patent Application No. 097137207, 5 pages; Taiwan Patent Office, Taiwan.

* cited by examiner

FIG. 18
(A)
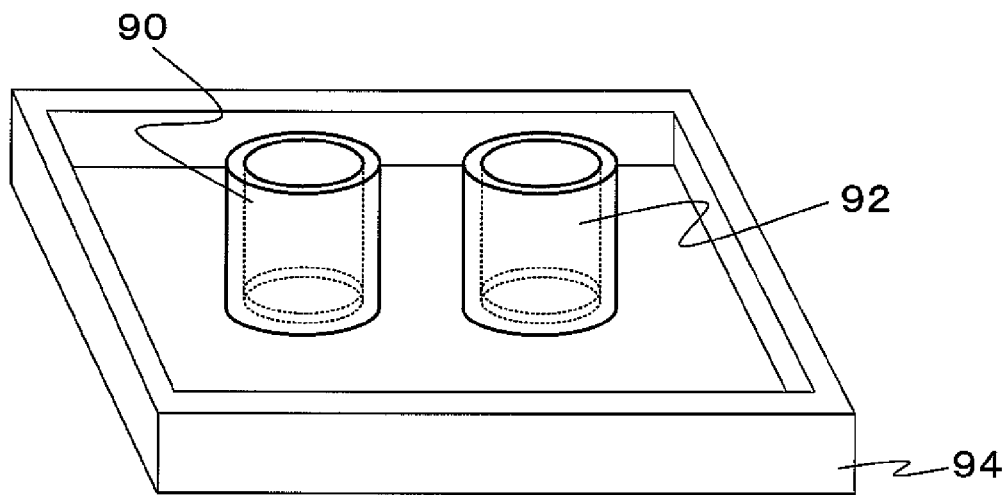
(B)
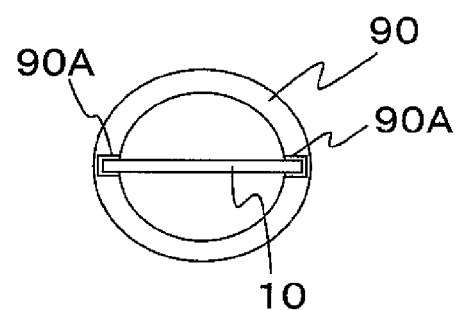

SENSOR, SENSOR SYSTEM, PORTABLE SENSOR SYSTEM, METHOD OF ANALYZING METAL IONS, MOUNTING SUBSTRATE, METHOD OF ANALYZING PLATING PREVENTING CHEMICAL SPECIES, METHOD OF ANALYZING PRODUCED COMPOUND, AND METHOD OF ANALYZING MONOVALENT COPPER CHEMICAL SPECIES

TECHNICAL FIELD

The present invention relates to a metal ion sensor that is used to analyze metal ions, a sensor system, a portable sensor system, and a method of analyzing metal ions, and more particularly, to a metal ion sensor structure, a sensor system, a method of analyzing a chemical species, and a mounting substrate.

BACKGROUND ART

In recent years, the earth's environment has greatly affected by manufacture, a consuming society, and business activity. The influence is incomputable. For example, air pollution, water pollution, and soil pollution due to wastes cause the deterioration of an ecosystem by a food chain and global warming. Therefore, CSR, environment, business, and laws and regulations that are inseparable from the business activity have become important. For this reason, it becomes to be important to develop a technique capable of contributing to the improvement and conservation of the environment. For example, the importance of the analysis of metal ions, such as copper ions, cadmium ions, lead ions, chrome ions, and mercury ions, which are important in a manufacturing field and an environmental field has increased. From this point of view, a "surface potential measurement-type sensor device" has been proposed as an analysis technique (for example, see Patent Document 1). This technique uses the analysis function of a self-assembled film. The analysis principle is as follows: when ion atoms are attracted to a self-assembled film provided at the leading end of an electrode, a work function varies from a position corresponding to the Fermi level of a base before and after the ion atoms are attracted, and the variation in potential is measured based on a reference electrode to analyze the concentration of a very small amount of solution. It is considered that this technique has the following effects:

1) The potential variation reaches a specific potential corresponding to the attracted ions (it is possible to selectively perform analysis corresponding to a molecular film structure);

2) The specific potential does not depend on the area of the electrode (since a current is not measured, a measurement system is simple and there is a strong possibility that the size of the system will be reduced);

3) The time required for the potential to reach the specific potential is proportional to the area of the electrode (it is possible to perform analysis in a wide range); and 4) It is possible to repeatedly perform analysis a maximum of twenty times by EDTA cleaning.

The inventors has pursued analysis using an electrochemical analysis method in which the self-assembled film is not provided on the electrode, according to an analysis target. However, the inventors found that this method had the following problems, similar to the self-assembled sensor.

When this technique is applied to a complex system sample (hereinafter, simply referred to as a "complex system") in which a material included in an analyte is not known or the concentration of the material is not known even though the kind of material is known, a technique for more selectively analyzing the material is needed. Therefore, it is indispensable to increase the number of electrodes for analyzing a multi-component system, and a multi-layer wiring technique capable of reducing the size of a system even when the number of measuring electrodes is increased is more advantageous than a technique for forming a single-layer wiring substrate. That is, an effectively manufacturing technique capable of corresponding to the multi-layer wiring technique as well as the single-layer wiring substrate is required for the measuring substrate. In recent years, an inorganic substrate, such as a glass, ceramic, or mica substrate, has been used as an electrochemical measuring substrate, and a vacuum process, such as sputtering or vapor deposition, has been performed to form wiring lines. This process is effective in miniaturizing the wiring line, but it is difficult to reduce manufacturing costs and form a multi-layer structure.

An example in which an organic substrate used in the printed circuit board industry is used as the measuring substrate has not been known.

As the main multi-layer wiring technique generally known in the printed circuit board industry, there is a through hole connection technique which is a combination of drilling and a plating process, which has generally been known. However, in the technique, since holes are formed in all layers, there is a limit in the accommodation of wiring lines. In order to reduce the volume of holes provided in a connection portion, a build-up technique has generally been used which repeatedly performs the formation of an insulating resin composition layer, boring, and the formation of a circuit. The build-up technique is mainly divided into a laser method and a photolithography method. The laser method radiates a laser beam to form holes in the insulating resin composition layer. The photolithography method uses a photosensitive hardener (photoinitiator) for the insulating resin composition layer, puts a photomask on the insulating resin composition layer, and performs exposure and development to form holes. In addition, in order to further reduce manufacturing costs and increase density, some interlayer connection methods have been proposed. Among them, a method capable of omitting boring and a conductive layer plating process has drawn attention. In the method, first, a conductive paste is printed on wiring lines on a substrate to form a bump, an interlayer connection insulating material and a metal layer in a B stage are arranged, and the bump is inserted into a molding resin by a press to be electrically connected to a metal layer. The method of inserting the bump has been published in the scientific society or the newspaper, and has widely been known in the printed circuit board industry (for example, see Non-Patent Documents 1 and 2).

There is a collectively laminating method as a more efficient forming method. A wiring plate has been proposed which is integrally formed by printing holes, a connection conductor, and wiring lines on a ceramic body, which is called a green sheet before sintering, aligning them, and applying heat and pressure. However, since the plate is shrunken by about 20%, numerical stability is low. In addition, since the plate is made of an inorganic material, it is expensive. As a collectively laminating method that uses an organic material and does not require a boring process, there is a collectively laminated substrate conceived by the inventors including Nakamura (for example, see Patent Document 2). This method uses an insulating substrate made of a thermoplastic liquid crystal polymer.

In the method of forming a multi-layer structure, for example, plating, etching, printed wiring, and a wiring transfer method have been used to form a fine wiring line.

In the analysis of a complex system, it is very difficult to directly contact a sensor with a liquid to be extracted and analyzed and selectively analyze target metal ions. Even when a component system has been known, other metal ions preventing analysis or an analysis preventing material is included in the target metal ions when the concentration of the metal ions is selectively analyzed, which significantly reduces the possibility of analysis. The analysis of a monovalent copper chemical species is given as an example. In this case, the monovalent copper chemical species is a simple monovalent copper ion, a monovalent copper ion complex, or a composite chemical species including monovalent copper.

For example, the analysis of the monovalent copper chemical species is used to identify protein and sugar.

In addition, in an electrochemical measuring method in a filled via copper plating solution that covers a structure portion having a hole with the bottom with copper and forms a flat wiring layer, the measurement of the potential of a constant current at a cathode is used to evaluate a filled via property. However, it is difficult to qualitatively and/or quantitatively analyze a monovalent copper chemical species even though there is a plurality of metal ions or an analysis preventing material and the principle of a measurement method thereof is considered.

For the filled via copper plating solution, the monovalent copper ion deteriorates the filled via property a little, and it is preferable to qualitatively and quantitatively analyze the filled via copper plating solution. However, it is not certain that the plating preventing chemical species deteriorating the filled via property is the monovalent copper ion, the monovalent copper ion complex, the composite chemical species including monovalent copper, or a produced compound included in the plating solution that is used. When there is a large amount of divalent copper or an analysis preventing material, it is difficult to qualitatively and quantitatively analyze a target plating preventing chemical species and a produced compound selectively.

In the invention, the electrochemical analysis method means a method which immerses a plurality of electrodes in a liquid to be analyzed, applies a voltage or a current between the electrodes, and observes a variation in the current or the voltage. In the method, a plurality of strip-shaped gold thin films that are adhered on a glass substrate and extend in one direction substantially in parallel to each other are used as the electrodes.

Since the electrode is connected to a measuring device, a portion of the electrode needs to protrude from the liquid to be analyzed to the outside. The contact area of the electrode with the liquid to be analyzed is changed by, for example, the depth of immersion and the inclination of the substrate during immersion. In this case, the reproducibility of the analysis result is not ensured. In particular, there is a problem in the reproducibility of quantitative analysis. Therefore, it is important to insulate a wiring line from, for example, a liquid, mist, or gas, which is an analysis target, separate the electrode from the wiring line, and ensure a predetermined area of the electrode. It is important to provide an insulating portion on the wiring line, but it is difficult to effectively form the layer on a glass substrate at a low cost.

It is difficult to repeatedly use the electrode for a long time since it is contaminated, modified, and plated in the analysis process, and the electrode is regarded as an article of consumption. Therefore, in order to frequently use an inorganic substrate, such as a glass substrate, having electrodes formed thereon for field water quality analysis for managing chemicals and a work environment in the manufacturing line, it is preferable that the substrate be manufactured at a low cost.

The inventors have conducted an examination on the application of an organic substrate to electrochemical measurement and surface potential. As a result of the examination, the organic substrate has two main problems. The first problem is chemical resistance. When a liquid to be extracted and analyzed is a strong acid or a strong alkali, ions or molecules that prevent or increase an analysis function are likely to be generated from the organic substrate during analysis. In addition, the decomposition of an organic material forming the organic substrate, the remaining solvent, various kinds of additives, an ion material attracted during a wiring process, and a material absorbed from the air cause the generation of the analysis preventing ions or molecules.

The second problem is heat resistance. This is because it is necessary to form a carbon layer, which is an inert layer, such as a gold or platinum layer, on the electrode in the electrochemical analysis. (It is preferable that the carbon layer be formed of 100% of carbon. However, when an additive, such as a binder or a dispersant, is used in the component, impurities are removed such that the purity of the additive is approximately 100%. Hereinafter, a layer that includes carbon as a component and serves as an inert layer is referred to as a carbon including layer, and a material is referred to as a carbon including material. In addition, coating with the carbon including layer is referred to as carbon coating. The shape of carbon may be a particle or a carbon filament). For example, in general, a DLC method has been used to form the carbon including layer in which the content of carbon is approximately 100%, in terms of characteristics thereof, and a base material is exposed to a high temperature of 200° C. or more. In high-accuracy analysis, in a vapor deposition process and/or a sputtering process, the precipitation of impurities that are decomposed and generated prevents analysis. Therefore, an organic resin having high chemical resistance and high heat resistance, such as polyimide or liquid crystal polymer, in the method of forming a multi-layer wiring substrate is considered as an insulating material for a substrate for a sensor. However, this material is not necessarily selected, but there is a difficulty in a reduction in cost and the degree of recognition or spread in the industry. In particular, it is considered that the decomposition of an organic material at the adhesion interface or the bonding interface between an insulating material and a buried electrode causes the most serious problem. In this case, a liquid to be extracted and analyzed is infiltrated into the interface, which results in a variation in the area of the electrode during measurement or when the electrode is repeatedly used.

In the analysis of a complex system, that is, in high-accuracy analyze, a pre-process is needed. In many case, a complicated pre-process is needed. For example, an organic ligand, a filtering method, and a calorimetric method using absorbance measurement are performed to analyze monovalent copper (for example, see Non-Patent Document 3). This analysis method is relatively simple and has high selectivity. However, in order to put this analysis method to practical use, it is necessary to reduce the time required for a pre-process or analysis.

Patent Document 1: Japanese Patent Application Laid-Open (JP-A) No. 2006-058020

Patent Document 2: WO/2003/056889

Non-Patent Document 1: Hiroshi Ohira, other two persons: Proposal of Printed Circuit Board by New Manufacturing Process (B2it), 9th Proceedings of JIEP (Japan Institute of Electronics Packaging) Annual Meeting, ISSN0916-0043, 15A-10, PP. 55-56, (March, 1995)

Non-Patent Document 2: Takahiro Mori, other five persons: Application and Miniaturization of Substrate by Interlayer Connection Technique Using Bump, 10th Proceedings of JIEP Annual Meeting, ISSN0916-0043, 15A-09, PP. 79-80, (March, 1996)

Non-Patent Document 3: "Introduction of Research Results in Technology Techno Report (2002)", Osaka Municipal Technical Research Institute, Published July, 2003, p. 14 (URL:http://www.omtri.city.osaka.jp/)

DISCLOSURE OF THE INVENTION

Problem to be Solved by the Invention

The present invention has been made in view of the problems according to the related art, and the problem of the invention is to achieve the following objects.

That is, an object of the invention is to provide a sensor having a structure that defines the contact area of an electrode of the sensor with a liquid, mist, or gas including an analyte in advance.

In order to define the area of the electrode, the invention provides a sensor having a structure which includes a wiring line that is electrically connected to the electrode of the sensor and prevents the elution of a wiring material from the wiring line to a liquid or mist including an analyte, the leakage or discharge of current from the wiring line to the liquid, mist, or gas including the analyte, and the electrical interference between a plurality of wiring lines.

An object of the invention is to provide a sensor having an electrode structure in which a material forming an insulating substrate for a sensor does not need to have chemical resistance and heat resistance as high as an inorganic insulating material such as glass or ceramics. Another object of the invention is to provide a sensor having an electrode structure that does not require an alignment process and a masking process for ensuring insulating property between electrodes, in order to form a carbon including layer forming the electrode structure according to the invention so as to be separated between the electrodes, if necessary.

A still another object of the invention is to provide an analysis method capable of qualitatively and quantitatively analyzing a monovalent copper chemical species, and a plating preventing chemical species or a produced compound included in copper plating solution that is used, using an electrochemical method, a surface potential measuring method, a colorimetric method, or combinations thereof.

A yet another object of the invention is to provide an analysis method that qualitatively and quantitatively analyzes a monovalent copper chemical species from a plurality of metal ions or a liquid of a complex system including an analysis preventing material, or qualitatively and quantitatively analyzes a plating preventing chemical species or a chemical species of a produced compound included in a plating solution including an analysis preventing material or a large amount of bivalent copper by selectively performing an electrochemical method and a surface potential measuring method, using the sensor according to the invention or other types of sensors.

A still yet another object of the invention is to provide a sensor system that includes the sensor and is capable of integrally and continuously performing a pre-process with high efficiency.

A still yet another object of the invention is to provide a portable sensor system that includes the sensor and can be carried to a desired place and easily analyze a very small amount of an analyte in a short time on the spot.

Means for Solving the Problem

In the invention, as a means for preventing the elution of a wiring material from the connection wiring line that is electrically connected to the electrode of the sensor to a liquid or mist including an analyte, the leakage or discharge of current from the connection wiring line to the liquid, mist, or gas including the analyte, and the electrical interference between a plurality of connection wiring lines, an insulating portion that is made of an organic material and insulates connection wiring lines electrically connected to a plurality of electrodes and insulates the connection wiring lines from the liquid, mist, or gas including the analyte is provided.

In the invention, as a means for defining the contact area of the electrode of the sensor with the liquid, mist, or gas including the analyte in advance, a coverlay that has openings through which the plurality of electrodes provided on an organic insulating substrate are exposed to the outside and covers the connection wiring lines is provided.

The coverlay is a protectively layer and protects wiring lines drawn through portions other than the exposed portions and electrodes that are not exposed. The protective layer prevents a mechanical damage and ensures insulating property between the electrodes and between the connection wiring lines. The protective layer can prevent a leakage current between the wiring lines due to humidity and a short circuit due to the residue of solder cream print during the mounting of electronic parts. For example, an insulating film with an adhesive layer, a resist ink, or a resist film is used as the coverlay.

The material forming the insulating substrate used in the sensor according to the invention is not limited to an organic material with heat resistance that can correspond to a vacuum process. In addition, in order to select a manufacturing process from a multi-layer forming process including many organic materials that cannot correspond to the vacuum process, the inventors uses a means that provides a carbon including layer on an insulating substrate made of an organic material using a method of forming the carbon including layer in which the organic material forming the insulating substrate does not need to have particularly high heat resistance and high chemical resistance.

For this reason, a low-temperature vapor deposition method is needed. As a low-temperature carbon vapor deposition, a carbon vapor deposition method called tough carbon using an ion cluster beam has been known (for example, see Japanese Patent No. 3660866). In this method, since vapor deposition is performed at a low temperature of 100° C., it is possible to significantly reduce the mixture of impurities from a base material or contamination (hereinafter, simply referred to as "contamination"). Therefore, a glass epoxy resin may be used as a candidate of the organic base material.

In addition, a method using print paste is effective. As the print paste, the technique and paste disclosed in Japanese Patent Application Laid-Open (JP-A) No. 2006-147202, 2007-165708, or 2007-165709 may be used. Specifically, carbon paste manufactured by HITACHI CHEMICAL CO., LTD is preferably used. As a method of printing the carbon paste, an application method using a syringe or an ink jet method is effective. The hardening temperature is in the range of 160° C. to 210° C., and may be appropriately set according to the heat resistance of a base material.

That is, for example, in order to improve mechanical and thermal characteristics, a mixture of an organic material and an inorganic material may be used, which is also included in the scope of the invention.

In the electrochemical measurement and the potential measurement, it is important to ensure an insulating property in addition to chemical resistance and heat resistance. In particular, the stability of the insulating property is very important to high resolution of measured data or the reproducibility of measured data.

However, in any method, when a base material is selected and a carbon including layer is formed on the entire surface of the base material by various vapor deposition methods and various printing methods, it is necessary to prepare a separate mask in order to ensure insulating property between the electrodes, and an alignment is needed. Therefore, there is a difficulty in achieving an effective manufacturing method capable of corresponding to minute electrodes. The invention provides means for solving the problems.

In the invention, as an analysis means that selectively performs the identification and the quantitative analysis of a monovalent copper chemical species from a plurality of metal ions or a liquid of a complex system including an analysis preventing material, a plating preventing chemical species, or a chemical species of a produced compound included in a plating solution, which is being used, including an analysis preventing material or a large amount of bivalent copper, a method includes contacting a liquid of a complex system or a copper plating solution used for copper plating with at least a first electrode and a second electrode, applying a voltage whose level varies over time between the first and second electrodes, identifying a monovalent copper chemical species, a plating preventing chemical species, or a chemical species of a produced compound in the voltage range in which the maximum value of the current flowing between the first and second electrodes, and analyzing the concentration of the monovalent copper chemical species, the plating preventing chemical species, or the chemical species of the produced compound based on the maximum value of the current within the voltage range or the integral value of the current with respect to the voltage.

That is, the characteristics of the invention are as follows.

(1) A sensor includes: first and second conductive electrodes; first and second conductive wiring lines that are respectively connected to the first and second conductive electrodes; and an insulating portion that insulates the first wiring line from the second wiring line and insulates the first and second wiring lines from a liquid, mist, or gas including an analyte. The insulating portion is made of an organic material, and at least the surfaces of portions of the first and second electrodes that come into contact with the liquid, the mist, or the gas including the analyte are made of a material that is insoluble by the liquid or the mist including the analyte or a material that is not eroded by the gas including the analyte.

(2) The sensor according to (1) may further include: a third electrode that supplies at least a portion of the potential thereof to the first electrode or the second electrode at the same polarity or different polarities; and a third wiring line that is connected to the third electrode. At least the surface of a portion of the third electrode that comes into contact with the liquid, the mist, or the gas including the analyte is made of a material that is insoluble by the liquid, the mist, or the gas including the analyte or a material that is not eroded by the gas including the analyte.

Gold, platinum, or carbon is given as an example of the material that is insoluble in the liquid or the mist including the analyte and is not eroded by the gas including the analyte.

(3) The sensor according to (2) may further include an insulating portion that is made of an organic material and insulates the third wiring line from the first and second wiring lines, and the liquid, the mist, or the gas including the analyte.

(4) In the sensor according to (1), the first and second wiring lines may be connected to corresponding connection terminals.

(5) In the sensor according to (2), the third wiring line may be connected to a connection terminal.

(6) In the sensor according to (I), a plurality of sets of the first electrode and the first wiring line and a plurality of sets of the second electrode and the second wiring line may be provided.

(7) In the sensor according to (2), a plurality of sets of the first electrode and the first wiring line, a plurality of sets of the second electrodes and the second wiring lines, and a plurality of sets of the third electrodes and the third wiring lines may be provided.

(8) The sensor according to (4) may further include: an insulating substrate that is made of an organic material; at least one electrode group that includes the first and second electrodes and is arranged on the insulating substrate; at least one connection wiring line group that is electrically connected to the electrode group and has at least one layer including the first and second wiring lines; and at least one connection terminal group that is electrically connected to the connection wiring line group.

(9) The sensor according to (5) may further include: an insulating substrate that is made of an organic material; at least one electrode group that includes the first and second electrodes and the third electrode and is arranged on the insulating substrate; at least one connection wiring line group that is electrically connected to the electrode group and has at least one layer including the first, second, and third wiring lines; and at least one connection terminal group that is electrically connected to the connection wiring line group.

(10) The sensor according to (8) or (9) may further include at least a coverlay that is provided on the insulating substrate, has openings through which the electrode group is exposed to the outside, and covers the connection wiring line group. At least the coverlay and the insulating substrate form the insulating portion that insulates the connection wiring line group and insulates the connection wiring line from the liquid, the mist, or the gas including the analyte.

(11) In the sensor according to (10), each of the openings of the coverlay may be provided so as to be arranged inside each electrode of the electrode group.

(12) In the sensor according to (10), each of the openings of the coverlay may be provided so as to be arranged outside each electrode of the electrode group that is exposed through the opening.

(13) The sensor according to (11) or (12) may further include at least a carbon including layer that is provided on the insulating substrate. The carbon including layer may be formed on the surface of the coverlay surface and at least a portion of the surface of each electrode disposed in the opening.

(14) In the sensor according to any one of (10) to (13), the opening of the coverlay may be formed such that the diameter thereof is increased from the upper surface to the lower surface.

(15) In the sensor according to any one of (10) to (13), the coverlay may be formed such that the area of the opening in the upper surface is less than the area of the opening in the lower surface.

(16) In the sensor according to any one of (10) to (13), the coverlay may include at least two layers, that is, a coverlay film and an adhesive layer. The edge of an opening in the adhesive layer and the edge of an opening of the coverlay film may be arranged at the same position, or the edge of the opening in the adhesive layer may be arranged outside the edge of the opening of the coverlay film.

(17) In the sensor according to any one of (1) to (16), gold may be coated on at least a portion of the outermost surface of at least one of the first to third electrodes.

(18) In the sensor according to (17), any one of a carbon including layer, a nickel layer, and a palladium layer may be provided as a base layer of the outermost layer.

(19) In the sensor according to any one of (1) to (18), an organic monolayer may be formed on at least a portion of the outermost surface of at least one of the first to third electrodes.

(20) In the sensor according to (19), the organic monolayer may have a substituent group including at least one selected from the group consisting of chlorine, bromine, sulfur, nitrogen, and oxygen on the surface thereof.

(21) A sensor system includes: the sensor according to (4) or (5), or any one of (8) to (20); and a measuring device that measures voltage-current characteristics between at least two electrodes among the electrodes of the sensor.

(22) The sensor system according to (21) may further include a connector and a wiring member that electrically connect the sensor and the measuring device.

(23) The sensor system according to (21) or (22) may further include an analysis liquid container.

(24) The sensor system according to any one of (21) to (23) may further include: a blocking plate that is provided between the connector and the electrode or the electrode group which comes into contact with a liquid or mist including the analyte and prevents the evaporation of a liquid including the analyte from the liquid level.

(25) In the sensor system according to any one of (21) to (23), the distance from the connector to the electrode or the electrode group may be 3 mm or more.

(26) A portable sensor system includes: the sensor according to (4) or (5), or any one of (8) to (20); a measuring device that measures voltage-current characteristics between at least two electrodes among the electrodes of the sensor; and a portable container that accommodates at least the sensor and the measuring device.

(27) The portable sensor system according to (26) may further include a connector and wiring lines that are accommodated in the portable container and electrically connect the sensor and the measuring device.

(28) In the sensor according to (1) or (2), at least one of a set of the first electrode and the first wiring line, a set of the second electrode and the second wiring line, and a set of the third electrode and the third wiring line may include one conductive line and an organic material serving as the insulating portion which covers a portion of the conductive line, and a portion of the conductive line exposed from the organic material may be used as the electrode.

(29) In the sensor according to (28), the exposed portion may be a cut surface of the conductive line which is covered with the organic material.

(30) In the sensor according to (28), the conductive line may have another portion that is exposed from the organic material and is separated from the portion exposed from the organic material, and another exposed portion of the conductive line may be used as the connection terminal.

(31) A sensor includes: an insulating substrate; an electrode group that includes a reference electrode, a counter electrode, and a working electrode arranged on the same surface of the insulating substrate; a connection wiring line group that includes one or more layers and is electrically connected to the electrode group; and a measuring terminal group that is electrically connected to the connection wiring line group.

(32) In the sensor according to (31), the reference electrode may be arranged between the counter electrode and the working electrode.

(33) In the sensor according to (31) or (32), the outermost surface of the reference electrode is covered with a carbon including layer.

(34) The sensor according to any one of (31) to (33) may further include: a coverlay that is provided on the insulating substrate and has openings through which the electrodes of the electrode group are exposed to the outside; and a carbon including layer. The carbon including layer may be formed on the surface of the coverlay surface and at least the surface of the electrode disposed in the opening.

(35) In the sensor according to (34), each opening of the coverlay may be formed such that the area thereof is more than that of each electrode exposed through the opening.

(36) In the sensor according to (34) or (35), the opening of the coverlay may be formed such that the diameter thereof is increased from an upper surface to a lower surface.

(37) In the sensor according to any one of (34) to (36), the coverlay may be made of a single material, and the coverlay may be formed such that the area of the opening in the upper surface is less than the area of the opening in the lower surface.

(38) In the sensor according to (34) or (35), the coverlay may include at least two layers, that is, a coverlay film and an adhesive layer. The edge of an opening in the adhesive layer and the edge of an opening of the coverlay film may be arranged at the same position, or the edge of the opening in the adhesive layer may be arranged outside the edge of the opening of the coverlay film.

(39) In the sensor according to any one of (31) to (35), gold may be coated on at least a portion of the outermost surface of the working electrode and/or the counter electrode.

(40) In the sensor according to (39), any one of a carbon including layer, a nickel layer, and a palladium layer may be provided as a base layer of the outermost layer.

(41) In the sensor according to any one of (34) to (40), an organic monolayer may be formed on at least a portion of the outermost surface of the working electrode and/or the counter electrode.

(42) In the sensor according to (41), the organic monolayer may have a substituent group including at least one selected from the group consisting of chlorine, bromine, sulfur, nitrogen, and oxygen on the surface thereof.

(43) In the sensor according to any one of (34) to (42), the insulating substrate may be made of an organic material.

(44) A sensor system includes: the sensor according to any one of (34) to (43); and a measuring device that measures voltage-current characteristics between at least two electrodes among the electrodes of the sensor.

(45) The sensor system according to (44) may further include a connector and a wiring member that electrically connect the sensor and the measuring device.

(46) The sensor system according to (45) may further include: an analysis liquid container; and a pre-processing unit that neutralizes or filters a liquid to be analyzed, or makes the liquid to be analyzed hardly soluble.

(47) A portable sensor system includes: the sensor according to any one of (35) to (44); a measuring device that measures voltage-current characteristics between two electrodes among the electrodes of the sensor; and a portable container that accommodates at least the sensor and the measuring device.

(48) The portable sensor system according to (47) may further include a connector and wiring lines that are accommodated in the portable container and electrically connect the sensor and the measuring device.

(49) A method of analyzing metal ions directly analyzes a liquid to be analyzed using the sensor system according to any one of (44) to (46), without performing a pre-process.

(50) A method of analyzing metal ions directly analyzes a liquid to be analyzed using the sensor system according to (46), with performing a pre-process.

(51) In the method of analyzing metal ions according to (50), the liquid to be analyzed may be analyzed by a colorimetric method after neutralization and filtering.

(52) In a method of analyzing metal ions using the sensor system according to (46), the liquid to be analyzed may be analyzed by an electrochemical method after neutralization and filtering.

(53) In the method of analyzing metal ions using the sensor system according to (46), the liquid to be analyzed may be analyzed by an electrochemical method after being neutralized, made hardly soluble, and filtered.

(54) A mounting substrate includes: an insulating substrate; an electrode group that is provided on the insulating substrate; a coverlay that has openings through which the electrode group is exposed to the outside; and a carbon including layer. The carbon including layer is disposed on the surface of the coverlay and in the openings, and the carbon including layer on the surface of the coverlay is separated from at least one electrode of the electrode group at the edge of the opening.

(55) In the mounting substrate according to (54), the opening of the coverlay may be formed such that the diameter thereof is increased from an upper surface to a lower surface.

(56) In the mounting substrate according to (54), the coverlay may be made of a single material, and the coverlay may be formed such that the area of the opening in the upper surface is less than the area of the opening in the lower surface.

(57) In the mounting substrate according to (54), the coverlay may include at least two layers, that is, a coverlay film and an adhesive layer. The edge of an opening in the adhesive layer and the edge of an opening of the coverlay film may be arranged at the same position, or the edge of the opening in the adhesive layer may be arranged outside the edge of the opening of the coverlay film.

(58) A method of analyzing a plating preventing chemical species includes: contacting a copper plating solution that is used for copper plating with at least a first electrode and a second electrode; applying a voltage whose level varies over time between the first and second electrodes; identifying the plating preventing chemical species in a voltage range in which a variation in a current flowing between the first and second electrodes is observed; and analyzing the concentration of the plating preventing chemical species based on the maximum value of the current or the integral value of the current with respect to the voltage.

(59) A method of analyzing a compound produced from a copper plating solution during copper plating includes: contacting the copper plating solution that is used for the copper plating with at least a first electrode and a second electrode; applying a voltage whose level varies over time between the first and second electrodes; identifying the compound produced from the copper plating solution during the copper plating in a voltage range in which a variation in a current flowing between the first and second electrodes is observed; and analyzing the concentration of the compound produced from the copper plating solution during the copper plating based on the maximum value of the current or the integral value of the current with respect to the voltage.

(60) The method of analyzing a plating preventing chemical species according to (58) may further include: providing a third electrode that supplies at least a portion of the potential thereof to the first electrode or the second electrode at the same polarity or different polarities; and contacting the copper plating solution with the third electrode.

(61) The method of analyzing a compound produced from a copper plating solution during copper plating according to (59) may further include: providing a third electrode that supplies at least a portion of the potential thereof to the first electrode or the second electrode at the same polarity or different polarities; and contacting the copper plating solution with the third electrode.

(62) In the method of analyzing a plating preventing chemical species according to (58) or (60), the voltage range may be from +0.2 V to +2.0 V.

(63) In the method of analyzing a produced compound according to (59) or (61), the voltage range may be from +0.2 V to +2.0 V.

(64) In the method of analyzing a plating preventing chemical species according to (58) or (60), the concentration of the plating preventing chemical species may be analyzed based on a value obtained by subtracting the maximum value of the current or the integral value of the current with respect to the voltage, which is obtained from an initial make-up bath copper plating solution before being used, instead of the copper plating solution that is being used, from the maximum value of the current or the integral value of the current with respect to the voltage, which is obtained from the copper plating solution that is used for the copper plating.

(65) In the method of analyzing a produced compound according to (59) or (61), the concentration of the produced compound may be analyzed based on a value obtained by subtracting the maximum value of the current or the integral value of the current with respect to the voltage, which is obtained from an initial make-up bath copper plating solution before being used, instead of the copper plating solution that is being used, from the maximum value of the current or the integral value of the current with respect to the voltage, which is obtained from the copper plating solution that is used for the copper plating.

(66) In the method of analyzing a plating preventing chemical species according to (64), the temperature difference between the initial make-up bath copper plating solution and the copper plating solution that is being used may be within 10° C.

(67) In the method of analyzing a produced compound according to (65), the temperature difference between the initial make-up bath copper plating solution and the copper plating solution that is being used may be within 10° C.

(68) In the method of analyzing a plating preventing chemical species according to (64), the temperature of the initial make-up bath copper plating solution and the temperature of the copper plating solution that is being used may be measured. The rate of change of the maximum value of the current or the integral value of the current with respect to the voltage of the initial make-up bath copper plating solution, which is separately analyzed, according to the temperature may be used to covert the maximum value of the current or the integral value of the current with respect to the voltage of the analyzed initial make-up bath copper plating solution into a value corresponding to the temperature of the copper plating solution that is being used. The concentration of the plating preventing chemical species may be analyzed based on a value obtained by subtracting the converted value from the maximum value of the current or the integral value of the current with respect to the voltage of the copper plating solution used for copper plating.

(69) In the method of analyzing a produced compound according to (65), the temperature of the initial make-up bath copper plating solution and the temperature of the copper plating solution that is being used may be measured. the rate of change of the maximum value of the current or the integral value of the current with respect to the voltage of the initial make-up bath copper plating solution, which is separately analyzed, according to the temperature may be used to covert the maximum value of the current or the integral value of the current with respect to the voltage of the analyzed initial make-up bath copper plating solution into a value corresponding to the temperature of the copper plating solution that is being used. The concentration of the produced compound may be analyzed based on a value obtained by subtracting the converted value from the maximum value of the current or the integral value of the current with respect to the voltage of the copper plating solution used for copper plating.

(70) In the method of analyzing a plating preventing chemical species according to (58), (60), or (64), a copper plating solution obtained by making an analysis preventing material, which is included in the initial make-up bath copper plating solution or the copper plating solution that is being used, hardly soluble may be used.

(71) In the method of analyzing a produced compound according to (59), (61), or (65), a copper plating solution obtained by making an analysis preventing material, which is included in the initial make-up bath copper plating solution or the copper plating solution that is being used, hardly soluble may be used.

(72) In the method of analyzing a plating preventing chemical species according to (58), (60), or (64), a copper plating solution obtained by making an analysis preventing material, which is included in the initial make-up bath copper plating solution or the copper plating solution that is being used, hardly soluble with a chemical species which forms a hardly soluble compound with the analysis preventing material may be used.

(73) In the method of analyzing a produced compound according to (59), (61), or (65), a copper plating solution obtained by making an analysis preventing material, which is included in the initial make-up bath copper plating solution or the copper plating solution that is being used, hardly soluble with a chemical species which forms a hardly soluble compound with the analysis preventing material may be used.

(74) In the method of analyzing a plating preventing chemical species according to (58), (60), or (64), a copper plating solution obtained by making an analysis preventing material, which is included in the initial make-up bath copper plating solution or the copper plating solution that is being used, hardly soluble with cations which form a hardly soluble salt with the analysis preventing material may be used.

(75) In the method of analyzing a produced compound according to (59), (61), or (65), a copper plating solution obtained by making an analysis preventing material, which is included in the initial make-up bath copper plating solution or the copper plating solution that is being used, hardly soluble with cations which form a hardly soluble salt with the analysis preventing material may be used.

(76) In the method of analyzing a plating preventing chemical species according to (70), (72), or (74), silver ions, monovalent mercury ions, or thallium ions may be added to make the copper plating solution hardly soluble.

(77) In the method of analyzing a produced compound according to (71), (73), or (75), silver ions, monovalent mercury ions, or thallium ions may be added to make the copper plating solution hardly soluble.

(78) In the method of analyzing a plating preventing chemical species according to (58), (60), or (64), a plating solution that is obtained in stages by making a plurality of analysis preventing materials, which is included in the initial make-up bath copper plating solution or the copper plating solution that is being used, hardly soluble in stages may be used.

(79) In the method of analyzing a plating preventing chemical species or a produced compound according to any one of (70) to (77), after a pre-process selected from a precipitation process and/or a filtering process is performed to make the analysis preventing material, which is included in the initial make-up bath copper plating solution or the copper plating solution that is being used, hardly soluble, the analysis may be performed.

(80) A method of analyzing a monovalent copper chemical species in a mixture includes: contacting a mixture including the monovalent copper chemical species, which is an analyze target, and two or more kinds of chemical species other than the analyze target and/or a mist thereof with a first electrode and a second electrode; applying a voltage whose level varies in a range of 0.2 V to 2.0 V over time between the first and second electrodes; identifying the monovalent copper chemical species in the mixture in a voltage range in which the maximum value of a current flowing between the first and second electrodes is observed; and analyzing the concentration of the monovalent copper chemical species in the mixture based on the maximum value of the current or the integral value of the current with respect to the voltage.

(81) In the method of analyzing a monovalent copper chemical species in a mixture according to (80), an analysis preventing material included in the mixture may be made hardly soluble. The voltage whose level varies in the range of 0.2 V to 2.0 V over time may be applied between the first and second electrodes. The monovalent copper chemical species in the mixture may be identified in the voltage range in which the maximum value of the current flowing between the first and second electrodes is observed. The concentration of the monovalent copper chemical species in the mixture may be analyzed based on the maximum value of the current or the integral value of the current with respect to the voltage.

(82) The method of analyzing a monovalent copper chemical species in a mixture according to (80) or (81) may further include: providing a third electrode that supplies at least a portion of the potential thereof to the first electrode or the second electrode at the same polarity or different polarities; and contacting the mixture with the third electrode.

(83) In the method of analyzing a monovalent copper chemical species in a mixture according to any one of (80) to (82), the concentration of the monovalent copper chemical species in the mixture may be analyzed based on a value obtained by subtracting the maximum value of the current or the integral value of the current, which is obtained from a reference solution instead of the mixture, from the maximum value of the current or the integral value of the current with respect to the voltage, which is obtained from the mixture.

(84) In the method of analyzing a monovalent copper chemical species in a mixture according to (83), the temperature difference between the reference solution and the mixture may be within 10° C.

(85) In the method of analyzing a monovalent copper chemical species in a mixture according to (83), the temperature of the reference solution and the temperature of the mixture may be measured. The rate of change of the maximum value of the current or the integral value of the current with respect to the voltage of the reference solution, which is separately analyzed, according to the temperature may be used to covert the maximum value of the current or the integral value of the current of the analyzed reference solution into a value corresponding to the temperature of the mixture. The concentration of the monovalent copper chemical species may be analyzed based on a value obtained by subtracting the converted value from the maximum value of the current or the integral value of the current of the mixture.

(86) In the method of analyzing a monovalent copper chemical species in a mixture according to any one of (80) to (83), a mixture obtained by making an analysis preventing material included in the reference solution or the mixture hardly soluble with a chemical species which form a hardly soluble compound with the analysis preventing material may be used.

(87) In the method of analyzing a monovalent copper chemical species in a mixture according to any one of (80) to (83), a mixture obtained by making an analysis preventing material included in the reference solution or the mixture hardly soluble with cations which form a hardly soluble salt with the analysis preventing material may be used.

(88) In the method of analyzing a monovalent copper chemical species in a mixture according to (86) or (87), silver ions, monovalent mercury ions, or thallium ions may be added to make the solution hardly soluble.

(89) In the method of analyzing a monovalent copper chemical species in a mixture according to any one of (80) to (83), after a pre-process selected from a precipitation process and/or a filtering process for filtering a precipitate by the precipitation is performed to make the analysis preventing material included in the reference solution or the mixture hardly soluble, the analysis may be performed.

In the invention, the term "analysis" used in the description of the invention means qualitatively determining whether there is a chemical species that the operator wants to know and/or quantitatively determining an increase in the concentration of a chemical species that the operator wants to know.

Effects of the Invention

According to the sensor of the invention, when the wiring line is insulated, the function of the electrode is separated from the function the wiring line. As a result, the area of the electrode is constant regardless of the depth or angle of the sensor immersed in a liquid, mist, or gas, which is an analyze target. Therefore, the reproducibility of quantitative analysis is improved.

In addition, it is possible to provide an inexpensive sensor by forming an organic insulating portion.

When the organic substrate is used, it is possible to achieve both the design reproducibility of the area of the electrode and the insulation between the wiring lines with a single-layer organic member, such as an organic coverlay, by the insulation of a wiring line portion by the organic coverlay and the designability of an effective electrode area by the definition of the area of the opening.

The sensor system according to the invention includes the above-mentioned sensor. Therefore, it is possible to integrally and continuously perform a pre-process with high efficiency.

According to the sensor of another aspect of the invention, since a wiring structure is insulated and coated by an organic material, it is possible to obtain a flexible sensor. The insulation between the wiring lines is maintained to be uniform along the wiring lines, and it is possible to ensure measures for preventing the leakage of a current. In the formation of the electrode, the organic material is coated on the cross section of a conductive line, and is removed by a laser such that the electrode is exposed. Therefore, it is possible to flexibly correspond to low-volume production and mass production. This structure can be applied to the existing wire product and cable, and it is possible to improve flexibility in the design of the system.

According to the sensor of still another aspect of the invention, an insulating substrate for a sensor does not require chemical resistance and heat resistance. In particular, it is possible to provide a sensor with an electrode structure that does not require an alignment and masking process for ensuring the insulating property between the electrodes when a carbon including layer is formed. Specifically, as a process for manufacturing the substrate for a sensor, it is possible to select a multi-layer forming process including all kinds of organic materials including an organic material with heat resistance capable of corresponding to a vacuum process and/or chemical resistance and an inorganic material that cannot correspond to these characteristics. In addition, an alignment and masking process for ensuring the insulating property between the electrodes when a carbon including layer is formed is not needed. Therefore, it is possible to manufacture a substrate with high accuracy and high efficiency. The carbon including layer can prevent the contamination of the substrate and makes it possible to obtain an organic substrate having resistance to the formation of a minute electrode by vacuum film formation, which is required in the analysis of a complex system.

The carbon including layer covering the surface of the reference electrode stabilizes a base current and the potential of the reference electrode. The carbon including layer covering the working electrode makes it possible to form a metal layer made of a single component or a composite component with a uniform area using, for example, a vapor deposition method, a sputtering method, a printing method, or an ink jet method. The uniform area is achieved by preventing a variation in the area of the electrode due to the infiltration of an analyte into the interface between the electrode and an insulating material. In this way, it is possible to manufacture an electrode with sufficient durability to repeatedly perform measurement on the same substrate.

In the analysis of a complex system, a plurality of working electrodes having an organic monolayer formed thereon is formed while changing their areas. Then, multi-point analysis is performed to analyze a variation in the obtained potential or the time required to reach a specific potential. Therefore, it is possible to analyze concentration within a wide range. In particular, when minute electrodes are formed and it is necessary to analyze a very small amount of material, it is necessary to form a substrate capable of corresponding to a vacuum film forming method, such as gold vapor deposition or sputtering. Since this organic substrate has a carbon including layer with heat resistance formed thereon, it is possible to perform gold vapor deposition or sputtering, and gives a means for introducing a vacuum film forming method that has not been available in the organic substrate. In the vacuum film forming method, since the carbon including layer is formed on a base, the surface roughness of the wiring line and the electrode on the organic substrate is reduced, and it is possible to activate the induction of the surface potential of the organic monolayer.

The sensor system according to the invention includes the above-mentioned sensor. Therefore, it is possible to provide a sensor system capable of integrally and continuously performing a pre-process with high efficiency.

The portable sensor system according to the invention includes the above-mentioned sensor. Therefore, it is possible to provide a portable sensor system that can be carried to a desired place and easily analyze a very small amount of analyte in a short time on the spot.

According to the method of analyzing metal ions according to the invention, it is possible to analyze a monovalent copper chemical species from a complex system included in an analysis preventing material or a plurality of metal ions relatively easily and with high reproducibility. In the analysis of a complex system, that is, in high-accuracy analysis, the invention has an effect of simplifying a complicated pre-process. That is, it is possible to omit a complicated pre-process indispensable to the analysis of a complex system, that is, high-accuracy analysis. In addition, particularly, in the analysis of monovalent copper, it is possible to provide a method of qualitatively and quantitatively analyzing metal ions using a combination of an electrochemical method and a colorimetric method.

The mounting substrate according to the invention has a structure in which the electrode and the carbon including layer of the coverlay surface that need to be insulated from each other when the carbon including layer is formed on the electrode in the same process are separated from each other by the recession structure of the coverlay and the surface of the coverlay surface is coated. It is possible to form electrodes capable of improving the characteristics of a sliding portion for connection to a connector and the characteristics of semiconductor chip mounting according to the related art, such as gold wire bonding. That is, it is possible to significantly reduce a load applied to the cleaning management of gold electrodes which are contaminated with a plating solution. A black carbon including layer coated on the surface of the coverlay can prevent the generation of a small amount of current induced by the extending wiring line due to optical reaction. In the mounting substrate to which a high-speed switching signal is applied, the carbon including layer can attenuate switching noise. Therefore, it is possible to ensure a noise margin.

According to the method of analyzing a plating preventing material or the method of analyzing a produced compound according to the invention, it is possible to analyze a plating preventing chemical species included in a plating solution having an analysis preventing material or a large amount of bivalent copper, and a compound produced when a plating solution is used relatively easily and with high reproducibility.

The method of analyzing a monovalent copper chemical species according to the invention can be used to analyze other metal ions. For example, the method can analyze soil in an environment and ions related to a medical and health field, in addition to an industrial chemical group such as a plating solution.

BRIEF DESCRIPTION OF THE DRAWINGS

FIG. 18 is a perspective view illustrating the twin-peak kit including a temperature-controlled tank.

EXPLANATION OF REFERENCE NUMERALS

Figure 1:
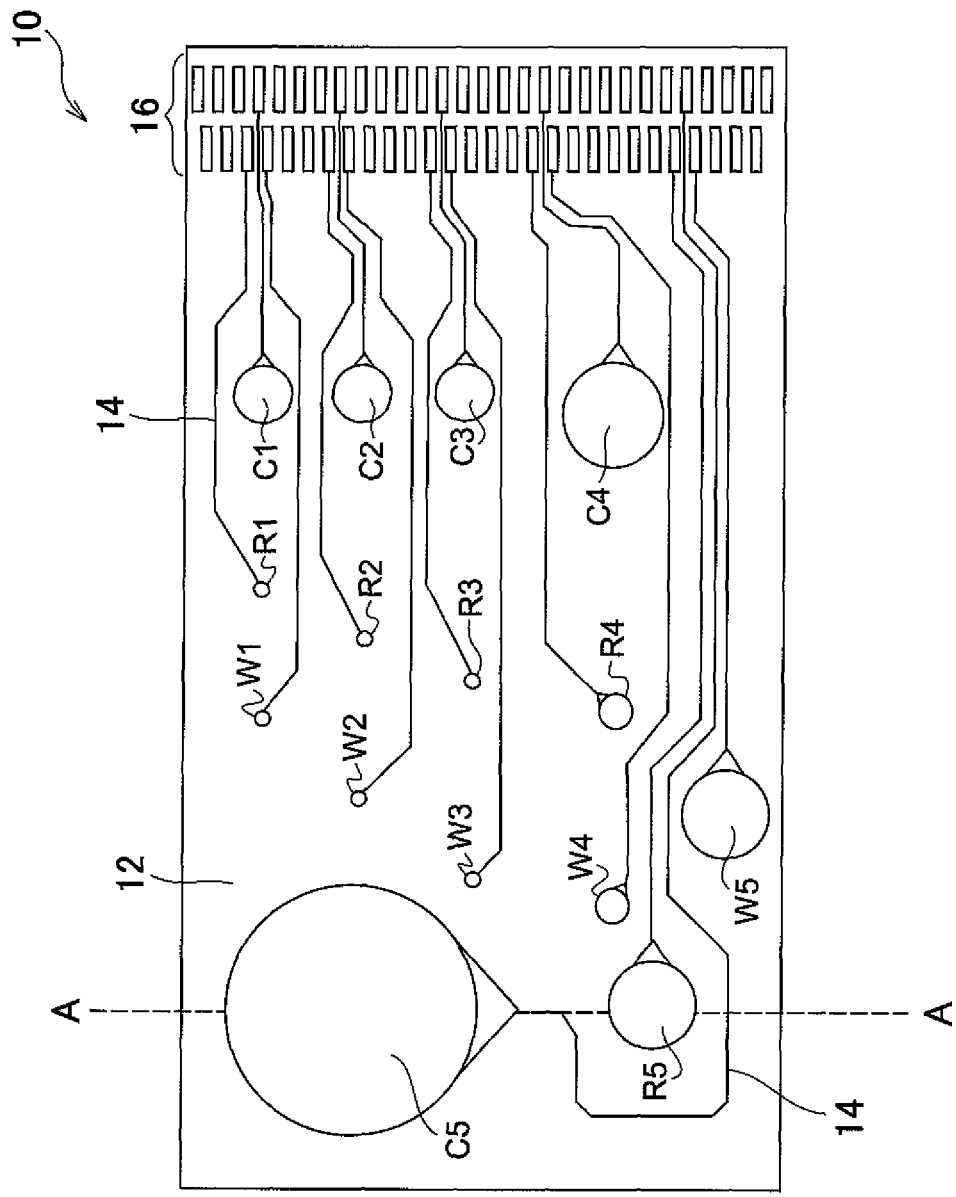
FIG. 1 is a diagram illustrating the wiring pattern of a substrate of a metal ion sensor according to the invention.

10: Metal ion sensor
12: Insulating substrate
14: Extending wiring line
15: Conductor for buried connection
16: Measuring terminal (group)
18: Electrode
20: Connector mounting terminal unit
22: Terminal unit
24: Extending wiring line
30: Coverlay
30A: Coverlay film
30B: Adhesive layer
32: Opening
40: Insulating substrate
42: Reinforcing member (polyimide)
44: Adhesive
46: Base material
50: Carbon including layer
60: Twin-peak kit
62: Analysis liquid container (cylinder)
64: Analysis liquid container (cylinder)
65: Air hole
66: Filter
68: Piston
70: Piston
80: Reference electrode
82: Counter electrode
84: Working electrode
90, 92: Analysis liquid container
94: Temperature control layer
C1, C2, C3, C4, C5: Counter
R1, R2, R3, R4, R5: Reference electrode
W1, W2, W3, W4, W5: Working electrode

BEST MODE FOR CARRYING OUT THE INVENTION

A sensor according to the invention includes: first and second conductive electrodes; first and second conductive wiring lines that are respectively connected to the first and second conductive electrodes; and an insulating portion that insulates the first wiring line from the second wiring line and insulates the first and second wiring lines from a liquid, mist, or gas including an analyte. The insulating portion is made of an organic material, and at least the surfaces of portions of the first and second electrodes that come into contact with the liquid, the mist, or the gas including the analyte are made of a material that is insoluble by the liquid or the mist including the analyte or a material that is not eroded by the gas including the analyte.

The simplest structure of a metal ion sensor (in some cases, simply referred to as an ion sensor) to which the sensor according to the invention is applied includes at least first and second electrodes and first and second connection wiring lines that are electrically connected to the first and second electrodes and are covered with an insulating portion made of an organic material. In this embodiment, the ion sensor further includes a third electrode that is supplied at the same polarity or a different polarities and a third connection wiring line that is electrically connected to the third electrode and is covered with an organic insulating portion, which will be described in detail below. The surface of at least a portion of the third electrode that comes into contact with a liquid, mist, or gas including an analyte is made of a material that is not soluble by the liquid or mist including the analyte, or a material that is not corroded by the analyte. Some examples of sensors are disclosed together with examples of an analysis method according to the invention. However, combinations of the analysis methods and the sensors disclosed therein are not fixed, but the analysis methods according to examples may be implemented using other sensors.

The ion sensor, which will be described in detail below, includes a insulating substrate, an electrode group including first, second, and third electrodes that are arranged on the same surface of the insulating substrate, a connection wiring line group that includes one or more layers and is electrically connected to the electrode group, and a connection terminal or measuring terminal group that is electrically connected to the connection wiring line group. Actually, in many cases, the first and second electrodes are called a working electrode and a counter electrode, and the third electrode is called a reference electrode.

Specifically, a coverlay having openings formed therein through which each of the electrode groups is exposed to the outside is provided on the insulating substrate, and a carbon including layer is formed at least on the surface of the coverlay and the surface of the electrode disposed in the opening. The structure before the carbon including layer is formed is also included in the embodiment of the invention, and a portion of the connection wiring line surrounded by an organic coverlay and an organic insulating substrate is an insulating portion of the connection wiring line made of an organic material.

The above-mentioned aspect will be described below.

As described above, the organic insulating material used in the sensor according to the invention is not particularly limited. For example, organic materials, such as polyimide, epoxy, and liquid crystal polymer, may be used. In particular, among the above-mentioned materials, it is preferable to use the liquid crystal polymer or Teflon (registered trademark) as the organic insulating material.

As the wiring material used in the sensor according to the invention, any of the following materials may be used: an electrolytic copper foil; a rolled copper foil; a thin copper film; materials obtained by coating the foils and the film with gold using plating, sputtering, or vapor deposition; a copper line; a gold line; a silver line; a platinum line; and an alloy line of platinum and iridium. For example, subtractive, additive, and wiring line transfer methods may be applied to the wiring substrate. For example, a semi-hardened and/or hardened thermosetting resin, a photo-curable resin, or a thermoplastic resin may be used as the insulating material.

As the thermosetting resin, any of the following materials may be used: at least one selected from an epoxy resin; a bismaleimide triazine resin, a polyimide resin, a cyanoacrylate resin, a phenolic resin, an unsaturated polyester resin, a melamine resin, a urea resin, a polyisocyanate resin, a furan resin, a resorcinol resin, a xylene resin, a benzoguanamine resin, a diallyl phthalate resin, a silicon modified epoxy resin, a silicon modified polyamideimide resin, and a benzocyclobutene resin; and materials obtained by heating mixtures of the resins and a hardener or a hardening accelerator and hardening or partially hardening the mixtures, if necessary.

As the photo-curable resin, any of the following materials may be used: at least one selected from an unsaturated polyester resin, a polyester acrylate resin, a urethaneacrylate resin, a silicon acrylate resin, and an epoxy acrylate resin; and materials obtained by exposing or heating mixtures of the resins and a photo initiator, a hardener, or a hardening accelerator and hardening or partially hardening the mixture, if necessary.

As the thermoplastic resin, any of the following materials may be used: at least one selected from a polycarbonate resin, a polysulfone resin, a polyetherimide resin, a thermoplastic polyimide resin, a polytetrafluoroethylene resin, a polyhexafluoropropylene resin, a polyether ether ketone resin, a vinyl chloride resin, a polyethylene resin, a polyamideimide resin, a polyphenylene sulfide resin, a polyoxybenzoate resin, and a liquid crystal polymer; materials obtained by heating mixtures of the resins and a hardener or a hardening accelerator and hardening or partially hardening the mixtures, if necessary.

The insulating resin may be a insulating resin composition, which is a mixture of different kinds of resins, and the insulating resin composition may include an inorganic filler, such as a silica or a metal oxide, as a filler. The inorganic filler may be conductive particles, such as nickel, gold, or silver particles, or resin particles plated with these metal materials. In addition, materials impregnated with the nonwoven fabric or woven fabric of glass fiber may be used as the inorganic filler.

Next, the structure of the electrode of the sensor according to the invention will be described with reference to the drawings. The invention is not limited to the following embodiments. Various modifications and other aspects of the invention can be made within the scope and spirit of the invention.

FIG. 1 is a diagram illustrating a metal ion sensor 10 according to the invention, and shows the basic wiring pattern of a throwaway substrate. In FIG. 1, C, R, and W denote a counter electrode, a reference electrode, and a working electrode (corresponding to examples of a second electrode, a third electrode, and a first electrode), respectively. Suffixes 1 to 5 of the characters C, R, and W indicate set numbers of C, R, and W, and correspond to examples of the structures of the electrodes used to measure current-voltage characteristics or voltages. They form one electrode group. In FIG. 1, five electrode groups are arranged, and each electrode may have any shape, such as a circular shape or a rectangular shape. An extending wiring line (wiring member) 14 extends from each electrode to a measuring terminal (connection terminal) 16 that is fitted and connected to a connector provided at the edge of the substrate. In general, the wiring line connected to the electrode has a tapered shape in order to reduce stress and prevent the cutting of the wiring line. In addition, the extending wiring line 14 passes through the electrodes. In a substrate with a predetermined size, when the number of electrodes increases or the pitch between the electrodes is reduced, it is necessary to increase the number of wiring lines passing through the electrodes. As a result, it is necessary to reduce the width of the wiring line and the gap between the wiring lines. Therefore, it is very important to ensure insulating property between the extending wiring lines. For example, the wiring line may be formed by forming a direct gold plating layer after copper etching.

Figure 36:
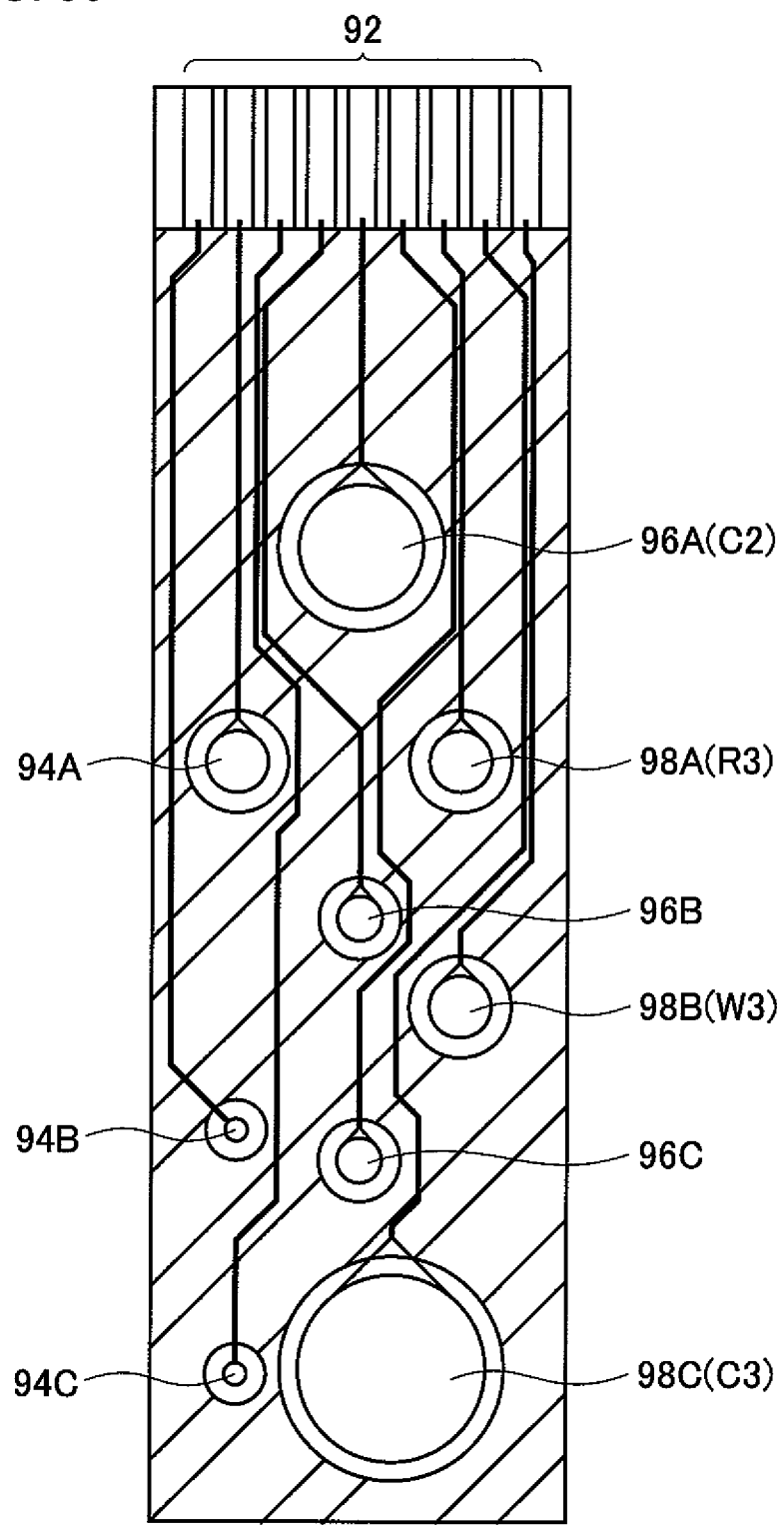
FIG. 36 is a top view illustrating a coverlay adhered to the sensor substrate shown in FIG. 34.

The reference electrode, the working electrode, and the counter electrode may be arranged such that the working electrode is separated from the counter electrode with the reference electrode interposed therebetween. This arrangement makes it possible to increase a current value, which contributes to increasing sensitivity. For example, in FIG. 36, an example in which R3, C3, and C2 are used as the reference electrode, the counter electrode, and the working electrode corresponds to this arrangement.

Figure 2:
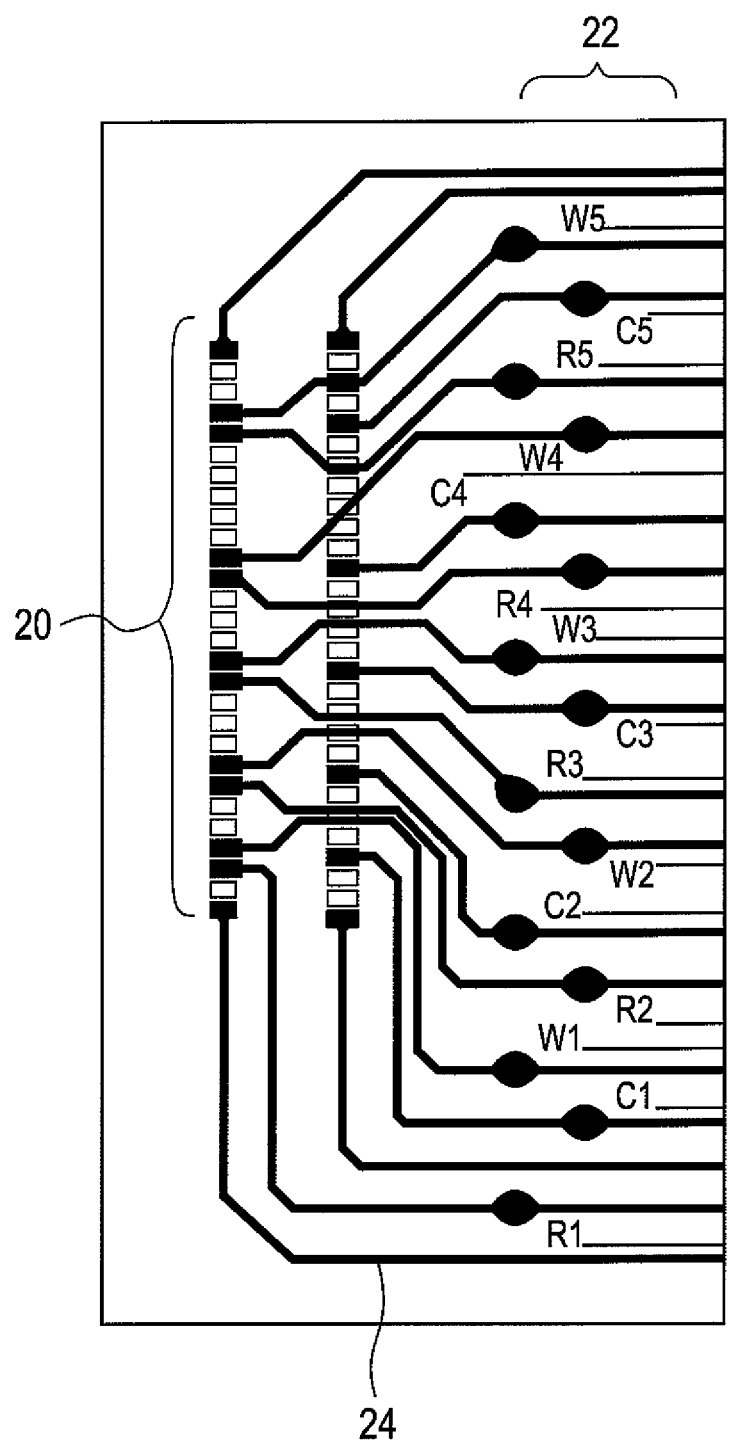
FIG. 2 is a diagram illustrating the surface mounting pattern of a connector fitted to the metal ion sensor according to the invention.

FIG. 2 is a diagram illustrating a pattern for mounting connectors on the surface of the fitted substrate used in a sensor unit. Reference numeral 20 denotes a connector mounting terminal unit (connection terminal), reference numeral 22 denotes a terminal unit for mounting wiring lines and members connected to a measuring device, and reference numeral 24 denotes an extending wiring line that extends from the connector mounting terminal unit 20 to the terminal unit 22. In FIG. 2, the connector mounting terminal unit 20 that is not used is represented by a white rectangular, and only one extending wiring line is denoted by reference numeral 24. However, the extending wiring lines 24 connect the connector mounting unit 20 and the terminal unit 22. As such, it will be easily understood that, when the number of electrodes is increased, the substrate on which the connectors are mounted needs to have a multi-layer structure; otherwise, it is very difficult to perform multi-point analysis.

Figure 3:
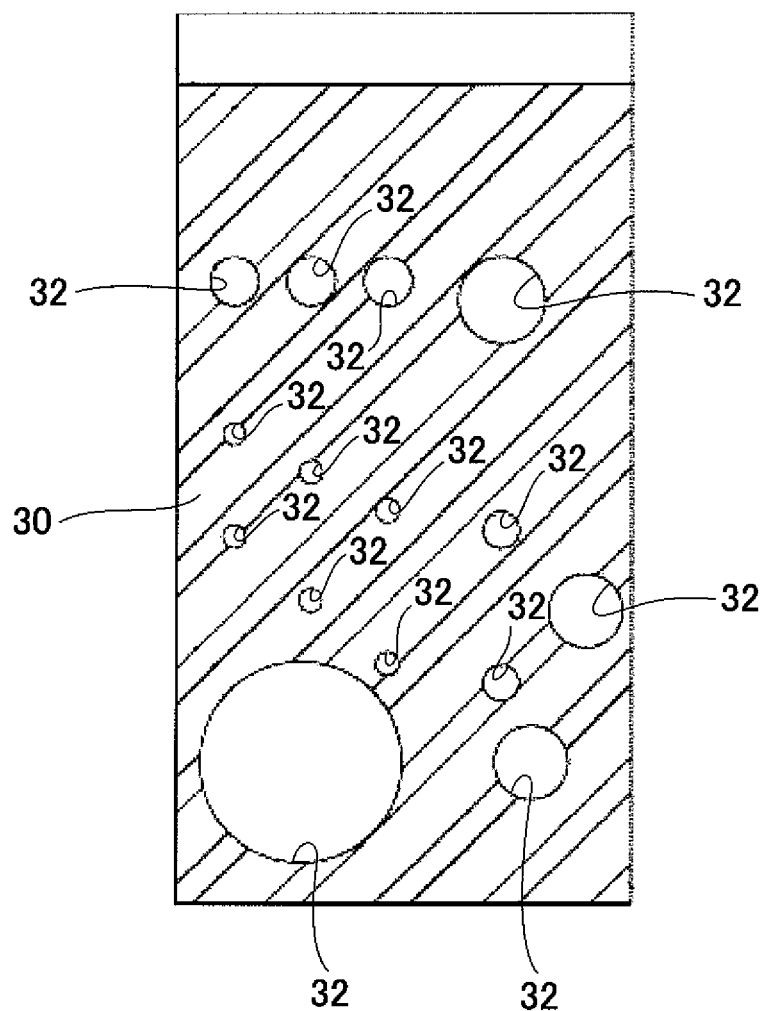
FIG. 3 is a diagram illustrating the hole pattern (opening pattern) of a coverlay.
Figure 4:
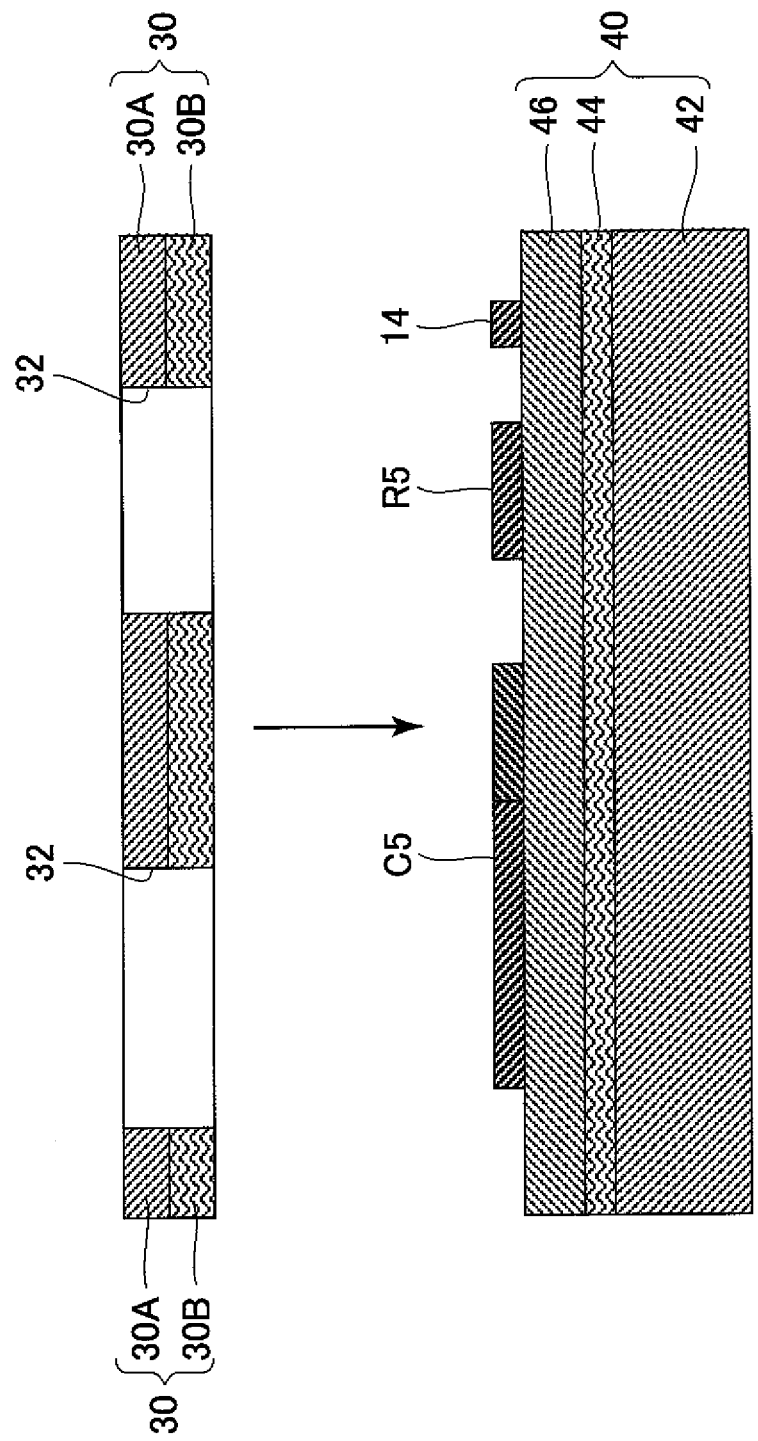
FIG. 4 is a diagram illustrating an observed cross section (before coverlay is covered) taken along the line A-A of FIG. 1.

FIG. 4 is a cross-sectional view taken along the line A-A of FIG. 1. It is preferable that a direct gold plating layer be formed on the surfaces of the wiring lines after copper etching. After the direct gold plating layer is formed, the surfaces of the wiring lines are covered with a coverlay 30 shown in FIG. 3 such that only electrode portions, the peripheral portions thereat and terminal portions that are fitted and connected to the connectors are exposed. The coverlay 30 includes openings 32 which correspond to each electrode and through which the electrode groups are exposed to the outside. In FIG. 3, in the coverlay 30, each opening 32 is provided above the electrode which is exposed to the outside through the opening 32 and the area of each opening is slightly more than that of the electrode (the opening has a clearance that is 200 µm more than that of the electrode and has a diameter that is 400 µm more than that of the electrode). The clearance is also called a creeping distance. This correlation is suitable to cover all the electrodes with a carbon including layer, which will be described below.

However, in this case, since a portion of the wiring line connected to the electrode is not covered with the coverlay, there is a concern that the portion will serve as an electrode. Therefore, in order to strictly define the area of the electrode, the edge of the opening 32 is disposed inside the electrode.

In the invention, the coverlay is made of an insulating organic material. However, the coverlay may be made of a single material or it may include a coverlay film and an adhesive layer. When the coverlay is made of a single material, it is preferable that a liquid crystal polymer be used as the single material.

When the coverlay includes the coverlay film and the adhesive layer, for example, a polyimide film or a liquid crystal polymer may be used as the coverlay film. Specifically, for example, CISV1215 manufactured by NIKKAN INDUSTRIES CO., LTD., or STABIAX or BAIC-C manufactured by JAPAN GORE-TEX INC. may be used.

As the resin used for the adhesive layer, any of the following materials may be used: an acrylic-resin-based adhesive, an epoxy-resin-based adhesive, and a liquid crystal polymer. It is preferable to use the liquid crystal polymer.

It is preferable that the thickness of the coverlay be matched with the thickness of the connector. For example, when the thickness of a base material fitted to the connector is 200 µm±30 µm, it is preferable that the thickness of the coverlay be in the range of 100 µm to 200 µm. When the thickness of the base material fitted to the connector is 300 µm±30 µm, it is preferable that the thickness of the coverlay be in the range of 150 µm to 300 µm.

Figure 5:
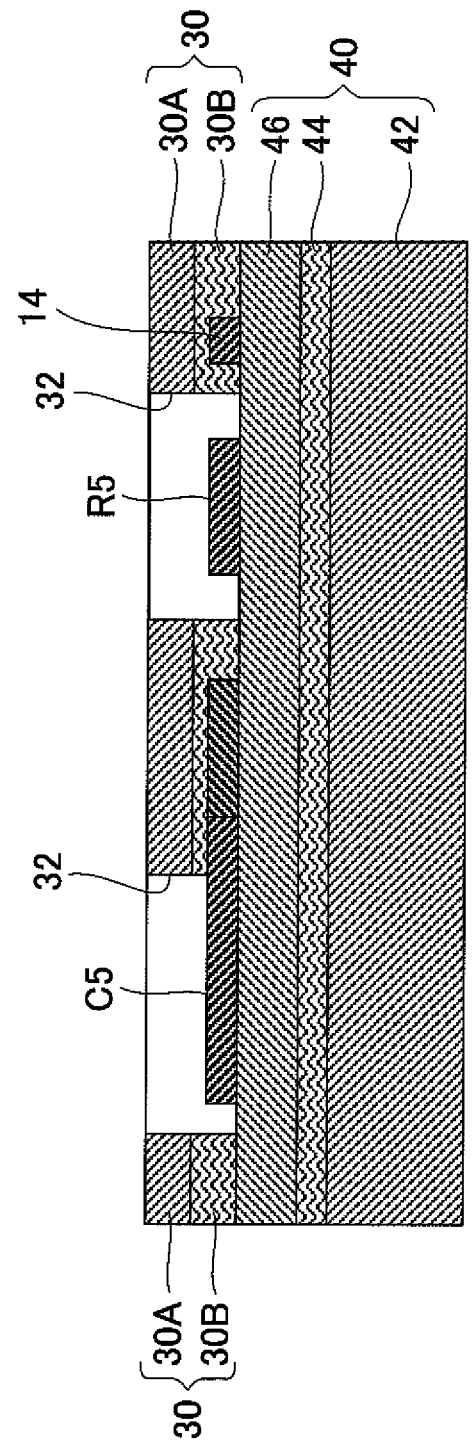
FIG. 5 is a cross-sectional view illustrating a substrate covered with the coverlay shown in FIG. 3.
Figure 6:
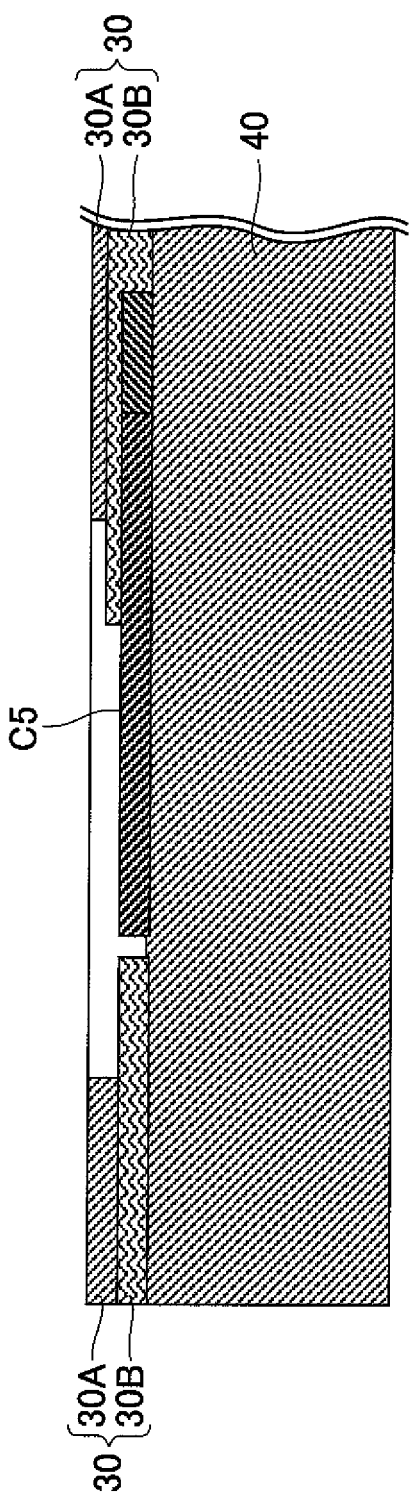
FIG. 6 is an enlarged view illustrating the vicinity of a left opening in FIG. 5 and shows the infiltration state of an adhesive from the coverlay.

As such, the electrode is covered with the coverlay in order to protect the extending wiring lines and prevent a current leakage between the wiring lines due to immersion during analysis. FIG. 5 is a cross-sectional view illustrating an insulating substrate 40 and the coverlay 30 that covers the surface of the insulating substrate 40 on which, for example, electrodes are formed. In this case, the coverlay may be adhered to the insulating substrate with an iron without applying a relatively large load. However, since the extending wiring line 14 is exposed in a convex shape from the surface, it is necessary to fill the gap between the wiring lines with the coverlay 30. Therefore, it is preferable to apply predetermined pressure at a predetermined temperature for a predetermined time. However, in the manufacturing process, the adhesive layer of the coverlay is infiltrated. FIG. 6 is an enlarged view illustrating the left side of the opening shown in FIG. 5 and shows the infiltration of the adhesive layer. The infiltration of the adhesive layer is likely to contaminate the surface of the electrode, which may result in a reduction in yield.

Figure 7:
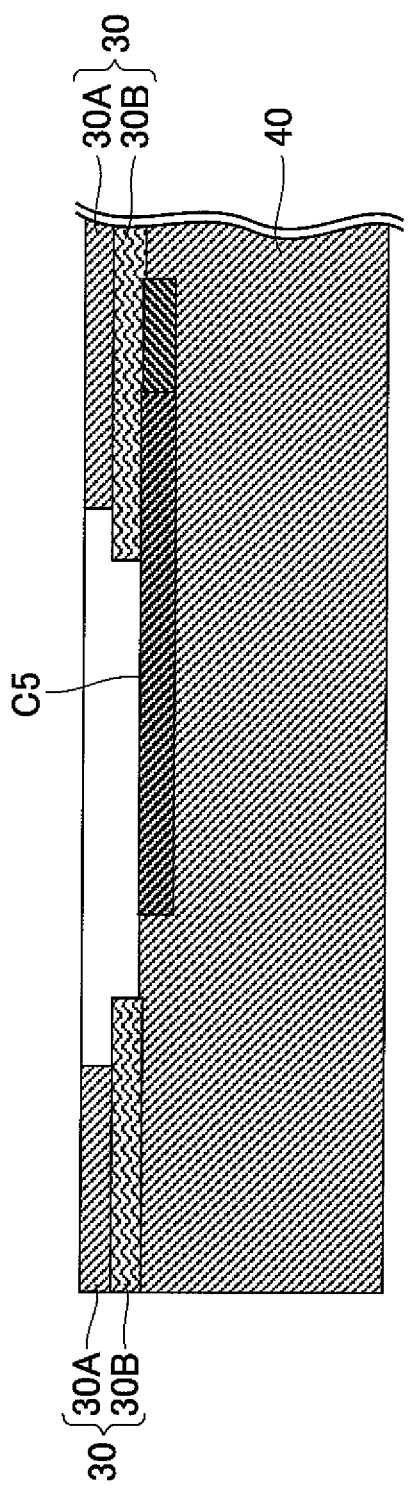
FIG. 7 is a cross-sectional view when a wiring line is transferred into the substrate.

As shown in FIG. 4, an adhesive 44 is adhered to a reinforcing member 42. In this ease, when there is a very small amount of air at the interface therebetween, the air is expanded when the coverlay 30 is adhered, and the reinforcing member 42 peels off, which causes a reduction in yield. It is preferable to increase the clearance in order to prevent the contamination of the surface of the electrode due to the infiltration of the adhesive. Preferably, as shown in FIG. 7, when the wiring line is transferred into the insulating substrate 40, it is not necessary to increase the pressure or temperature required to fill up the gap between the wiring lines, as compared to adhesion conditions to a flat surface, and it is possible to significantly reduce the amount of adhesive that is infiltrated. Alternatively, an adhesive 30B adhered to a coverlay film 30A may be dried in advance and then adhered to the insulating substrate. In this way, it is possible to reduce the amount of flow of the adhesive.

It is preferable to transfer the wiring lines into the insulating substrate 40 in order to prevent the reinforcing member 42 from peeling off. In this case, it is not necessary to apply the pressure or temperature required to fill up the gap between the wiring lines with the coverlay 30. As a result, it is possible to prevent the expansion of air causing the peeling-off of the reinforcing member.

Figure 8:
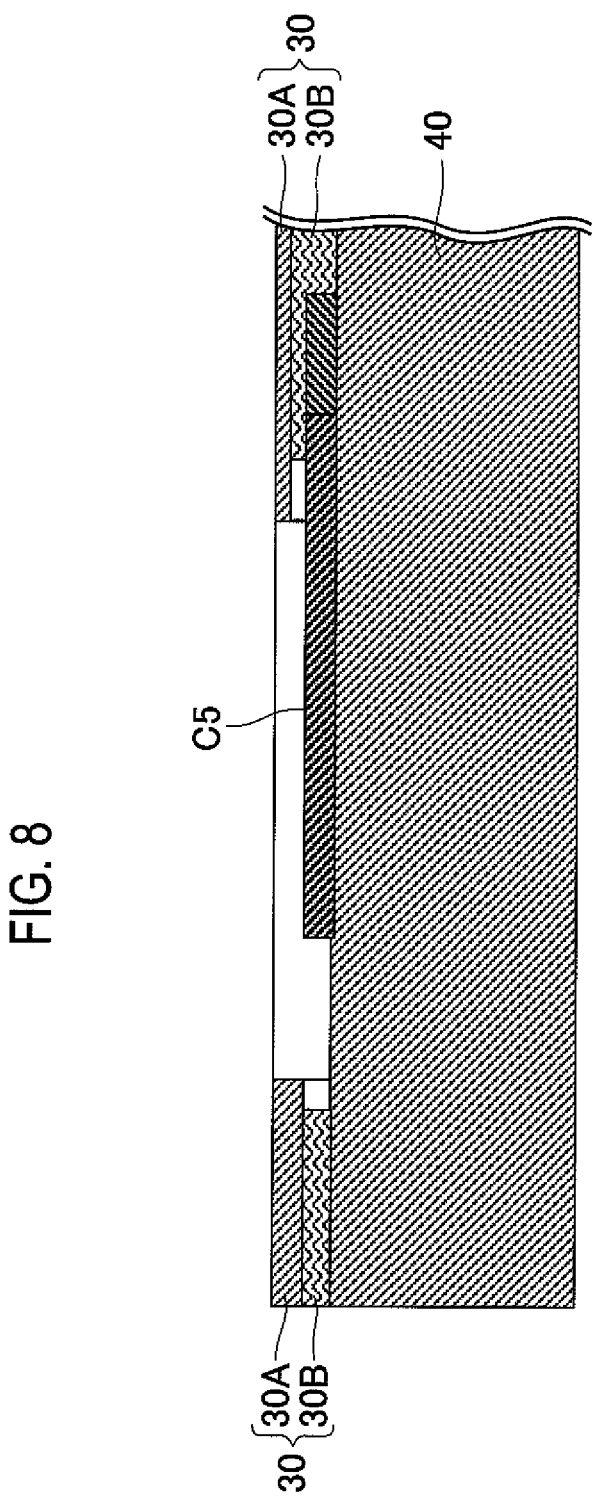
FIG. 8 is a cross-sectional view illustrating the state where an etchback process is performed on the covered coverlay.

In addition, it is preferable to selectively remove and recess (etchback) the adhesive layer 30B of the coverlay 30 from the edge of the opening by a predetermined amount in order to prevent the infiltration of the adhesive. That is, it is preferable to dispose the edge of the opening of the adhesive layer 30B outside the edge of the opening of the coverlay film 30A, which is shown in FIG. 8. Alternatively, the opening of the coverlay may be formed such that the diameter thereof is increased from the upper surface to the lower surface. When the coverlay is made of a single material, the opening of the coverlay may be formed such that the area of the opening in the upper surface is less than that of the opening in the lower surface.

An etchback process may be performed in the following order.

For example, when the thickness of the adhesive layer is 15 µm, it is necessary to etchback the adhesive layer by a width of at least 15 µm from the edge of the opening in order to ensure a sufficient insulating property. An example of an optimal process method corresponding to the structure is described below.

(1) A substrate is cleaned with water. (2) The substrate is immersed in DMF (for 5 minutes) according to the amount of infiltration before the subsequent process. (3) The substrate is immersed in a solution including 30 to 60 g/L of potassium permanganate and 20 to 40 g/L of sodium hydroxide at a room temperature to 90° C., preferably, 60° C. for 5 minutes to 60 minutes, preferably, 20 minutes. (4) The substrate is cleaned with water. (5) Since the solution in the process (3) is an alkali solution, the substrate is immersed in 0.3 N (8 ml/L) of sulfuric acid for 5 minutes for neutralization. (6) The substrate is tracked out (cleaning with water). (7) The substrate is cleaned with water. (8) The substrate is dried at 100° C. for 5 minutes.

As described above, the adhesive layer may be removed and recessed by chemicals or an adhesive surface may be processed by a router in advance. In addition, as a mechanical method that does not perform removing and recess with chemicals, preferably, the following method is effective in which two coverlays are prepared and openings are formed such that the diameter of an opening in the upper coverlay is more than that of the opening in the lower coverlay.

When the coverlay includes a cover film and an adhesive layer, preferably, a liquid crystal polymer film BIAC-C manufactured by JAPAN GORE-TEX INC. is used as the cover film, and KS-7003 or KS-6600-7F with low flowability manufactured by HITACHI CHEMICAL CO., LTD. may be used as the adhesive layer.

As a result of an intensive consideration by the inventors, in the above-mentioned structure, when a carbon including layer was formed on the surface of the substrate having the coverlay formed thereon, it was possible to ensure insulating property between a plurality of opening electrode portions. That is, this is because an etchbacked portion insulates the carbon including layer formed on the coverlay surface from an electrode surface layer formed on the surface of the electrode.

It is preferable to use a vapor deposition method in order to form the carbon including layer. Preferably, a carbon vapor deposition method (see Japanese Patent No. 3660866), which is a tough carbon method using an ion cluster beam capable of forming a film at a temperature of 100° C. or less, is used as the vapor deposition method. The thickness of the carbon including layer is as large as possible. However, the thickness of the carbon including layer is preferably in the range of 0.1 µm to 1 µm, more preferably, equal to or more than 0.3 µm, in terms of manufacturing costs. If the thickness of the carbon including layer is equal to or more than 0.1 µm, a base material (for example, copper or gold) forming the wiring line is hardly affected electrochemically, and the reference electrode is stabilized. Therefore, the above-mentioned thickness range is most suitable to reduce the size of the reference electrode.

It is preferable to apply a print paste using an ink jet method in order to effectively produce the sensor. For example, the technique and paste disclosed in JP-A Nos. 2006-147202, 2007-165708, and 2007-165709 may be applied as the print paste. Specifically, carbon paste manufactured by HITACHI CHEMICAL CO., LTD. may be preferably used. In addition, as a printing method, an application method using a syringe may be used. The hardening temperature is in the range of 160° C. to 210° C. and may be appropriately set depending on the heat resistance of a base material.

In an immersion method using an alternate stacking method or a printing method with carbon paste, the carbon including layer may be formed in an etchback structure. Therefore, when an atmospheric plasma apparatus manufactured by SEKISUI CHEMICAL CO., LTD or a plasma processing apparatus is used to abrade the surface using a plasma process with oxygen and/or argon, and a mixture of oxygen and argon to make a hydrophilic surface and the carbon including layer is formed on the surface, the carbon including layer is not formed in an etchback portion, and insulating property between the carbon including layer formed on the surface of the coverlay and the electrode surface layer formed on the surface of the electrode is ensured. In this case, it is preferable to perform a hydrophobic treatment before the surface is abraded. For example, HMDS (hexamethyldisilazane) or a coating agent including fluorine may be used in the hydrophobic treatment.

Figure 9:
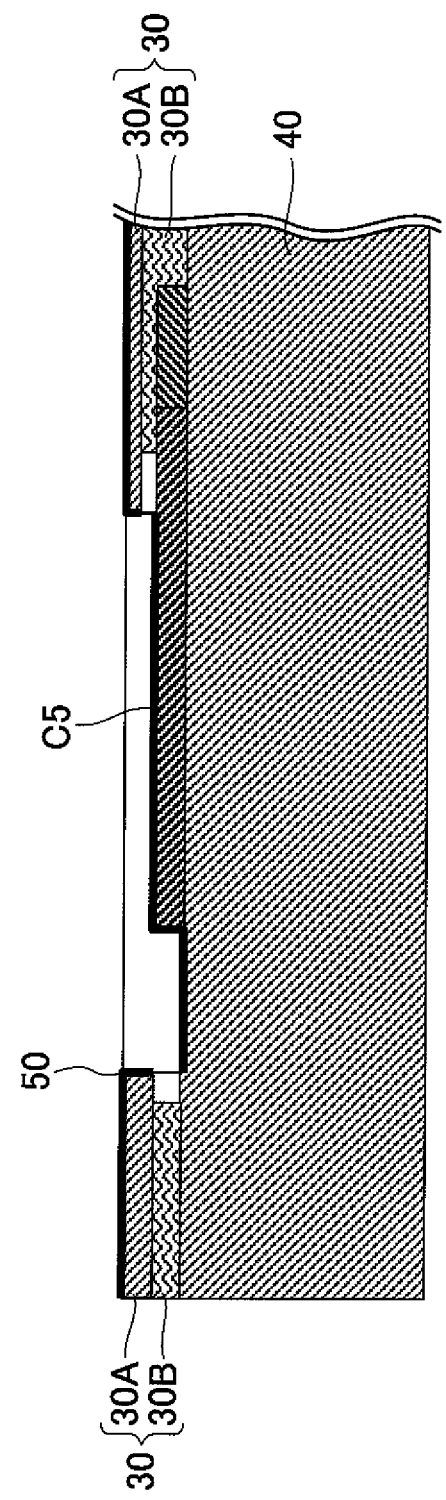
FIG. 9 is a cross-sectional view illustrating the state where a carbon including layer is formed after the etchback process.

FIG. 9 shows the state where a carbon including layer 50 is covered in this way. In FIG. 9, the carbon including layer 50 is formed on the entire surface of the coverlay 30 and is formed on the surface of the electrode C5 and the surface of the insulating substrate 40 in the opening. As shown in FIG. 9, when there is a clearance between the opening of the coverlay 30 and the edge of the electrode C5, the carbon including layer 50 is formed on the surface of the insulating substrate 40. On the other hand, when there is no clearance therebetween, the carbon including layer 50 is not formed on the surface of the insulating substrate 40. That is, the carbon including layer 50 is formed at least on the surface of the electrode in the opening of the coverlay 30.

Figure 10:
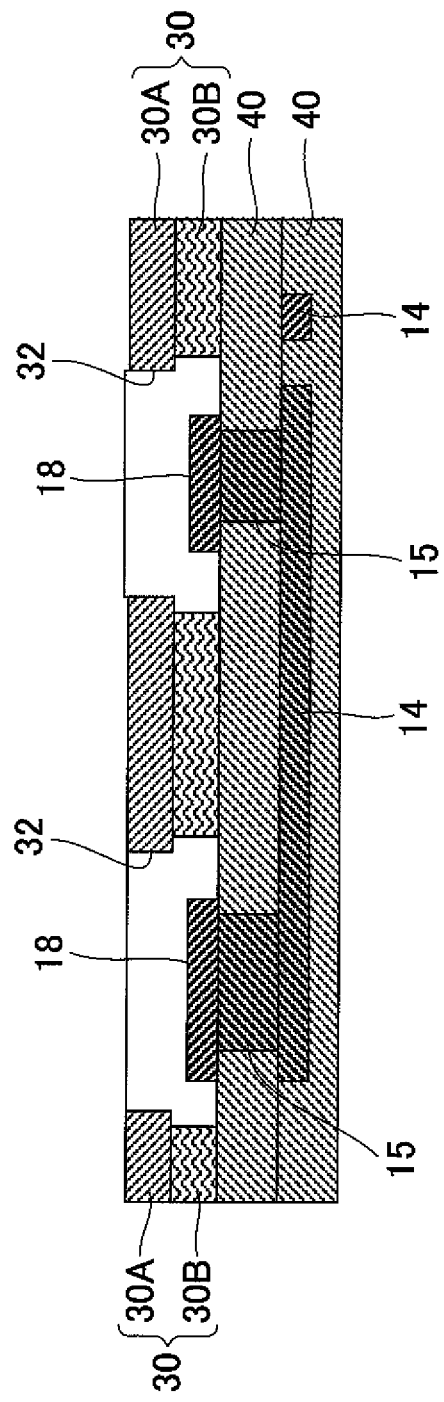
FIG. 10 is a cross-sectional view illustrating the state where only an electrode is exposed from the surface and an extending wiring line is formed in the substrate.
Figure 11:
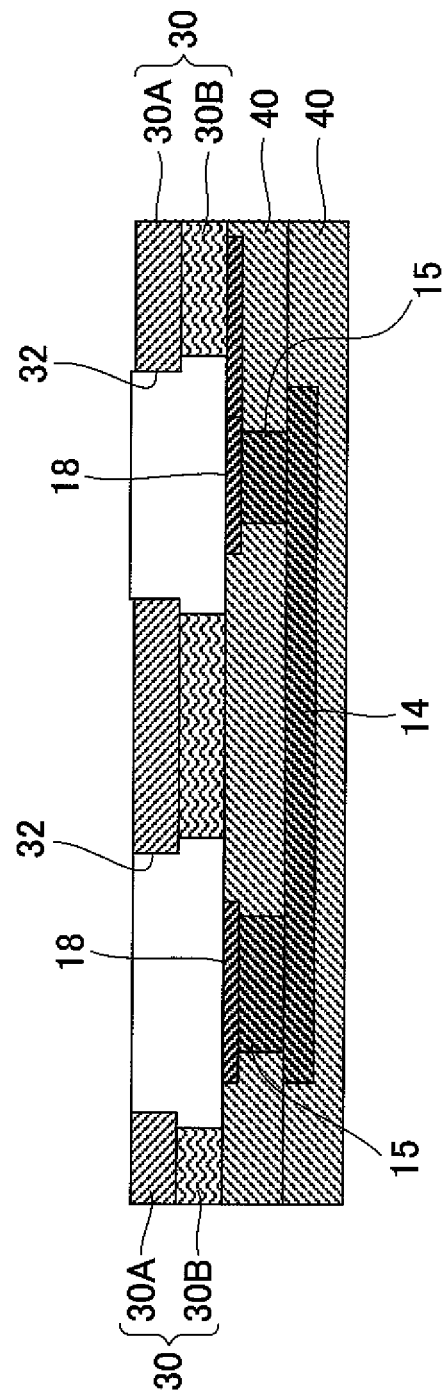
FIG. 11 is a cross-sectional view illustrating the state where the electrode and the extending wiring line are transferred (buried) into the substrate.
Figure 12:
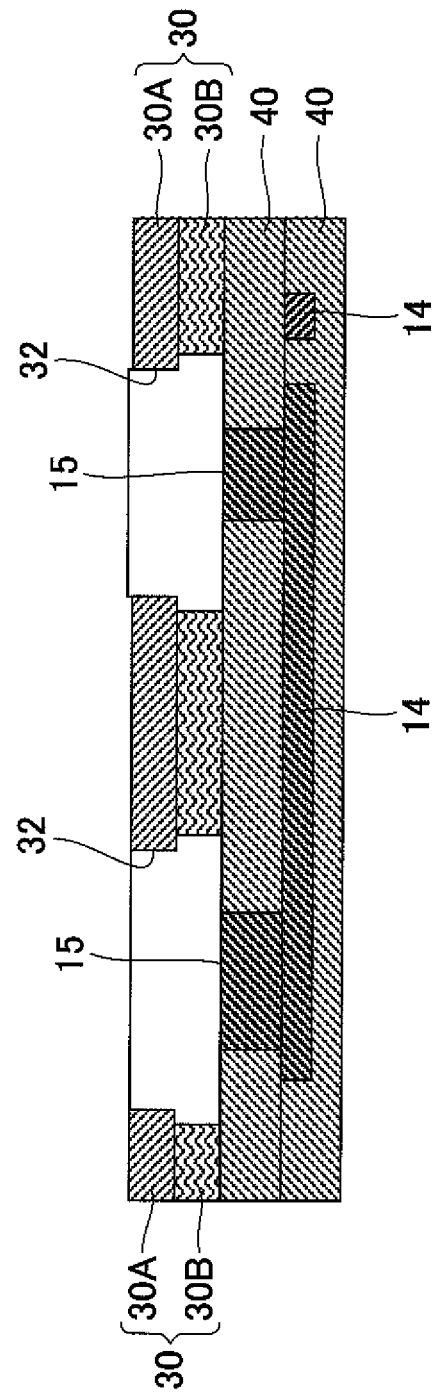
FIG. 12 is a cross-sectional view illustrating the case in which the surface of a conductor for buried connection directly serves as an electrode.

It is preferable that gold be coated on at least a portion of the outermost surface of at least one of the first electrode, the second electrode, and the third electrode, specifically, the working electrode and/or the counter electrode. This is for the following reasons. That is, when etchback is performed, a tapered portion of the extending wiring line connected to the electrode portion or an exposed portion of the extending wiring line is formed. When the coverlay is coated and a substrate is formed by gold plating, a copper wiring line is exposed. This may cause a change in copper ions during analysis and the cutting of the wiring line during analysis. Therefore, it is preferable to perform gold plating before the coverlay is coated. It is preferable to perform direct gold plating as the gold plating. It is more preferable to perform nickel/gold plating as the gold plating, and it is most preferable to perform nickel/palladium/gold plating as the gold plating. In this case, it is possible to prevent the production of an alloy due to the mutual diffusion of gold and copper and the formation of an oxide film on the surface electrode. Therefore, it is possible to maintain the surface of a gold electrode in a stable pure gold state. According to the invention, after a copper wiring line is formed, a carbon film may be formed on the copper pattern before the coverlay is coated or the copper pattern in an exposed portion of the electrode after the coverlay is coated. In the invention, a carbon including layer may be provided on the surface of the copper wiring line plated with gold, and a pure gold electrode may be provided on the carbon including layer by gold vapor deposition, considering the case in which the extending wiring line is disposed on the same surface as the electrode surface. However, in this case, the exposure of a gold-plated portion that is not covered with the carbon including layer is likely to prevent analysis. Therefore, as shown in FIG. 10, it is preferable that only the surface of an electrode 18 be exposed and at least the extending wiring line 14 be formed inside the insulating substrate 40. When the extending wiring line 14 is formed so as to extend from the surface to an inner layer and is then drawn to a surface layer, the structure in which the surface wiring line and the electrode are transferred into the insulating substrate 40 is effective in preventing the infiltration of the adhesive layer 30B in the clearance portion and the prevention of a current leakage between the extending wiring lines. Therefore, the cross-sectional structure shown in FIG. 11 is preferable. More preferably, as shown in FIG. 12, the surface of a conductor 15 for buried connection serves as a direct electrode, in terms of a reduction in the size of the electrode or a reduction in the number of processes. In addition, the surface of the conductor for buried connection may serve as a connector connection portion in addition to a direct measuring electrode (the working electrode, the reference electrode, or the counter electrode). The measuring electrode group and the connector connection portion are not necessarily formed in the same plane, but may be disposed on the front and rear surfaces. In this case, it is possible reduce the load of the mask design during vapor deposition. In this structure, particularly, in the structure in which the wiring lines or the electrodes are buried, a multi-layer wiring layer may be manufactured by techniques related to WO/2003/056889. In addition, a laser beam drilling method or a build-up method using filled copper plating that has generally been known may be used.

The structure has been described in which the uppermost surface is coated with gold and the carbon including layer is provided as the base layer thereof. However, the base layer of the uppermost layer may be a nickel layer or a palladium. In this case, the same effects as described above are obtained.

Figure 13:
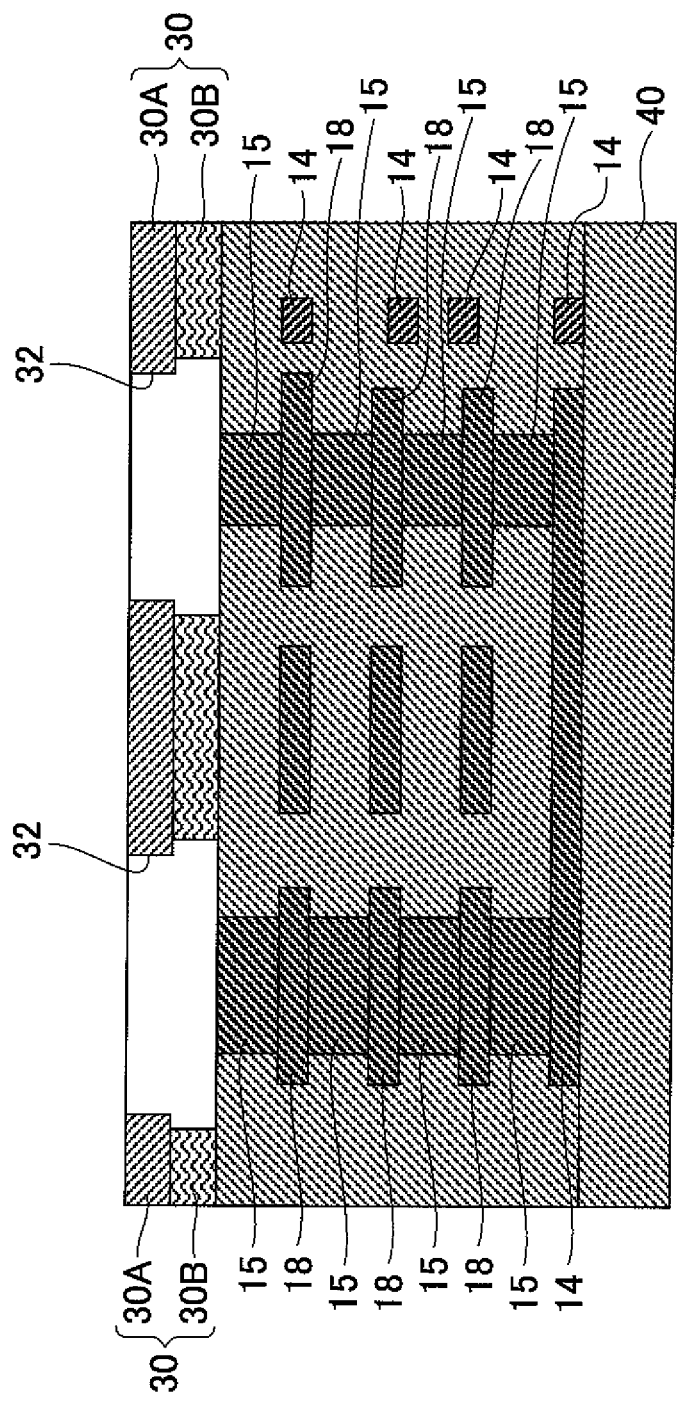
FIG. 13 is a diagram illustrating a structure in which the surface of the conductor for buried connection is arranged at least on a connector connection portion other than the outermost direct measuring electrode.
Figure 14:
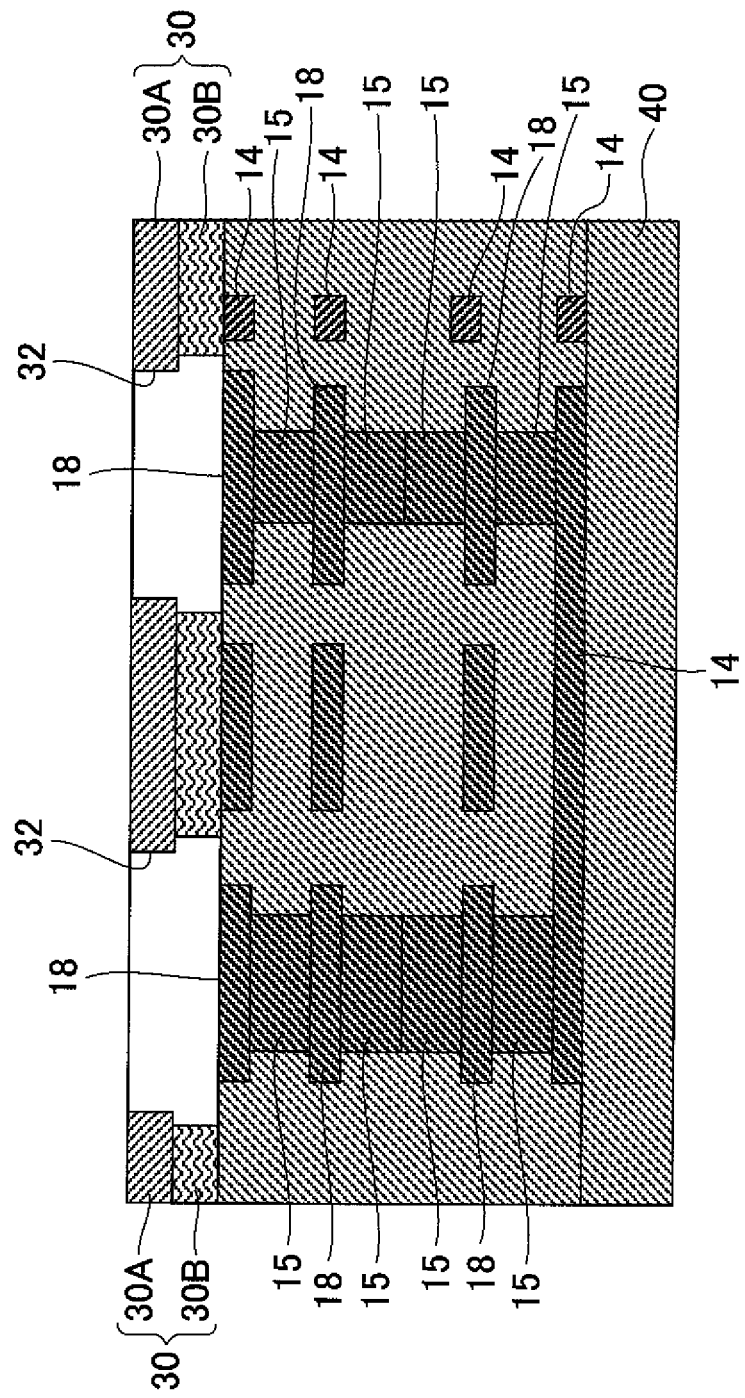
FIG. 14 is a diagram illustrating a structure in which the surfaces of connection conductors of a substrate for connection used to arrange a transfer wiring line on the connector connection portion other than a measuring electrode face each other.

FIGS. 13 and 14 show an example of the multi-layer wiring line. As the structure in which the surface of the conductor 15 for buried connection is arranged at least on the connector connection portion in addition to the measuring electrode arranged on the uppermost surface, as shown in FIG. 13, the surface of the conductor 15 for buried connection that is exposed by polishing a connection substrate may be arranged. In FIG. 13, the interface between the conductor 15 for buried connection and the electrode 18 (when the conductor 15 for buried connection is disposed on the upper side and the electrode 18 is disposed on the lower side) has a laminated structure of copper/nickel/copper, and the uppermost surface of the conductor 15 for buried connection is a direct gold surface, and the interface between the conductor 15 for buried connection and the electrode 18 (when the conductor 15 for buried connection is disposed on the lower side and the electrode 18 is disposed on the upper side) is a bonded surface of direct gold and direct gold.

In order to arrange a transfer wiring line in the connector connection portion in addition to the measuring electrode, as shown in FIG. 14, the surfaces of the conductors 15 for connection of the connection substrate may face each other. In FIGS. 13 and 14, substantially the same components as those shown in FIGS. 4 to 12 are denoted by the same reference numerals.

In FIGS. 13 and 14, a coverlay film 30A (polyimide) with an adhesive layer 30B as shown in the drawings may be used for coating the coverlay 30. In addition, the entire insulating substrate may be made of a liquid crystal polymer, the coverlay may be also made of the liquid crystal polymer, portions of the insulating substrate and the coverlay may be removed and recessed by a router apparatus in advance, and the insulating substrate and the coverlay may be laminated to each other and then bonded to each other by a vacuum press at a temperature of 250° C. to 300° C. for 5 minutes. That is, the entire insulating substrate may be made of a liquid crystal polymer. Alternatively, two coverlays may be prepared, and openings may be formed in the coverlays such that the diameter of the opening in the upper coverlay is less than that of the opening in the lower coverlay. The recession structure manufactured in this way and the structure to which the formation of the carbon including layer is applied is substantially the same as the structure shown in FIGS. 8 and 9. After the coverlays are prepared, openings may be collectively formed in the upper coverlays and the lower coverlays by drilling. Therefore, it is possible to significantly improve productivity, as compared to a chemical process. As such, the substrate in which the coverlay has the recession structure and the carbon including layer is formed on at least the electrode may be used as a mounting substrate.

(Organic Monolayer)

It is preferable that an organic monolayer be formed on at least a portion of the uppermost surface of the working electrode in order to improve the sensitivity or selectivity of a sensor and improve the flowability or durability of the surface, as compared to the structure in which the electrode is exposed.

It is preferable that an organic molecular film having a substituent group including at least one selected from the group consisting of chlorine, bromine, sulfur, nitrogen, and oxygen on the surface thereof be used as the organic monolayer. Specifically, any of the following organic monolayers may be used: an organic monolayer having a substituent group including olefin, calboxylic acid, amine, amide, or pyrrole formed on gold; and an organic monolayer in which organic molecules having the above-mentioned substituent group are bonded to each other on carbon by covalent bonding. Among the organic monolayers, the organic monolayer having the substituent group including olefin or pyrroles is preferable.

In order to form the organic monolayer, any of the following methods is used: a method using a gold-sulfur covalent bonding reaction of gold and thiol or disulfide; and a method of covalently bonding chalcogen of, for example, sulfur or oxygen, or nitrogen or carbon to the surface in which halogen of bromine or chlorine is introduced to carbon. These films are immersed in a solution and are formed by a self-organized reaction with gold.

<Sensor System>

Next, a sensor system according to the invention will be described. The sensor system according to the invention includes the sensor according to the invention, a measuring device that measures voltage-current characteristics between at least two electrodes among the electrodes of the sensor, that is, a measuring device that quantitatively measures (analyzes) analysis information from the sensor, a connector and a wiring member (which are optional) that electrically connect the sensor and the measuring device, a pre-processing unit that neutralizes or filters a liquid to be analyzed or makes the liquid hardly soluble, and an analysis liquid container for the pre-process.

As the measuring device in the sensor system according to the invention, a measuring device for cyclic voltammetry may be used. In addition, the connector, the wiring member, and the analysis liquid container are not particularly limited, but those generally used in this technical field may be used. The pre-processing unit will be described below.

<Portable Sensor System>

A portable sensor system according to the invention includes at least the sensor according to the invention, a measuring device that measures voltage-current characteristics between at least two electrodes among the electrodes of the sensor, and a portable container that accommodates at least the sensor and the measuring device.

In the portable sensor system according to the invention, connectors and wiring lines for electrically connecting the sensor and the measuring device are accommodated in the portable container, and the portable sensor system is handy to carry. In addition, it is possible to improve user convenience.

Figure 41:
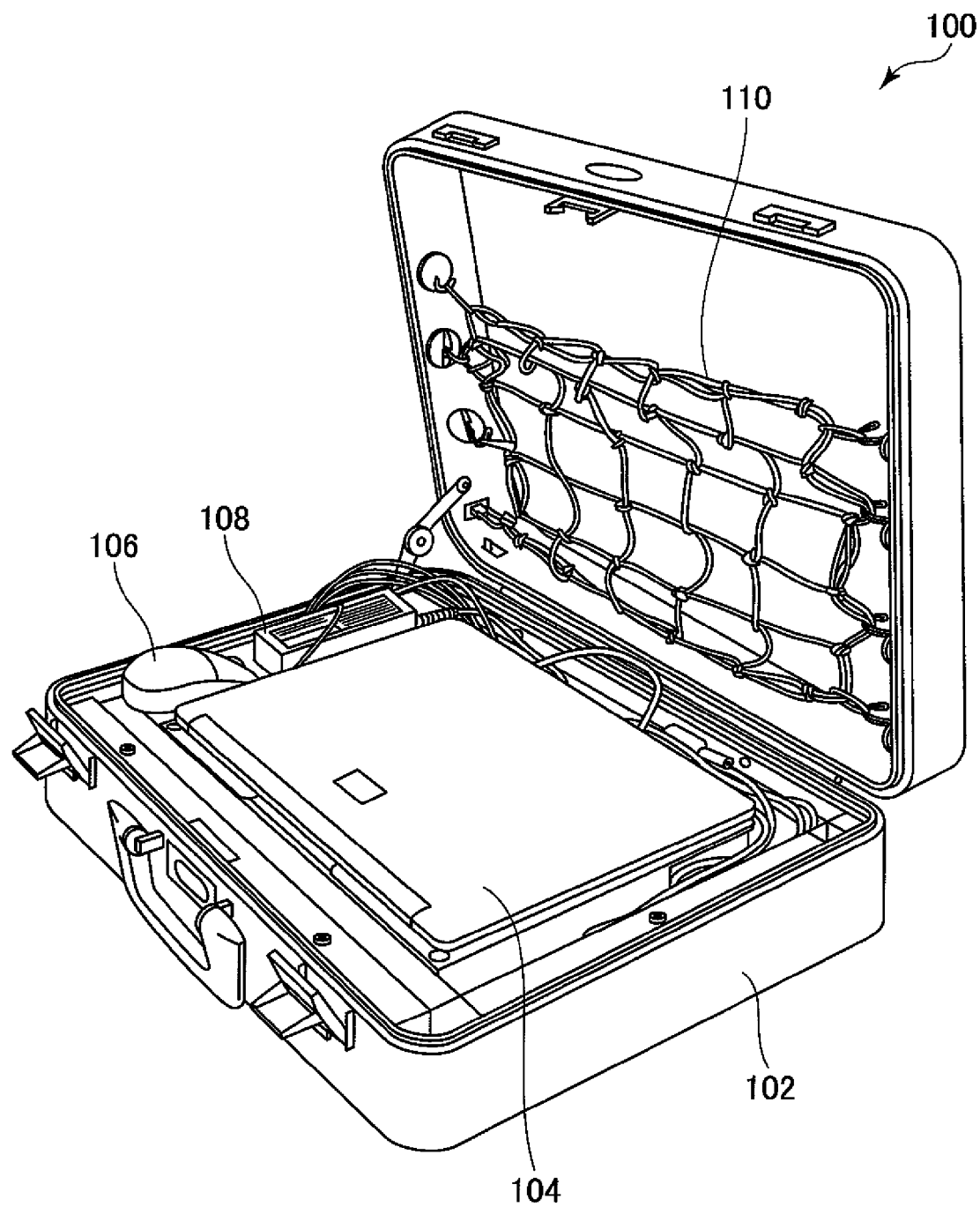
FIG. 41 is a perspective view illustrating an example of a portable sensor system according to the invention.

FIG. 41 is a perspective view illustrating an example of the portable sensor system according to the invention. A portable sensor system 100 shown in FIG. 41 is an example in which a portable trunk case 102 is used as a portable container. The trunk case 102 includes a main body and a cover that is hinged to the main body so as to be openable. FIG. 41 shows the opened state of the trunk case 102. The main body of the trunk case 102 accommodates, for example, a notebook personal computer 104 that processes instruction signals and data from a measuring device, a mouse 106, an AC adapter 108, and cables. The measuring device is provided below the notebook personal computer. In addition, a small object accommodating pocket 110 is provided inside the cover, and the small object accommodating pocket 110 accommodates a sensor substrate, a controller for controlling the electrochemical measurement of the measuring device (which is software backup and is installed in the notebook personal computer), connectors and wiring lines, materials required for measurement (small objects: for example, gloves and an eye protector), and additives used for analysis (for example, a silver nitrate solution). The trunk case 102 is designed such that, when the cover is closed, the small object accommodating pocket 110 having small objects accommodated therein does not come into contact with the notebook personal computer 104. In addition, a space for accommodating the measuring device is provided below the notebook personal computer, and an insulating material and/or a shock absorber absorb vibration when the portable sensor system is carried. In addition, heat dissipation during measurement is also considered.

When the portable sensor system 100 is carried to a measurement place and measurement is performed, the trunk case 102 is opened, and the sensor substrate, the measuring device, the controller for controlling the electrochemical measurement of the measuring device, the connectors, and the wiring lines accommodated in the small object accommodating pocket 110 are taken out. The notebook personal computer 104, the measuring device, and the sensor substrate are connected to each other by the connectors and the wiring lines. The notebook personal computer 104 may be taken out from the main body and then used, or it may be used while being accommodated in the main body. It is difficult to use the AC adapter 108 in the place where domestic power is not available. The notebook personal computer 104 may be operated by a built-in battery and the built-in battery may supply power to the measuring device. In this case, instructions are transmitted from software to the measuring device and the notebook personal computer 104, and data is transmitted therebetween through a USB interface. Power is supplied from the USB interface.

That is, in the portable sensor system 100, all components required for measurement are accommodated in trunk case 102, and the portable sensor system 100 can be freely carried when the cover of the trunk case 102 is closed. Therefore, it is possible to carry the portable sensor system 100 to any desired place and freely perform measurement. In FIG. 41, the trunk case is given as an example of an accommodating container, but the invention is not limited thereto. For example, any case may be used as long as it can be carried while accommodating the components. The sensor system according to the invention is a total of about 8 kg in a standard system structure. In the portable sensor system according to the invention, it is possible to significantly reduce the weights of the trunk case, the notebook personal computer, and the measuring device. Therefore, it is possible to significantly reduce the weight of the portable sensor system (for example, 2 kg or less).

The portable sensor system according to the invention is different from the related art in that the sensor system according to the invention is portable. The description of the measuring device described in the sensor system according to the invention, or the description of an analysis method using the sensor system according to the invention is appropriate as the description of the portable sensor system according to the invention. Therefore, the portable sensor system according to the invention can acquire desired data in a measurement place during measurement and analysis by the sensor system according to the invention.

(Pre-Processing Unit)

Next, for example, a pre-processing unit for quantitatively analyzing a monovalent copper chemical species will be described, but the invention is not limited thereto. Various modifications and other aspects of the invention can be made within the scope and spirit of the invention.

When the monovalent copper chemical species is quantitatively analyzed, it is an important technique to pre-process a mixture thereof in various ways.

Figure 15:
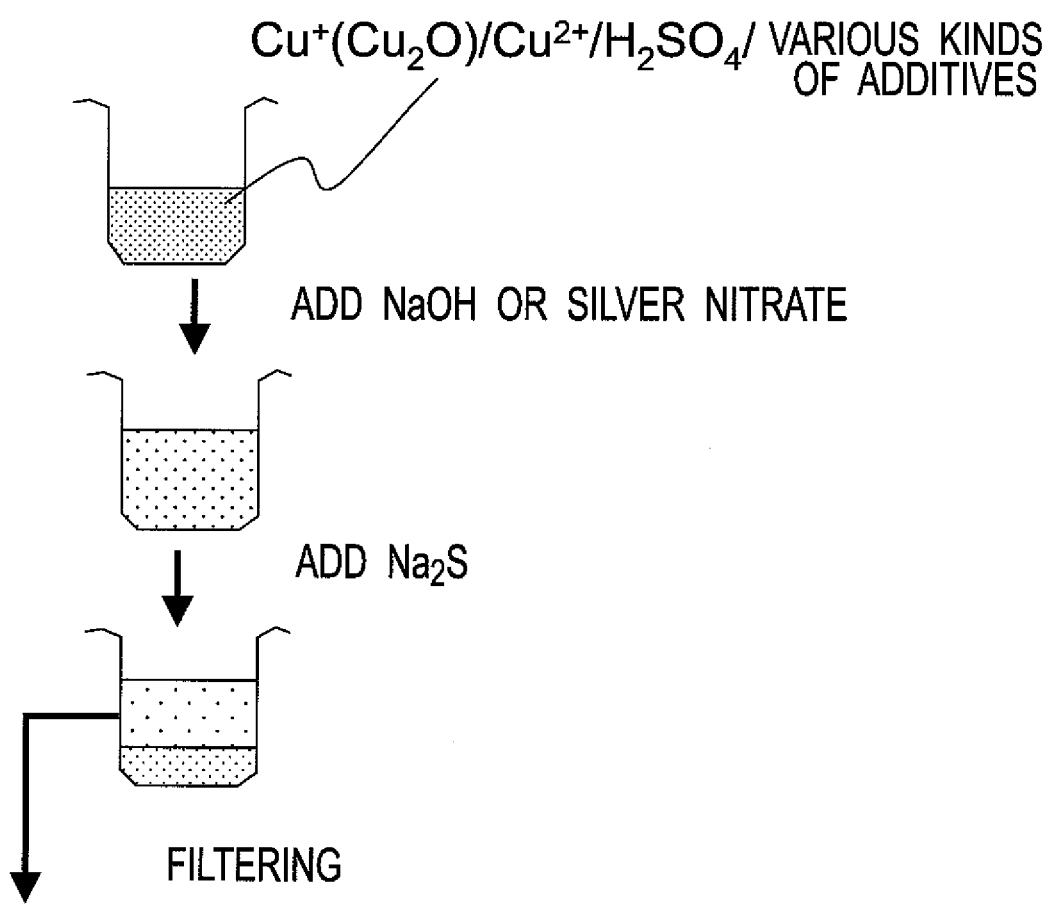
FIG. 15 is a diagram schematically illustrating a method of extracting monovalent copper ions by making copper sulfide hardly soluble with sodium sulfide after a neutralizing process with sodium hydroxide is performed.
Figure 16:
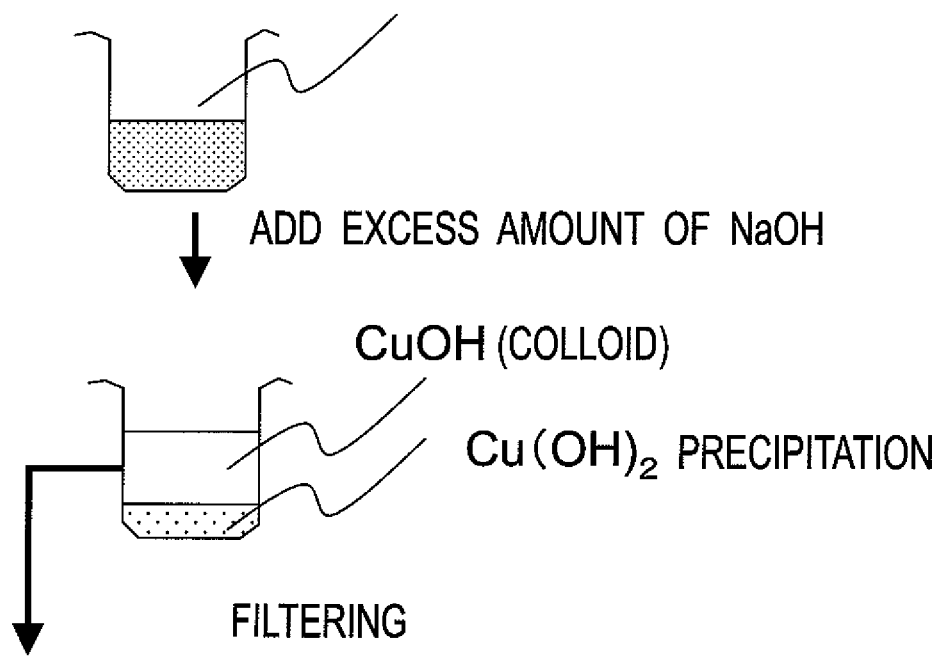
FIG. 16 is a diagram schematically illustrating a method of making copper hydroxide hardly soluble with excess sodium hydroxide.

In order to perform a chemical pre-process, two kinds of cooper sulfate ($CuSO_4$) shown in FIGS. 15 and 16 have been considered. That is, as shown in FIG. 15, as one method, after a neutralizing process is performed with sodium hydroxide, a process of making cooper sulfide hardly soluble with sodium sulfide is performed to extract monovalent copper ions. As shown in FIG. 16, another method is to make copper hydroxide hardly soluble with excessive sodium hydroxide. The obtained solid is filtered by cotton or an appropriate porous filter, and the filtering solution is analyzed in each step, which will be described below, to detect the amount of monovalent copper ions while reducing the influence of an excess amount or a very small amount of analysis preventing material in a mixture.

Figure 17:
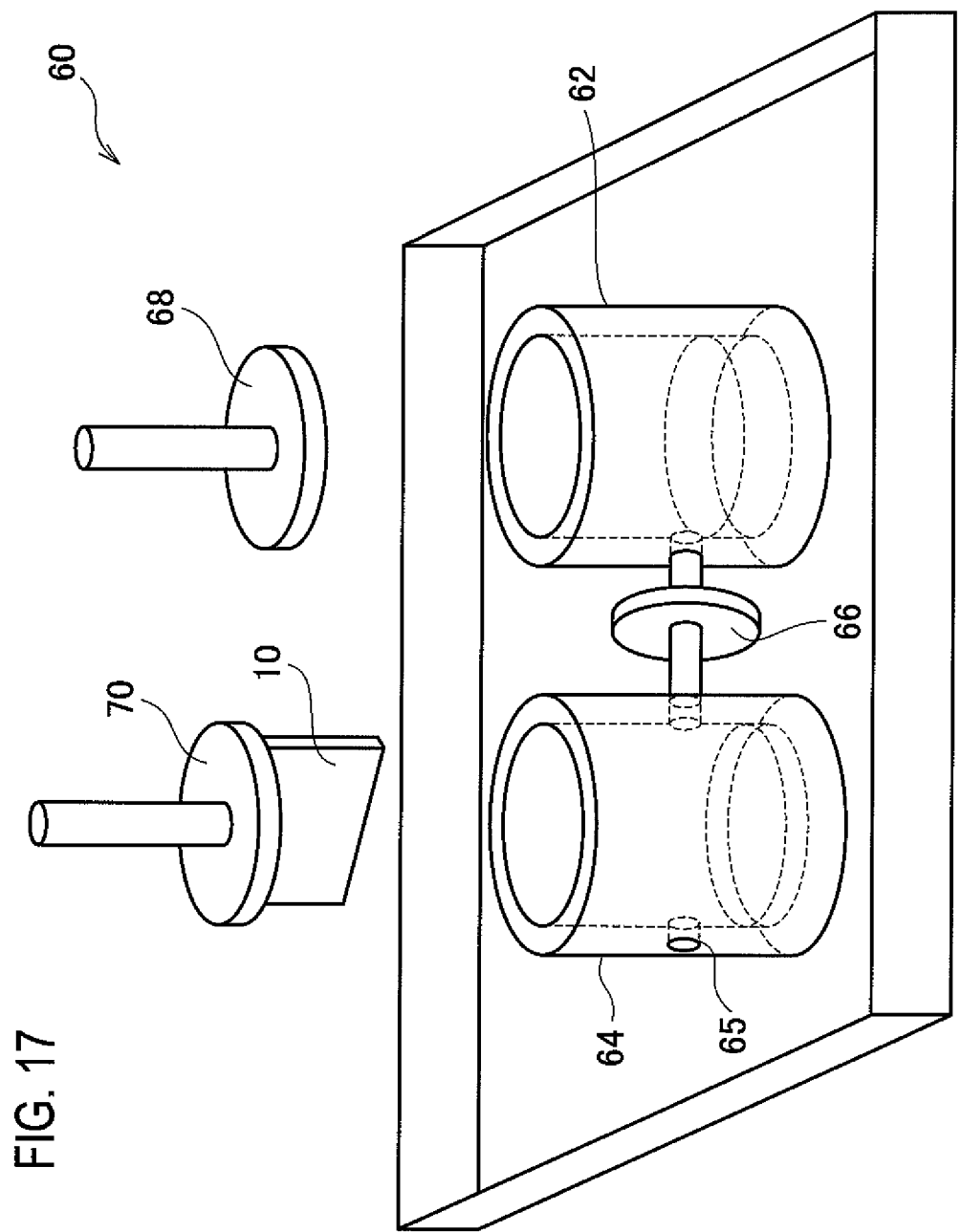
FIG. 17 is a perspective view illustrating a twin-peak kit for effectively performing a pre-process.

For example, a twin-peak kit shown in FIG. 17 may be used for filtering. The twin-peak kit is made of a polypropylene resin with high heat resistance.

The twin-peak kit shown in FIG. 17 has the following structure. A cylinder 62, which is an analysis liquid container, is a container into which a liquid to be analyzed is introduced and then a neutralizing agent and an agent for making the liquid hardly soluble are introduced, or a container into which an encapsulated neutralizing agent and an encapsulated agent for making the liquid hardly soluble are introduced. A piston 68 is pressed after the liquid to be analyzed introduced into the cylinder 62, which is an analysis liquid container, reacts and transmits the liquid to the filter 66. The piston 68 may have an additional function of breaking capsules, if necessary. The liquid filtered by the filter 66 flows into the cylinder 64, which is an analysis liquid container, and a piston 70 with a sensor 10 is pressed. An air hole 65 is an air outlet for preventing the inverse current of the liquid.

In the twin-peak kit shown in FIG. 17, the filter unit may be omitted and two individual cylinders may be used, which is a simple structure. FIG. 18(A) is a perspective view illustrating the structure. In the kid shown in FIG. 18(A), pockets (concave portions) for mounting two cylinders are provided in the bottom of a tray 94, which is a temperature-controlled tank. In FIG. 18(A), cylinders 90 and 92 are provided in the pockets. As shown in FIG. 18(B), two cutouts 90A are provided in the inner wall of the cylinder 90 so as to extend to the bottom, and the sensor substrate 10 is provided such that both ends thereof are fitted and fixed to the two cutouts 90A. Although not shown in the drawings, the cutouts are provided in the cylinder 92.

Figure 42:
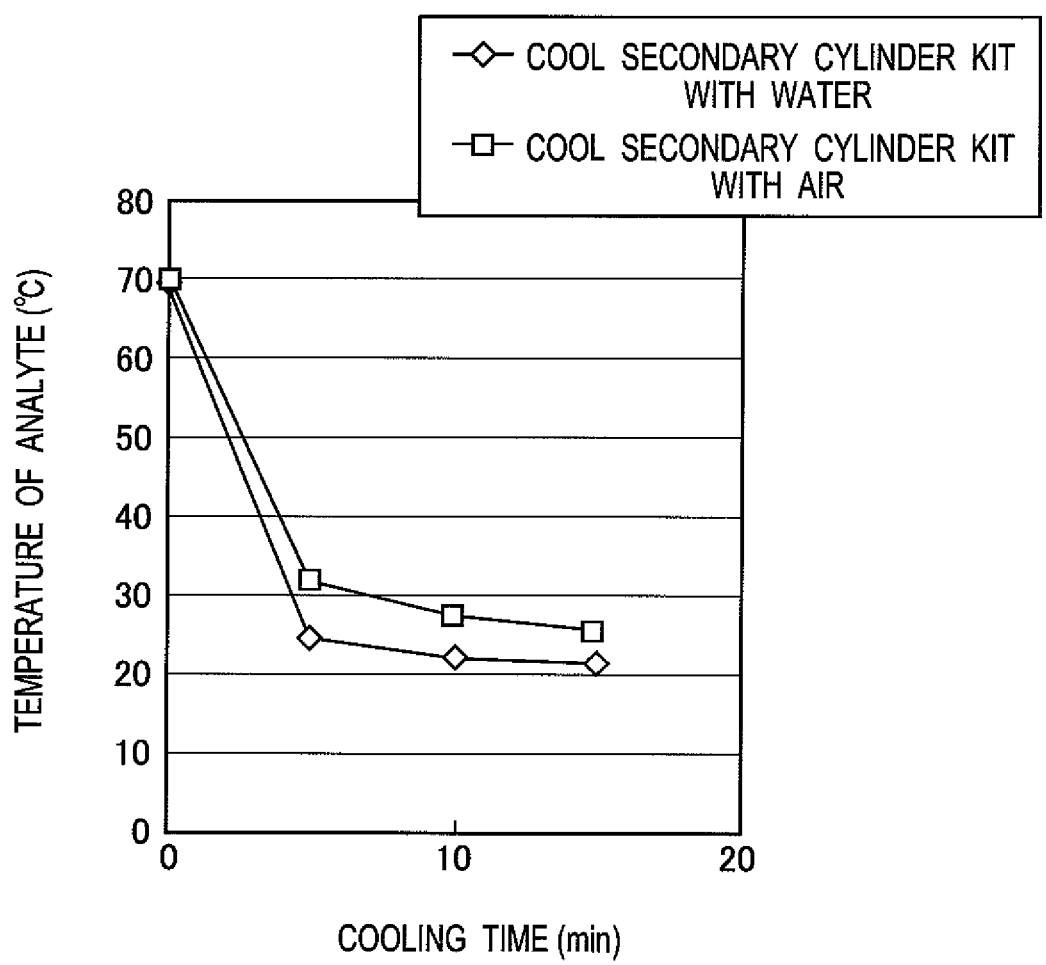
FIG. 42 is a graph illustrating a variation in the temperature of an analyte over time when the twin-peak kit shown in FIG. 18 is used to cool the analyte contained in a cylinder with cold water and when the analyte contained in the cylinder is not cooled.

The tray 18 has a tank shape and can be filled up with a liquid, for example, cold water to cool the mounted cylinders. Therefore, for example, when the cylinder is filled up with a plating solution at a relatively high temperature, the cylinder can be rapidly cooled to a temperature range in which there is little temperature variation over time by the cold water in the tray 18. FIG. 42 is a graph illustrating a variation in the temperature of an analyzing solution over time when the kit shown in FIG. 18 is used to cool the analyzing solution in the cylinder and when the analyzing solution in the cylinder is not cooled. As can be seen from the comparison between when the analyzing solution is cooled and when the analyzing solution is not cooled in FIG. 42, the time required to reach 25° C.

where there is little temperature variation over time in the former is 5 minutes, which is half the time required to reach 25° C. in the latter. Therefore, it is possible to reduce the waiting time to analysis. In FIG. 18, two cylinders are provided, but the number of cylinders is not limited thereto. Any number of cylinders may be provided. In addition, a cooling medium is not limited to the cold water, but other cooling media may be used.

In the following examples, this kit is appropriately used.
<Method of Analyzing Metal Ions>

Next, a method of analyzing metal ions according to the invention will be described. As the method of analyzing metal ions, there are the following two aspects: an aspect that uses the above-mentioned sensor system to directly analyze a liquid to be analyzed without performing a pre-process; and an aspect that performs a pre-process to analyze a liquid to be analyzed.

In the latter aspect that performs the pre-process to analyze the liquid to be analyzed, preferably, any of the following methods is used: (1) a method of neutralizing and filtering a liquid to be analyzed and analyzing the liquid to be analyzed using a colorimetric method; (2) a method of neutralizing and filtering a liquid to be analyzed and analyzing the liquid to be analyzed using an electrochemical method or a surface potential measuring method; (3) a method of neutralizing a liquid to be analyzed, making the liquid to be analyzed hardly soluble, filtering the liquid to be analyzed, and analyzing the liquid to be analyzed using the electrochemical method or the surface potential measuring method; (4) a method of making a liquid to be analyzed hardly soluble, filtering the liquid to be analyzed, and analyzing the liquid to be analyzed using the electrochemical method or the surface potential measuring method; and (5) a method of making a liquid to be analyzed hardly soluble and analyzing the liquid to be analyzed using the electrochemical method or the surface potential measuring method.

The method of neutralizing the liquid to be analyzed and making the liquid to be analyzed hardly soluble has been described with reference to FIGS. 15 and 16.
(Calorimetric Method)

Next, for example, the colorimetric method for analyzing a monovalent copper chemical species will be described, but the invention is not limited thereto. Various modifications and other aspects of the invention can be made within the scope and spirit of the invention.

When the monovalent copper chemical species is quantitatively analyzed, it is an important technique to quantitatively determine whether there is a monovalent copper chemical species in a mixture to be analyzed based on a variation in the color of the mixture.

Figure 19:
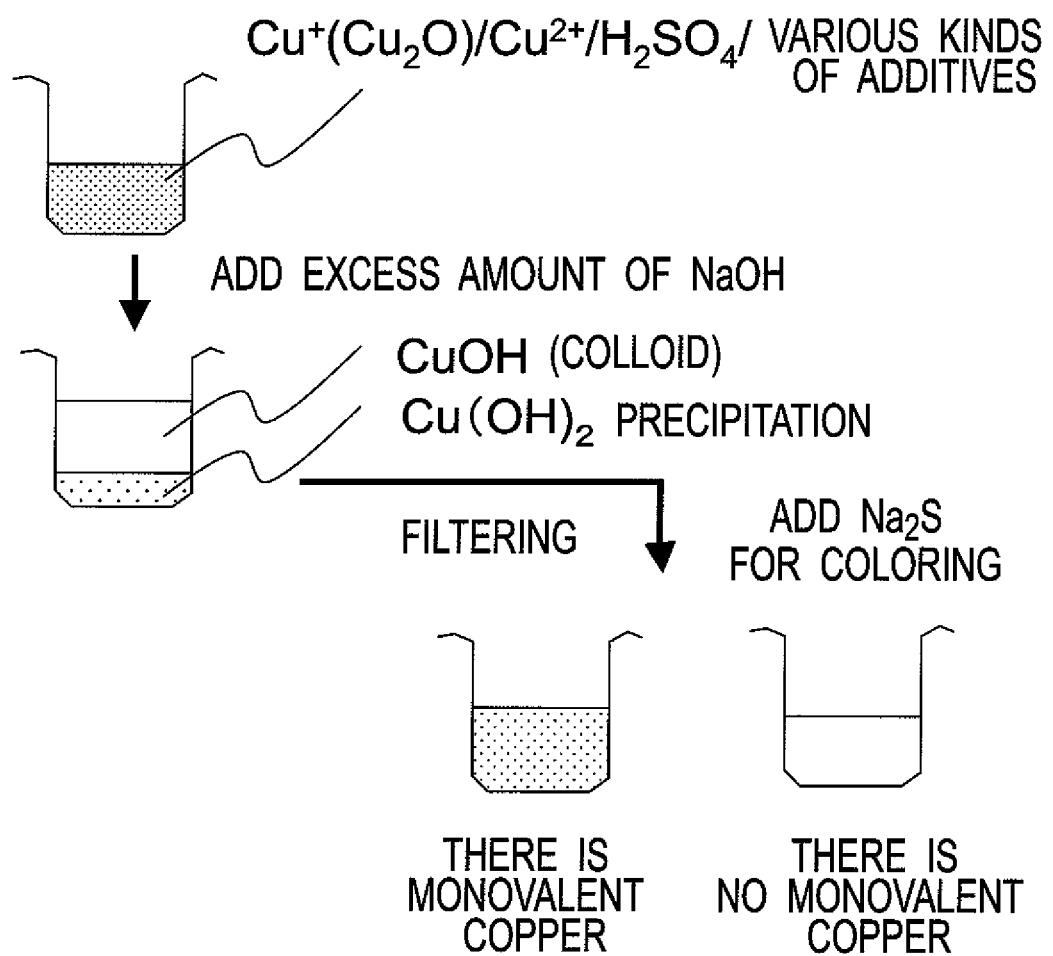
FIG. 19 is a diagram illustrating a colorimetric technique for analyzing monovalent copper ions.

As shown in FIG. 19, an acid solution of copper sulfate ($CuSO_4$) including 0.1 to 2.0 mM of monovalent copper ions is processed according to the method of making a liquid hardly soluble shown in FIG. 16 and a variation in the color thereof is checked. That is, when 4 equivalent of excess sodium hydroxide is added to the acid solution, copper sulfate ($CuSO_4$) is hardly soluble as copper hydroxide ($Cu(OH)_2$) from the solution. When the solution is filtered by cotton or a filter having porous with a diameter of about 1 μm, and sodium sulfide is added to the filtered solution. The inventors' examination proved that the colorimetric method was used to check about 1 mM of more of monovalent copper ions.
<Cyclic Voltammetry and Surface Potential Method (Electrochemical Method)>

Hereinafter, for example, an electrochemical method for quantitatively analyzing a monovalent copper chemical species will be described, but the invention is not limited thereto. Various modifications and other aspects of the invention can be made within the scope and spirit of the invention.

EXAMPLES

Example 1

Figure 20:
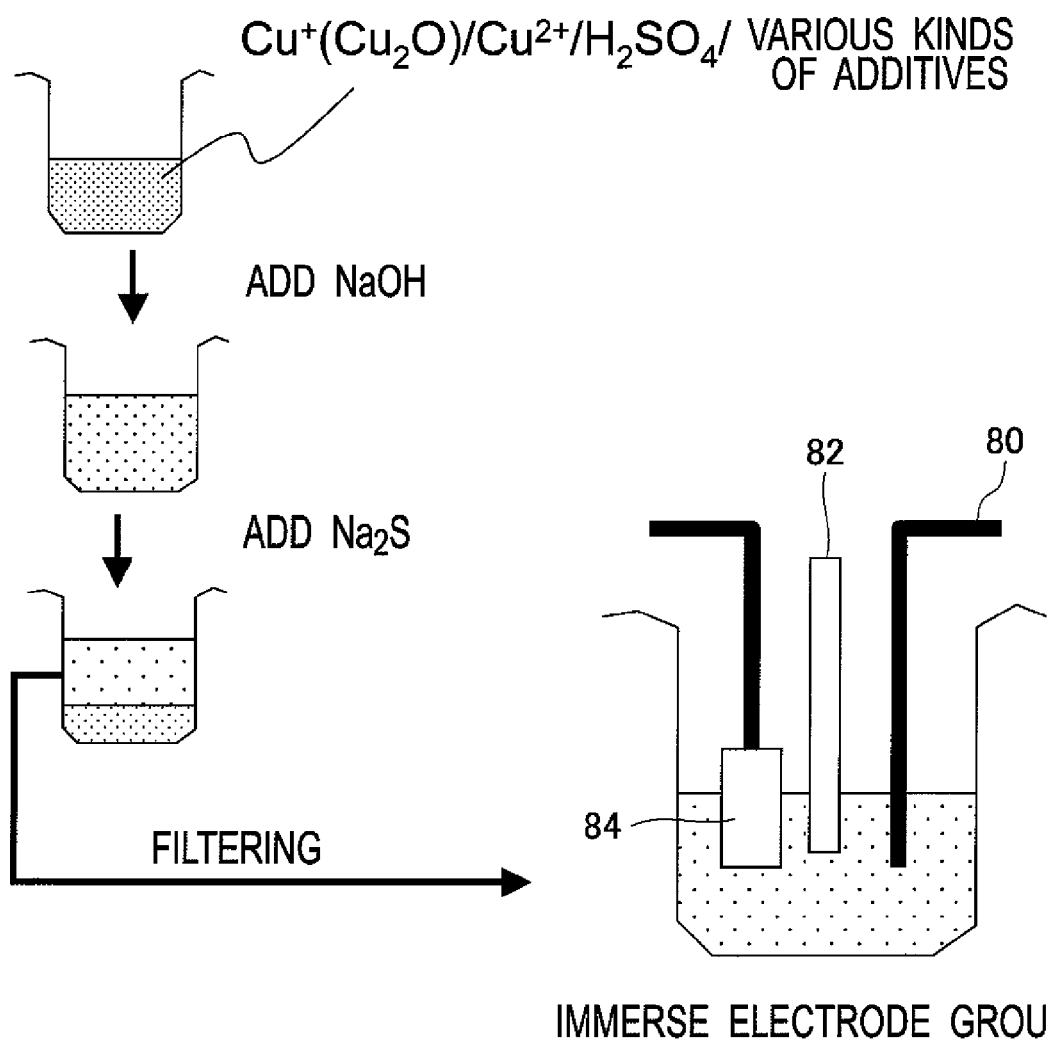
FIG. 20 is a diagram illustrating a method using cyclic voltammetry.
Figure 21:
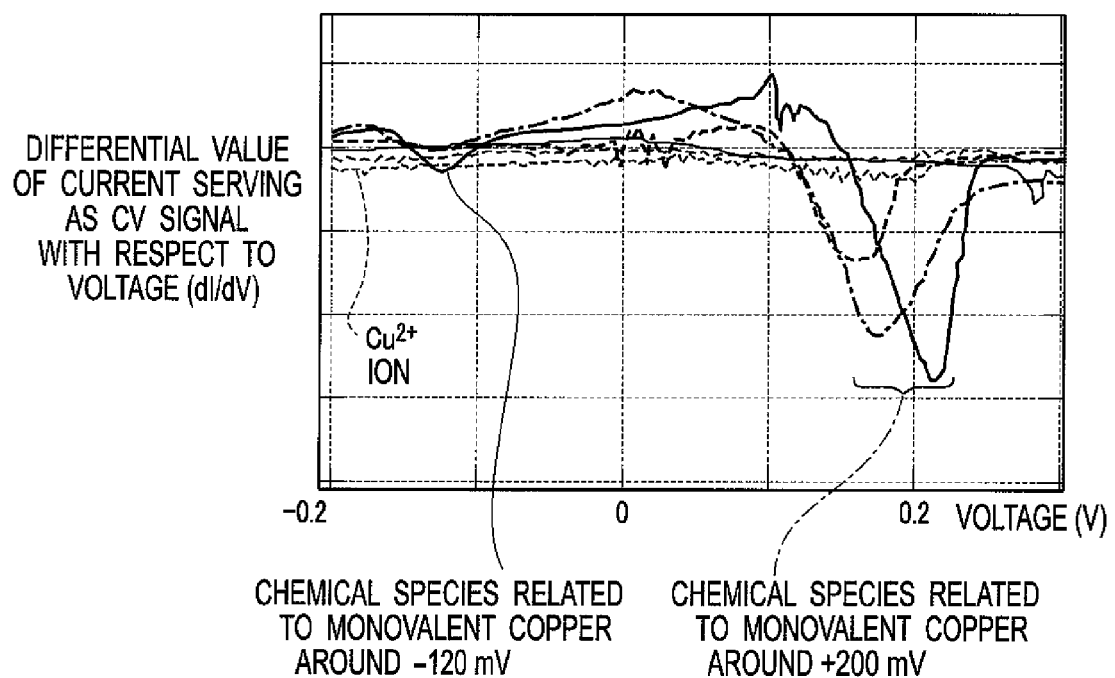
FIG. 21 is a graph illustrating data obtained by analyzing whether there is monovalent copper using the method shown in FIG. 20.

As shown in FIGS. 15 and 20, an acid solution of copper sulfate ($CuSO_4$) including about 0.1 to 10 mM of monovalent copper ions was processed to check a difference in cyclic voltammetry. That is, first, a solution was neutralized by an equivalent of sodium hydroxide and sodium sulfide was added to the neutralized solution. As a result, a blackish brown hardly soluble deposit occurred. The solution was filtered and a self-assembled film that was made of nonanedithiol and was disposed on a gold (111) plane was immersed in the obtained filtrate for two minutes. Then, the film was taken out and rinsed with 0.1 M of potassium peroxide solution once. Then, cyclic voltammetry was performed in 20 mM of potassium peroxide solution. In this case, three electrodes, that is, a silver/silver chloride electrode serving as the reference electrode, a platinum substrate with a thickness of 1 mm and a size of about 5 mm×about 10 mm, serving as the counter electrode, and a self-assembled film (area: about 0.25 m$^2$), serving as the working electrode, subjected to the above-mentioned process, were used to analyze the dependence of a current on a voltage while changing the voltage from +300 mV to −200 mV. As shown in FIG. 21, the results proved that, when the solution including only the copper sulfate ($CuSO_4$) was analyzed, the maximum value of the current or the integral value of the current was not obtained as a significant CV signal, but when there was a monovalent copper ion, the maximum value of the current or the integral value of the current was obtained as a CV signal around about −120 mV and about +200 mV according to concentration. FIG. 21 shows a graph in which the vertical axis indicates an electrochemical current value and the horizontal axis indicates the differential value of the potential of the working electrode. It is possible to quantitatively analyze the concentration of the monovalent copper ions in the copper sulfate ($CuSO_4$) solution using this method in an indirect manner.

Example 2

Figure 22:
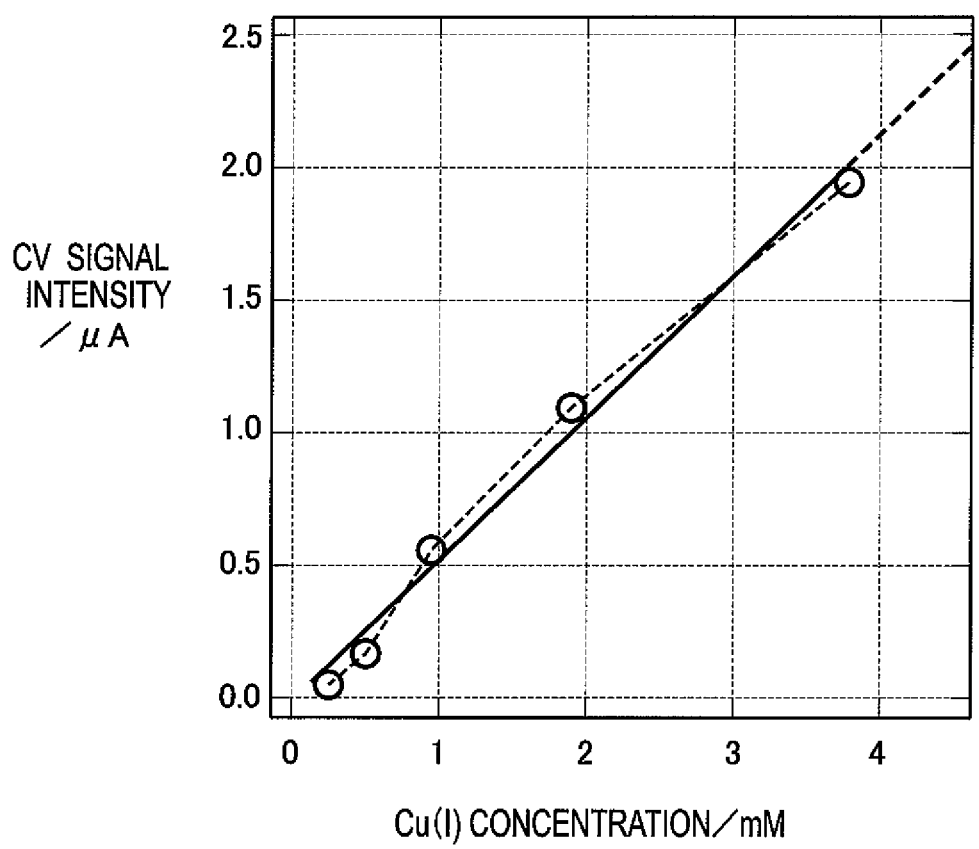
FIG. 22 is a graph illustrating the analysis result when a silver/silver chloride electrode used in electrochemistry is used as a reference electrode, Pt is used as a counter electrode, and gold is used as a working electrode.

Next, a silver/silver chloride electrode, serving as the reference electrode, that was electrochemically used was immersed in a liquid to be analyzed. A Pt electrode with a size of about 10 mm×about 10 mm, serving as the counter electrode, was immersed in the liquid to be analyzed. A square plate which had one side with a length of about 5 mm and in which gold was coated with a thickness of 500 nm on mica by vapor deposition, serving as the working electrode, was immersed in the liquid to be analyzed. The electrodes were connected to Potentiostat PGSTAT12 for cyclic voltammetry manufactured by AutoLab Instrument. An acid solution of monovalent copper ions subjected to nitrogen bubbling was added as the liquid to be analyzed to prepare a mixed acid solution of 0.2 to 3.3 mM of monovalent copper ions including an excess sulfuric acid. The three electrodes were immersed in each monovalent copper ion solution. The working electrode was swept from +0.2 V to +2.0 V and the oxidation wave thereof was observed. As a result, in this case, the maximum value of current or the integral value of current was observed as a CV signal corresponding to the monovalent copper ion around +1.15 V. FIG. 22 is a graph in which the intensity of the maximum value of current is plotted as concentration. However, since the position where the maximum value of current is observed is changed depending on the surface state of the reference electrode or the working electrode, the position is not limited to +1.15 V by a combination thereof or the usage thereof. In addition, the integral value of the current relative to the voltage may be used instead of the maximum value. This is the same as that in the following examples, and the position or range where the maximum value of the current for the analysis method or the integral value of the current is observed may be changed or other analysis aspects may be used within the technical scope of the invention. The changes are also included in the invention.

It is possible to quantitatively analyze the concentration of monovalent copper ions based on the results using this method.

Example 3

Figure 23:
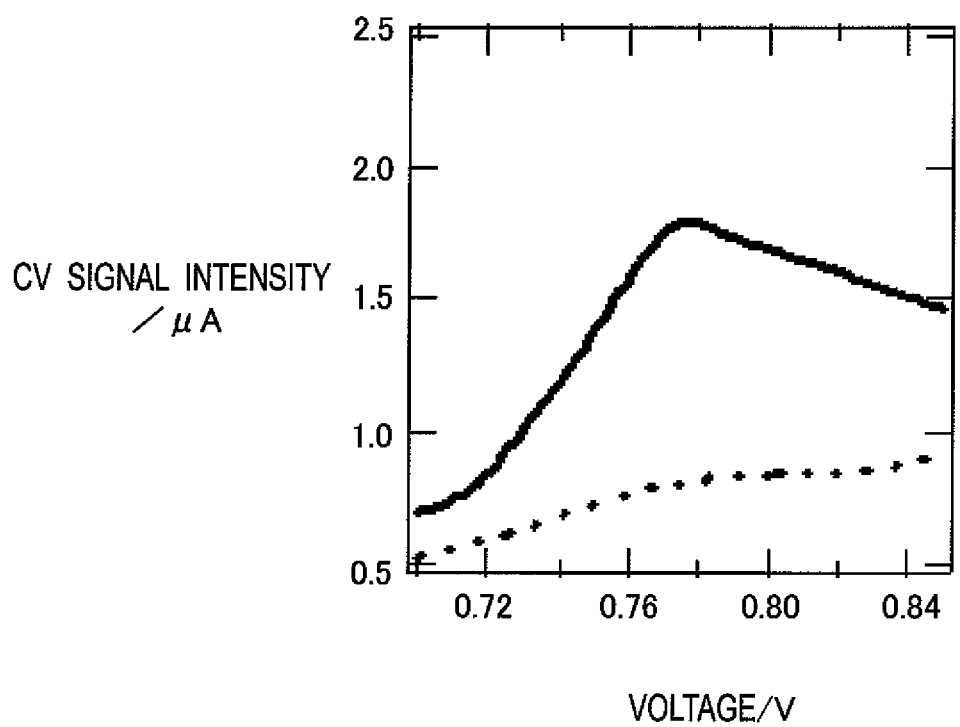
FIG. 23 is a graph illustrating the analysis result when tough carbon is used as the reference electrode, tough carbon is used as the counter electrode, and gold is used as the working electrode.
Figure 24:
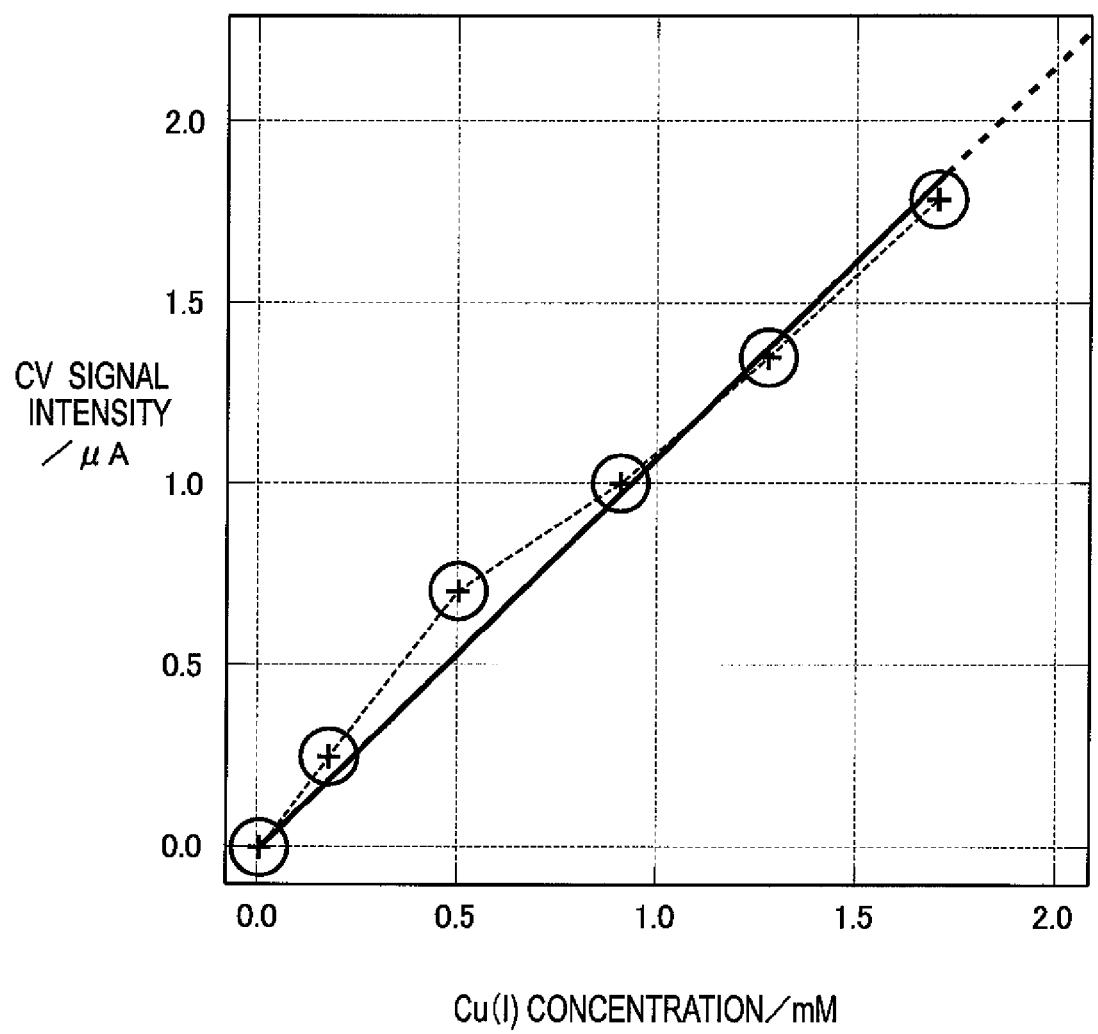
FIG. 24 is a graph illustrating the analysis result when tough carbon is used as the reference electrode, tough carbon is used as the counter electrode, and gold is used as the working electrode, which is different from the graph shown in FIG. 23.

Next, a square plate which had one side with a length of about 5 mm and in which tough carbon was coated with a thickness of 100 nm on a glass epoxy resin substrate by vapor deposition, serving as the reference electrode, was immersed in a liquid to be analyzed. A rectangular plate with a size of about 10 mm×about 10 mm in which tough carbon was coated with a thickness of 100 nm on a glass epoxy resin substrate by vapor deposition, serving as the counter electrode, was immersed in the liquid to be analyzed. A square plate which had one side with a length of about 5 mm and in which gold was coated with a thickness of 500 nm on mica by vapor deposition, serving as the working electrode, was immersed in the liquid to be analyzed. The electrodes were connected to Potentiostat PGSTAT12 for cyclic voltammetry manufactured by AutoLab Instrument. An acid solution of monovalent copper ions was added as the liquid to be analyzed to an aqueous solution including about 200 mM of copper sulfate ($CuSO_4$) including about 0.5 M of sulfuric acid subjected to nitrogen bubbling, thereby preparing a mixed acid solution of 0.2 to 1.7 mM of monovalent copper ions including excess copper sulfate ($CuSO_4$). The three electrodes were immersed in each monovalent copper ion solution. The working electrode was swept from +0.2 V to +2.0 V and the dependence of current on the voltage between the electrodes was observed. As a result, the maximum value of current or the integral value of current was observed as a CV signal corresponding to the monovalent copper ion around +0.7 to 0.8 V. In this case, a value obtained by subtracting the maximum value of current or the integral value of current with respect to a voltage, which was obtained from a reference liquid including only the copper sulfate ($CuSO_4$), from the maximum value of current or the integral value of current with respect to the voltage, which was obtained from a liquid to be analyzed including the monovalent copper ions, was used. For example, as represented by a solid line in FIG. 23, the value of the current serving as the CV signal varied when the voltage of the working electrode was changed, and the absolute value of the current was the maximum at a given voltage. In the example shown in FIG. 23, the maximum value is substantially proportional to the concentration of the monovalent copper ion, which is one kind of monovalent copper chemical species to be analyzed. When a variation in the current flowing between the electrodes with respect to the voltage is small, it is possible to know the concentration of a chemical species to be analyzed based on the integral value of the current with respect to the voltage. In Example 3, for example, as shown in FIG. 23, a value obtained by subtracting the maximum value of current, which was observed around 0.78 V and was obtained from a reference liquid including only copper sulfate ($CuSO_4$) as represented by a dotted line in FIG. 23, instead of the mixed acid solution of monovalent copper ion including excess copper sulfate ($CuSO_4$), from the maximum value of current, which was a CV signal observed around 0.78 V of a mixed acid solution of 0.91 mM of monovalent ions as represented by a solid line in FIG. 23, was analyzed as the intensity of the CV signal. However, instead of the maximum value, the integral value of the current with respect to the voltage might be used. When a variation in the current flowing between the electrodes with respect to the voltage became complicated due to a plating preventing chemical species in the copper plating solution to be analyzed, which was being used, a compound produced when copper plating was used, or the interaction among a plurality of chemical species selected from monovalent copper chemical species, it was possible to know the concentration of a chemical species to be analyzed based on the integral value of the current with respect to the voltage with a specific voltage range. Since the position where the maximum value of current is observed is changed depending on the surface states of the electrodes, the position is not limited by a combination thereof or the usage thereof. In Example 3, a voltage value of 0.705 V represented by a dotted line is used as a reference value (also referred to as a base line), but the analysis method is not limited thereto. The reference values of other portions may be used. In addition, the entire CV signal curve of the reference liquid including only the copper sulfate ($CuSO_4$) before being used, which represented in the dotted line in FIG. 23, may be horizontally moved and used as a reference for analyzing the maximum value or the integral value. This is the same as that in Examples other than Example 3, and the position or range where the maximum value of the current for the analysis method or the integral value of the current is observed may be changed or other analysis aspects may be used within the technical scope of the invention. The changes are also included in the invention. FIG. 24 is a graph in which the obtained maximum value of current is plotted at each concentration of the monovalent copper ions.

According to these results, it is possible to analyze the concentration of monovalent copper ions by using the surface of a carbon material, without using the Ag/AgCl reference electrode and the Pt counter electrode according to the related art and being affected by excess sulfuric acid and excess copper sulfate ($CuSO_4$) that coexist with each other. It is possible to analyze a chemical species in the same way as described above in Examples other than Example 3.

Example 4

Next, a method of analyzing a variation in surface potential (hereinafter, referred to as OCP (Open Circuit Potential)) will be described. An Ag/AgCl electrode was used as the reference electrode, and a molecular film was formed on the gold (111) plane which had a size of 1 cm×2 cm and in which gold was coated with a thickness of 200 nm on mica to form the sensor. Potassium sulfate was used as supporting salt.

Figure 25:
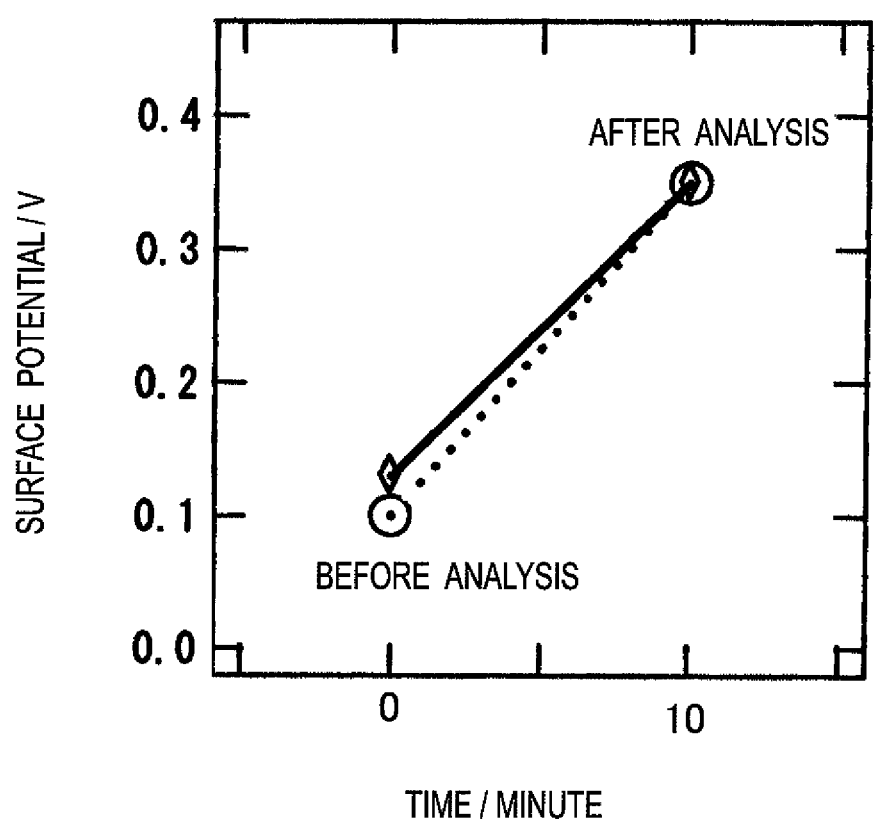
FIG. 25 is a graph illustrating a variation in surface potential before and after analysis.

A sensor in which a calboxylic acid derivative was absorbed to gold was used. A gold electrode made of a relatively inactive metal material was used as the reference electrode. The electrode had a spherical shape and the diameter thereof was in the range of about 1 mm to 3 mm. The sensor acted on copper ions with high affinity with a calboxylic acid in an aqueous solution including 0.1 M of potassium sulfate. As a result, after the action, the OCP was changed (FIG. 25). The change was relatively large before and after about 200 mV. In Example, the type of host molecule is not particularly limited, but the molecular film used in the sensor may be used as a surface potential molecular sensor as long as it can react with a specific guest molecule.

Example 5

In Example 5, the analysis of a chemical species in a plating solution will be described using the sensor substrate according to the invention, but the invention is not limited thereto. Various modifications and other aspects of the invention can be made within the scope and spirit of the invention.

In an actual copper plating solution (including 0.28 mol/L of copper sulfate, 2 mol/L of sulfuric acid, and other additives; and pH<<1), it is possible to analyze the difference between components of an initial make-up bath copper plating solution and components of the copper plating solution that is used, using the sensor substrate and the analysis method according to the invention. That is, first, 1 mL of silver nitrate aqueous solution with a concentration of 14 mmol/L was added to 10 mL of plating solution, which is an analysis target. After two minutes, a muddy liquid was filtered by a syringe filter having porous with a diameter of 0.45 μm, and the filtrate was moved to an analysis liquid container with a diameter of about 2.5 cm and a height of about 3 cm. The diameter of the porous of the syringe filter may be equal to or less than 0.45 μm. Then, the sensor substrate having a width of 17 mm and a length of 34 mm according to the invention in which the outermost surface of the electrode group arranged on the insulating organic substrate (Polyimide) shown in FIG. 1 was entirely coated with gold or partially coated with carbon was connected to the potentiostat through a connector, and the electrode group of the sensor substrate was immersed in the obtained liquid. In this case, it is necessary the liquid level does not come into contact with a connection terminal group. When the distance to the electrode or the electrode group is 1 mm or more in consideration of the meniscus effect, it is possible to avoid the contact between the liquid level and the connection terminal group. The connection terminal group is likely to come into contact with the liquid level due to the evaporation or vibration of the liquid, and noise is likely to occur during measurement. Therefore, it is preferable that the distance be 3 mm or more. It is preferable to provide a blocking plate that prevents the evaporation of a liquid including an analyte from the liquid level between the connection terminal group and the liquid level. Then, the voltage applied to the working electrode in the range of +0.2 V to +2.0 V, which was an electrochemically effective initial state, was swept at a speed of 20 mV/sec, and the dependence of a current with respect to the voltage between the electrodes was observed at a room temperature.

The term "electrochemically effective initial state" means a state where at least an oxidation wave, a reduction wave, or a combination thereof is applied before measurement starts or an operation of immersing a substrate in chemicals, such as acid, alkali, and solvent, is performed before measurement starts to remove an organic material or an oxide remaining on the surface, such that measurement can be repeatedly performed in a stable state.

Figure 26:
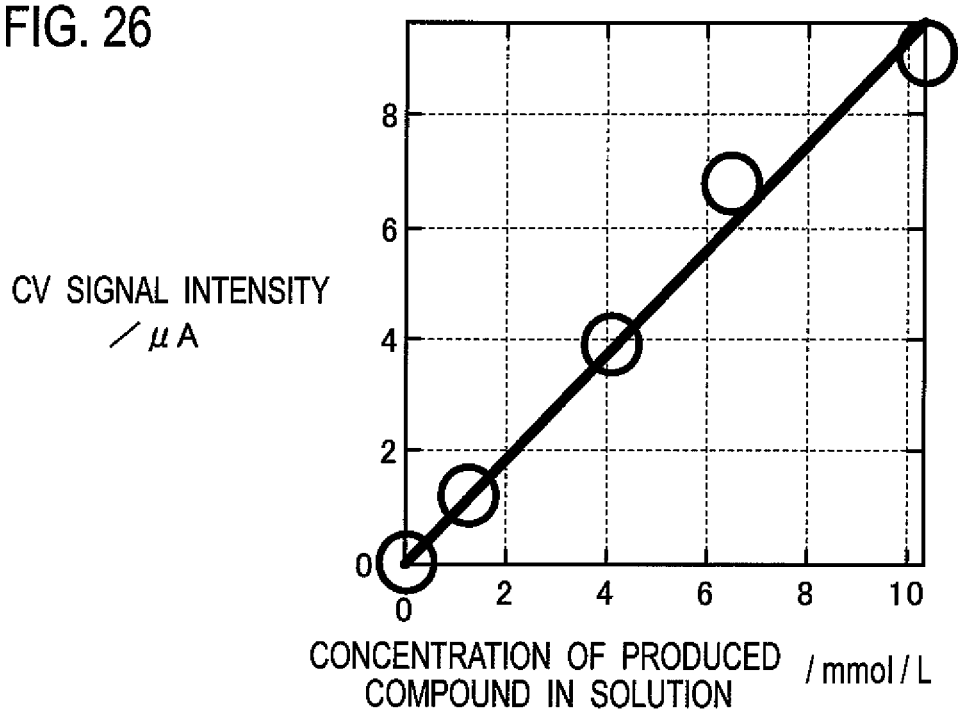
FIG. 26 is a graph illustrating the analysis result of a copper plating solution when the metal ion sensor according to the invention is used.

The observation results proved that the maximum value of the current or the integral value of the current, which was a significant CV signal, was in the range of about +0.7 V to +1.0 V in the copper plating solution that was used, as compared to the current cyclic voltammetry (CV) when an initial make-up bath copper plating solution was analyzed. The maximum value of the current or the integral value of the current, which is a significant CV signal, corresponds to a produced compound included in only the copper plating solution that is used on the spot. The CV measurement and X-ray photoelectron spectroscopy showed that about 36 mM of produced compound was included in the copper plating solution that was used in Example 4. The concentration of the produced compound in the liquid subjected to the above-mentioned process was changed and the intensity of a corresponding CV signal was analyzed. As described in Example 3, the actual data was a value obtained by subtracting the maximum value of the current or the integral value of the current with respect to the voltage obtained from the initial make-up bath copper plating solution from the maximum value of the current or the integral value of the current with respect to the voltage obtained from the copper plating solution that was used. In this case, the maximum value of the current was output as the intensity of the CV signal. As a result, as can be seen from FIG. 26, 2 parameters are proportional to each other. From the above results, according to the invention, it is possible to analyze the concentration of a produced compound on the spot.

However, it is possible to analyze the concentration of a produced compound only from the CV signal of the copper plating solution that is being used, which is included in the produced compound, without subtracting the CV signal of the initial make-up bath copper plating solution as a reference. In addition, the sweep speed of the voltage applied to the working electrode is not limited to 20 mV/sec. Even when the sweep speed is about 5 digits or about −2 digits according to the area of the electrode, it is possible to analyze a produced compound.

Example 6

Next, Example 6 according to the invention relates to a structure capable of analyzing an analysis target without a filtering operation in addition to Example 5. First, in an analysis liquid container with a diameter of about 2.5 cm and a height of about 3 cm, 1 mL of silver nitrate aqueous solution with a concentration of 14 mmol/L was added to 10 mL of plating solution, which was an analysis target. After two minutes, a sensor substrate having a width of 17 mm and a length of 34 mm according to the invention in which the outermost surface of the electrode group arranged on the insulating organic substrate (Polyimide) shown in FIG. 1 was entirely coated with gold or partially coated with carbon was connected to the potentiostat through a connector, and the electrode group of the sensor substrate was immersed in the obtained liquid. Then, the voltage applied to the working electrode in the range of +0.2 V to +2.0 V, which was an electrochemically effective initial state, was swept at a speed of 20 mV/sec, and the dependence of a current with respect to the voltage between the electrodes was observed at a room temperature. In Example 6, the following method was used to obtain the electrochemically effective initial state. That is, first, the sweep speed of the voltage applied to the working electrode was 200 mV/sec, and a sweep cycle from the minimum value to the maximum value and from the maximum value to the minimum value in the set voltage range was performed 10 times. Then, after 5 seconds, similarly, the sweep cycle was performed 5 times, and after 5 seconds, for example, the minimum value +0.2 V in the voltage range was set to the initial state.

Figure 27:
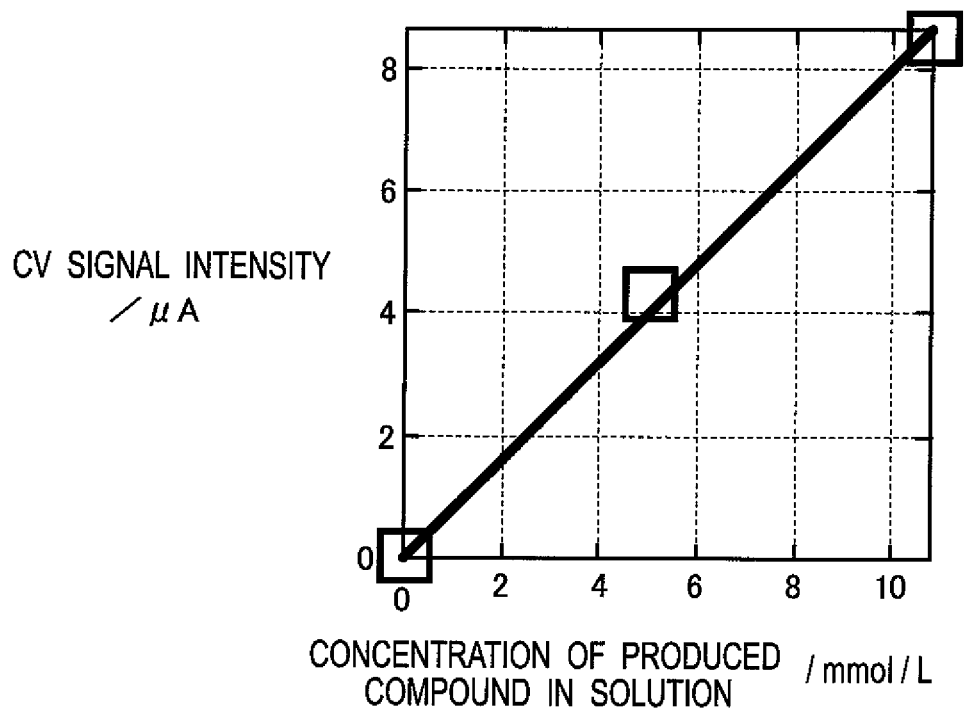
FIG. 27 is a graph illustrating the analysis result of a copper plating solution when the metal ion sensor according to the invention is used and a filtering process is not performed.

The observation results proved that the maximum value of the current or the integral value of the current, which was a significant CV signal, was in the range of about +0.7 V to +1.0 V in the copper plating solution that was used, as compared to the cyclic voltammetry (CV) when an initial make-up bath copper plating solution was analyzed. The maximum value of the current or the integral value of the current, which is a significant CV signal, corresponds to a produced compound included in only the copper plating solution that is used on the spot. The CV measurement and X-ray photoelectron spectroscopy showed that about 36 mM of produced compound was included in the copper plating solution that was used in Example 4. The concentration of the produced compound in the liquid subjected to the above-mentioned process was changed and the intensity of a corresponding CV signal was analyzed. As described in Example 3, the actual data was a value obtained by subtracting the maximum value of the current or the integral value of the current with respect to the voltage obtained from the initial make-up bath copper plating solution from the maximum value of the current or the integral value of the current with respect to the voltage obtained from the copper plating solution that was used. In this case, the maximum value of the current was output as the intensity of the CV signal. As a result, as can be seen from FIG. 27, 2 parameters are proportional to each other. However, there was a little difference between the inclination of a straight line in FIG. 27 and the inclination of a straight line in FIG. 26. It is considered that the difference is caused by the influence of silver salt, the influence of temperature variation, a variation in the sensor substrate, and the analysis time, and the influence of air oxidation.

However, the following changes may be made within the scope of the invention: a change in the volumes of a plating solution and a silver nitrate aqueous solution, which are analysis targets; a change in the size of the sensor substrate; a change in the electrochemically effective initial state for an analysis method; a change in the position or range where the maximum value of current or the integral value of current is observed; and a change in other analysis aspects. The changes are also included in the invention. The sweep speed of the voltage applied to the working electrode is not limited to 20 mV/sec. Even when the sweep speed is about 5 digits or about −2 digits according to the area of the electrode, it is possible to analyze a produced compound.

From, the above-mentioned results, according to the invention, it is possible to analyze a produced compound included in a copper plating solution on the spot by considering the average of an error, such as variation, or the uniformity of analysis conditions.

In Examples 5 and 6, silver nitrate is used as a solution (a chemical species forming a hardly-soluble compound with an analysis preventing material) for making an analysis preventing material hardly soluble, but the invention is not limited thereto. For example, monovalent mercury ions or thallium ions may be used to make the analysis preventing material hardly soluble. In addition, a cationic species forming appropriate hardly-soluble salt, a chemical species having the same function, a polymer analog material, an activated carbon material, or a zeolite analog material may be used to make the analysis preventing material hardly soluble.

Example 7

Figure 28:
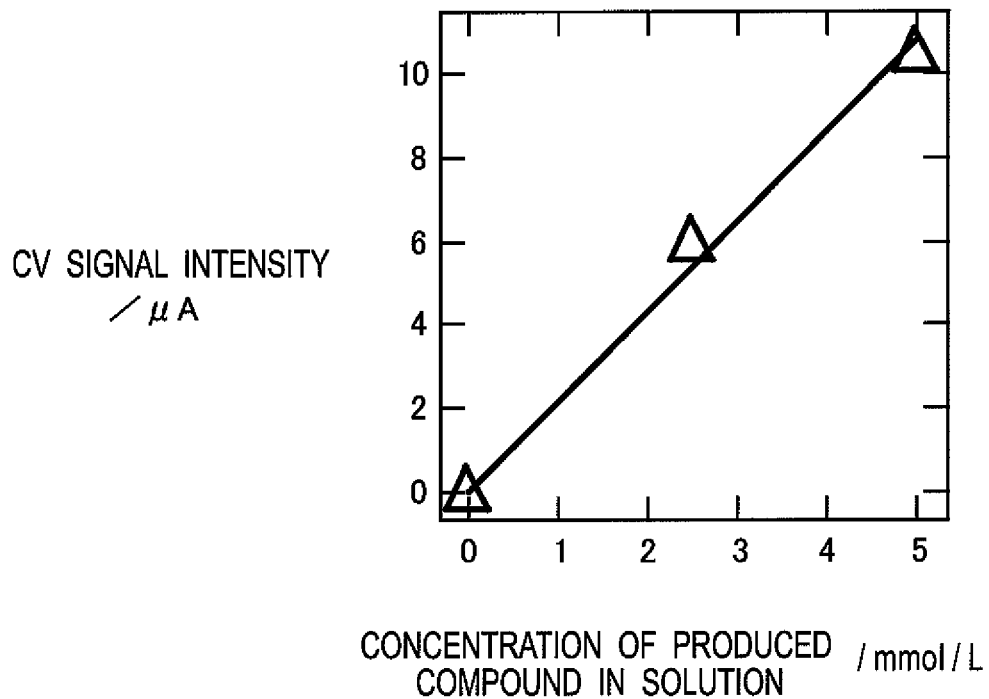
FIG. 28 is a graph illustrating the analysis result of a copper plating solution when a metal ion sensor according to another embodiment of the invention is used and a filtering process is not performed.

Next, Example 7 according to the invention relates to a structure capable of analyzing an analysis target using a sensor with a different shape, without a filtering operation, in addition to Example 5. First, in an analysis liquid container with a diameter of about 2.5 cm and a height of about 3 cm, 1 mL of silver nitrate aqueous solution with a concentration of 14 mmol/L was added to 10 mL of plating solution, which was an analysis target. After two minutes, three gold wires (conductive lines) which had a diameter of 1 mm and were coated with an insulating organic polymer and in which the insulating organic polymer of a portion thereof that was 5 mm from the end was removed were immersed in the above-mentioned liquid, and the exposed portions of the gold wires corresponded to the working electrode, the counter electrode, and the reference electrode. In addition, the insulating organic polymer coated on other portions of the gold wires separated from the exposed portions was removed to form other exposed portions of the gold wires as connection terminals. Then, the connection terminals were connected to the potentiostat so as to correspond to action, opposite, and reference portions. However, the gold wires (conductive lines) might be cut and the cut surfaces might correspond to the working electrode, the counter electrode, and the reference electrode. Then, the voltage applied to the working electrode in the range of +0.2 V to +2.0 V, which was an electrochemically effective initial state, was swept at a speed of 20 mV/sec, and the dependence of a current with respect to the voltage between the electrodes was observed at a room temperature. The observation results proved that the maximum value of the current or the integral value of the current, which was a significant CV signal, was in the range of about +0.7 V to +1.0 V in the copper plating solution that was used, as compared to the cyclic voltammetry (CV) when the initial make-up bath copper plating solution was analyzed. The maximum value of the current or the integral value of the current, which is a significant CV signal, corresponds to a produced compound included in only the copper plating solution that is used on the spot. The CV measurement and X-ray photoelectron spectroscopy showed that about 36 mM of produced compound was included in the copper plating solution that was used in Example 7. The concentration of the produced compound in the liquid subjected to the above-mentioned process was changed and the intensity of a corresponding CV signal was analyzed. As described in Example 3, the actual data was a value obtained by subtracting the maximum value of the current or the integral value of the current with respect to the voltage obtained from the initial make-up bath copper plating solution from the maximum value of the current or the integral value of the current with respect to the voltage obtained from the copper plating solution that was used. In this case, the maximum value of the current was output as the intensity of the CV signal. As a result, 2 parameters were proportional to each other (FIG. 28). From the above-mentioned results, according to the invention, it is possible to analyze a produced compound included in a copper plating solution on the spot.

In Example 7, the insulating organic polymer of the front portions of the gold wires coated with the insulating organic polymer is removed. However, the gold wires may be cut, and the gold sections (cut surfaces) of the gold wires may be exposed. Alternatively, the gold portions may be peeled off by a combination thereof.

The conductive lines used in the invention are not limited to the gold wires, but any lines may be used as long as the surfaces thereof are coated with a material that is not soluble by a liquid or mist including an analyte or a material that is not corroded by gas including the analyte. For example, a platinum line, a platinum iridium line, which will be described below, a copper line plated with gold or platinum, and a line plated with a carbon containing material may be used.

Example 8

Next, Example 8 according to the invention relates to a structure capable of analyzing an analysis target using a sensor with a different shape, without a filtering operation, in addition to Example 5. First, the exposed end of a gold wire which had a diameter 0.25 mm and was coated with an insulator was coated with an insulator. Then, a portion of the insulator corresponding to about 2 mm from a point that was about 7 mm from the end was removed by an appropriate method. In this way, one gold wire whose gold portion was partially exposed was prepared. Then, the exposed ends of platinum/iridium (alloy ratio: 9/1) wires which had a diameter of 0.25 mm and were coated with an insulator were coated with an insulator. Then, a portion of the insulator corresponding to about 2 mm from a point that was about 7 mm from the end was removed by an appropriate method. In this way, two platinum/iridium wires whose plated portions were partially exposed were prepared. The exposed portion of the gold wire corresponded to the working electrode, and the exposed portions of the platinum/iridium wires corresponded to the counter electrode and the reference electrode. In addition, other portions (in Example 8, portions opposite to the exposed portions) of the insulating organic polymer of the gold wires which were separated from the exposed portions were removed to form other exposed portions of the gold wires as connection terminals. The wires were connected to the potentiostat such that the gold wire corresponded to an action portion and the platinum/iridium wires corresponded to an opposite portion and a reference portion. Then, in an analysis liquid container with a diameter of about 2.5 cm and a height of about 3 cm, 1 mL of silver nitrate aqueous solution with a concentration of 14 mmol/L was added to 10 mL of plating solution, which was an analysis target. After two minutes, the metal exposed portions of the three wires were immersed in the liquid, and the voltage applied to the working electrode in the range of +0.2 V to +2.0 V, which was an electrochemically effective initial state, was swept at a speed of 20 mV/sec. Then, the dependence of a current with respect to the voltage between the electrodes was observed at a room temperature. In Example 8, the following method was used to obtain the electrochemically effective initial state. That is, first, the sweep speed of the voltage applied to the working electrode was 200 mV/sec, and a sweep cycle from the minimum value to the maximum value and from the maximum value to the minimum value in the set voltage range was performed 10 times. Then, after 5 seconds, similarly, the sweep cycle was performed 5 times, and after 5 seconds, for example, the minimum value +0.2 V in the voltage range was set to the initial state.

Figure 29:
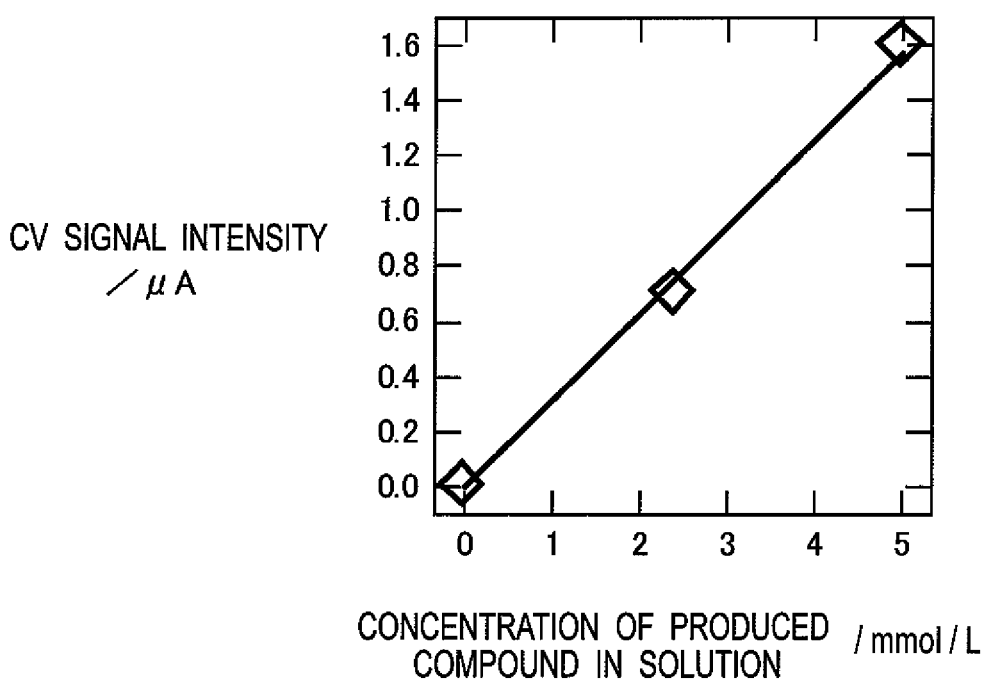
FIG. 29 is a graph illustrating the analysis result of a copper plating solution when a metal ion sensor according to another embodiment of the invention is used and a filtering process is not performed.

The observation results proved that the maximum value of the current or the integral value of the current, which was a significant CV signal, was in the range of about +0.7 V to +1.0 V in the copper plating solution that was used, as compared to the cyclic voltammetry (CV) when the initial make-up bath copper plating solution was analyzed. The maximum value of the current or the integral value of the current, which is a significant CV signal, corresponds to a produced compound included in only the copper plating solution that is used on the spot. The CV measurement and X-ray photoelectron spectroscopy showed that about 36 mM of produced compound was included in the copper plating solution that was used in Example 8. The concentration of the produced compound in the liquid subjected to the above-mentioned process was changed and the intensity of a corresponding CV signal was analyzed. As described in Example 3, the actual data was a value obtained by subtracting the maximum value of the current or the integral value of the current with respect to the voltage obtained from the initial make-up bath copper plating solution from the maximum value of the current or the integral value of the current with respect to the voltage obtained from the copper plating solution that was used. In this case, the maximum value of the current was output as the intensity of the CV signal. As a result, 2 parameters were proportional to each other (FIG. 29). From the above-mentioned results, according to the invention, it is possible to analyze a produced compound included in a copper plating solution on the spot.

However, the following changes may be made within the scope of the invention: a change in the volumes of a plating solution and a silver nitrate aqueous solution, which are analysis targets; a change in the electrochemically effective initial state for an analysis method; a change in the position or range where the maximum value of current or the integral value of current is observed; and a change in other analysis aspects. The changes are also included in the invention. The sweep speed of the voltage applied to the working electrode is not limited to 20 mV/sec. Even when the sweep speed is about 5 digits or about −2 digits according to the area of the electrode, it is possible to analyze a produced compound.

Example 9

Example 9 according to the invention relates to a structure capable of analyzing an analysis target while making an analysis preventing material hardly soluble in stages. That is, in an analysis liquid container with a diameter of about 2.5 cm and a height of about 3 cm, 1 mL of silver nitrate aqueous solution with a concentration of 14 mmol/L was added to 10 mL of plating solution, which was an analysis target. After two minutes, a sensor substrate having a width of 17 mm and a length of 34 mm according to the invention in which the outermost surface of the electrode group arranged on the insulating organic substrate (Polyimide) shown in FIG. 1 was entirely coated with gold or partially coated with carbon was connected to the potentiostat through a connector, and the electrode group of the sensor substrate was immersed in the obtained liquid. Then, the voltage applied to the working electrode in the range of +0.2 V to +2.0 V, which was an electrochemically effective initial state, was swept at a speed of 20 mV/sec, and the dependence of a current with respect to the voltage between the electrodes was observed at a room temperature. The observation results proved that the maximum value of the current or the integral value of the current, which was a significant CV signal, was in the range of about +0.7 V to +1.0 V in the copper plating solution that was used, as compared to the cyclic voltammetry (CV) when the initial make-up bath copper plating solution was analyzed. The maximum value of the current or the integral value of the current, which is a significant CV signal, corresponds to a produced compound included in only the copper plating solution that is used on the spot. Then, 20 mL of sodium hydroxide aqueous solution with a concentration of 2 mol/L was added to the plating solution analyzed in the first stage. A neutralizing process using sodium hydroxide may be omitted. Then, about 5.5 mL of sodium sulfide aqueous solution or sodium polysulfide aqueous solution was added at a concentration of 0.6 mol/L. After two minutes, a black solid was filtered, and a portion of the filtrate was moved to an analysis liquid container with a diameter of about 2.5 cm and a height of about 4 cm. Then, the sensor substrate having a width of 17 mm and a length of 34 mm according to the invention in which the outermost surface of the electrode group arranged on an insulating organic substrate (Polyimide) was entirely coated with gold or partially coated with carbon was connected to the potentiostat through a connector, and the electrode group of the sensor substrate was immersed in the liquid. Then, the voltage applied to the working electrode in the range of +0.2 V to +2.0 V, which was an electrochemically effective initial state, was swept at a speed of 20 mV/see, and the dependence of a current with respect to the voltage between the electrodes was observed at a room temperature. The observation results proved that the maximum value of the current or the integral value of the current, which was a significant CV signal, was in the range of about +0.9 V to +1.6 V in the copper plating solution that was used in the second stage, as compared to the cyclic voltammetry (CV) when the initial make-up bath copper plating solution was analyzed. As such, according to the invention, it is possible to analyze a plurality of produced compounds in the copper plating solution that is being used in stages. However, in Example 9, in the second analysis stage, the black solid is filtered, but analysis may be performed without filtering. The sweep speed of the voltage applied to the working electrode, which is used in this analysis, is not limited to 20 mV/sec. Even when the sweep speed is about 5 digits or about −2 digits according to the area of the electrode, it is possible to analyze a produced compound.

Example 10

According to the invention, when a variation in the current flowing between the electrodes with respect to the voltage become complicated due to a plating preventing chemical species in the copper plating solution to be analyzed, which is being used, a compound produced when copper plating is used, or the interaction among a plurality of chemical species selected from monovalent copper chemical species, it is possible to know the concentration of a chemical species to be analyzed based on the integral value of the current with respect to the voltage with a specific voltage range. It is possible to analyze a plating preventing chemical species or a produced compound included in a copper plating solution on the spot using a value obtained by subtracting the integral value of the current in the voltage range obtained from the initial make-up bath copper plating solution from the integral value of the current in the voltage range obtained from the copper plating solution that is used. First, 1 mL of silver nitrate aqueous solution with a concentration of 14 mmol/L was sequentially added to 10 mL of initial make-up bath copper plating solution and 10 mL of copper plating solution which was used, in two analysis liquid containers with a diameter of about 2.5 cm and a height of about 3 cm. After two minutes, three gold wires (conductive line) which had a diameter of 1 mm and were coated with an insulating organic polymer and in which the insulating organic polymer of portions thereof that were 5 mm from the ends were removed were immersed in the initial make-up bath copper plating solution, and the exposed portions of the gold wires corresponded to the working electrode, the counter electrode, and the reference electrode. In addition, the insulating organic polymer coated on other portions of the gold wires separated from the exposed portions was removed to form other exposed portions of the gold wires as connection terminals. Then, the connection terminals were connected to the potentiostat so as to correspond to action, opposite, and reference portions. However, the gold wires (conductive lines) might be cut and the cut surfaces might correspond to the working electrode, the counter electrode, and the reference electrode. Then, the voltage applied to the working electrode in the range of +0.2 V to +2.0 V, which was an electrochemically effective initial state, was swept at a speed of 20 mV/sec, and the dependence of a current with respect to the voltage between the electrodes was observed at a room temperature. The same measurement was performed on the copper plating solution that was used. The observation results proved that the integral value of the current, which was a significant CV signal, existed at a value of about $1.5 \times 10^{-6}$ VA in the range of about +0.7 V to +0.76 V in the copper plating solution that was used, as compared to the cyclic voltammetry (CV) when the initial make-up bath copper plating solution was analyzed. The integral value of the current, which is a significant CV signal, corresponds to the plating preventing chemical species or the produced compound included in only the copper plating solution that is used. From the above-mentioned results, according to the invention, it is possible to analyze the plating preventing chemical species or the produced compound included in only the copper plating solution on the spot. The sweep speed of the applied voltage is not limited to 20 mV/sec. Even when the sweep speed is about 5 digits or about −2 digits according to the area of the electrode, it is possible to perform analysis. In addition, the position or range where the integral value for an analysis method is objected may be changed and other analysis aspects may be changed within the spirit and scope of the invention. The changes are also included in the invention.

Example 11

The method according to the invention was affected by the temperature, which was checked by the following analysis. That is, the CV of a monovalent copper chemical species in the copper plating solution that was used was analyzed by the sensor substrate according to the invention while changing the temperature of the solution. First, in Example 11, the intensity of the CV signal of the monovalent copper chemical species observed at about +0.82 V was about 10 µA as the maximum current value at a room temperature of 25° C., about 17.5 µA at a temperature of 40° C., and about 55 µA at a temperature of 80° C. That is, as the temperature was increased, the maximum current value was increased. In addition, the base line of an electrochemical current at a voltage of +0.5 V of the working electrode was about 12 µA at a room temperature of 25° C., about 19 µA at a temperature of 40° C., and about 110 µA at a temperature of 80° C. That is, as the temperature was increased, the base line level of the electrochemical current was increased. As described above, it is clear that the method according to the invention is affected by the temperature of the plating solution, which is an analysis target, and it is important to return the temperature of a liquid to be analyzed to the room temperature using a temperature-controlled tank, to make the temperatures of the liquid to be analyzed and a reference solution equal to each other in the temperature-controlled tanks which are disposed in one water tank, to maintain a constant temperature using a kit for a pre-process or an integrated kit, and to consider the correction of the temperature. For example, as shown in FIG. 18, two analysis liquid containers 90 and 92 for analysis are immersed in a temperature-controlled tank 94 filled with room-temperature water for maintaining a constant temperature, and the temperature difference between the initial make-up bath copper plating solution and the copper plating solution that is used in the two analysis liquid containers 90 and 92 is maintained within 10° C. The depths of the analysis liquid containers may vary depending on the conditions. In addition, the rate of temperature change may be used in order to consider the correction of the temperature. In the invention, the rate of temperature change can be theoretically defined by the rate of change of the exponential of a reaction speed from a temperature $T_1$ to a temperature $T_2$ by the Arrhenius equation ($\exp(-E/RT_2)/\exp(-E/RT_1)$; R is an integer and E is reaction activation energy which varies depending on conditions), and it is possible to correct a difference in analysis temperature using the equation. However, in the actual surface reaction, it may be difficult to describe all factors with a simple primary reaction kinetics. Therefore, it is possible to calculate the rate of temperature change according to the invention by giving different equations or correction terms according to the difference between reaction dimensions or the difference between reaction forms, or by measuring the rate of temperature change by experiments. The correction of the temperature using the actually measurement rate of temperature change is performed as follows. First, a variation (rate of temperature change) in the maximum value of the current or the integral value of the current between the electrodes according to the temperature with respect to a variation in the voltage between the electrodes in a reference solution according to the temperature is calculated. This measurement is not changed even though a mixture of an analysis target is changed. Then, a value obtained by multiplying the difference between the temperature of the mixture of the analysis target (in this case, the analysis target is a plating solution) and the temperature of the reference solution (in this case, an initial make-up bath copper plating solution) by the rate of temperature change is added to the maximum value of the current or the integral value of the current between the electrodes with respect to a variation in the voltage between the electrodes in the reference solution, which is measured at the temperature of the reference solution. A value obtained by subtracting the value from the maximum value of the current or the integral value of the current between the electrodes with respect to a variation in the voltage between the electrodes in a liquid to be analyzed is used as the maximum value of the current or the integral value of the current between the electrodes with respect to a variation in the voltage between the electrodes in the analysis target.

Example 12

Figure 30:
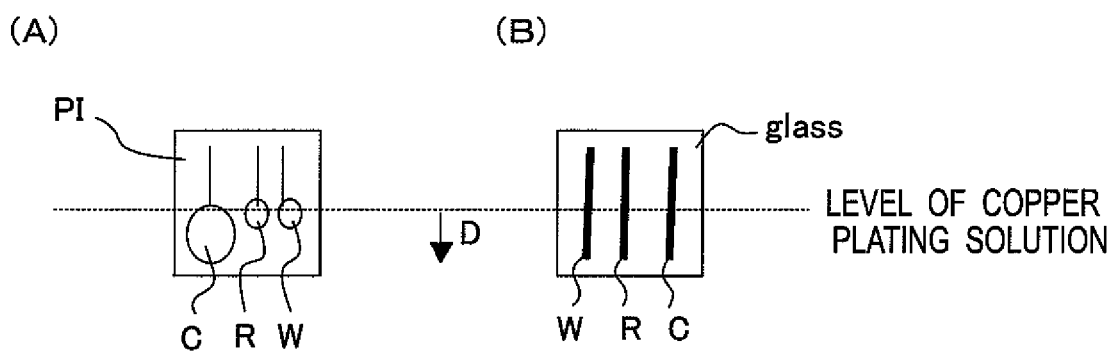
FIG. 30 is a diagram schematically illustrating the state where the sensor according to the invention and the sensor according to the related art are immersed in a copper plating solution and analysis is performed while changing the depth D of immersion.
Figure 31:
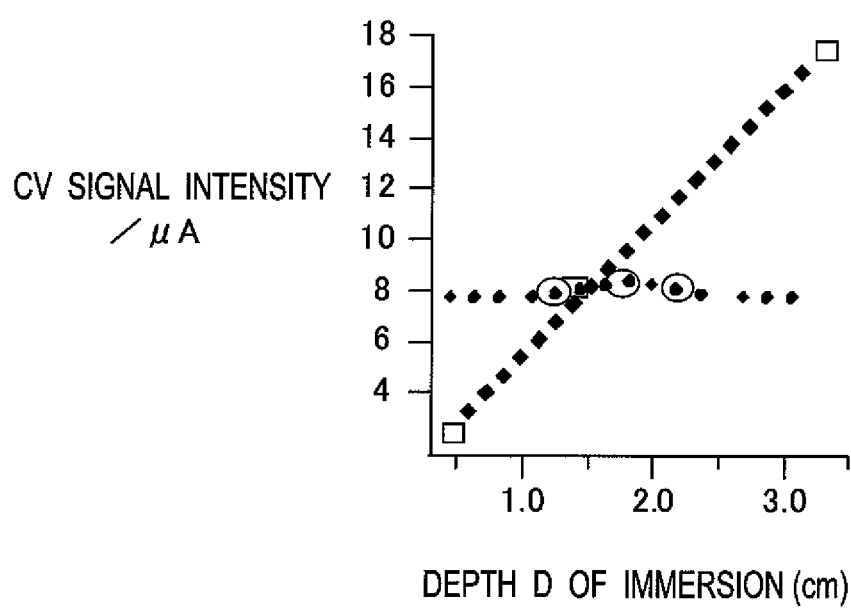
FIG. 31 is a graph illustrating the measurement result of the maximum value of a current, which is a CV signal for the depth D of immersion, when the sensors shown in FIG. 30 are used to perform analysis while changing the depth of immersion.

Example 12 of the invention has an effect of stably performing analysis without immersing a substrate (depth). The effect was verified by the following analysis. A copper plating solution including a monovalent copper chemical species was used as an analysis target. As schematically shown in FIG. 30, a sensor according to the invention in which a coverlay was provided on wiring lines on a polyimide (PI) substrate (FIG. 30(A)) and the sensor according to the related art in which a gold thin film with a width of 3 mm was formed on glass by vapor deposition (FIG. 30(B)) were immersed in the copper plating solution, and analysis was performed while changing the depth (D) of immersion. FIG. 31 is a graph illustrating the analyze results (graph ○) when the sensor according to the invention is used and the analyze results (graph □) when the sensor according to the related art is used. As can be seen from the graph of FIG. 31, the sensor according to the invention stably performs analysis regardless of the depth of immersion, but the analysis result of the sensor according to the related art varies greatly depending on the depth of immersion. In Example 12, the coverlay was used as an insulating portion that was made of an organic material and insulated the wiring lines, but the insulating portion is not limited to the coverlay. Any insulating portion may be used as long as it insulates the wiring lines. In FIG. 30, PI indicates polyimide, glass indicates glass, W indicates the working electrode, R indicates the reference electrode, and C indicates the counter electrode.

Example 13

Figure 32:
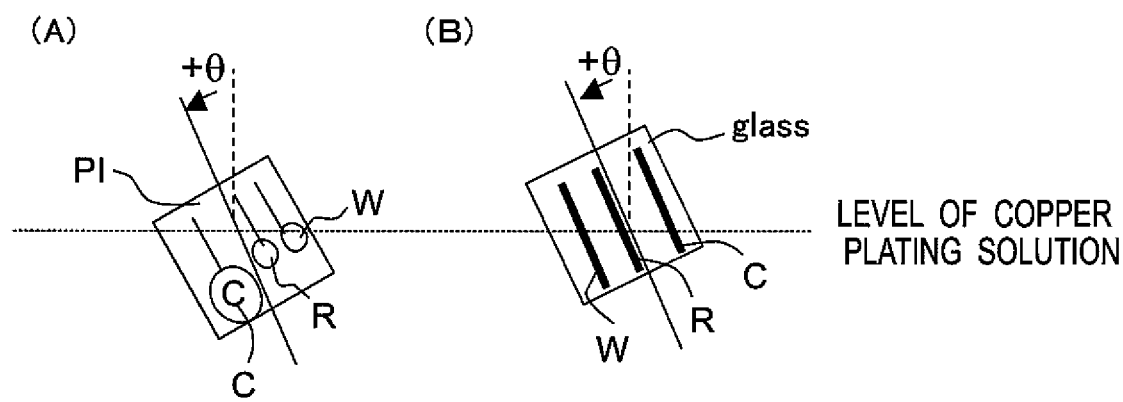
FIG. 32 is a diagram schematically illustrating the state where the sensor according to the invention and the sensor according to the related art are immersed in a copper plating solution and analysis is performed while changing the angle θ of immersion.
Figure 33:
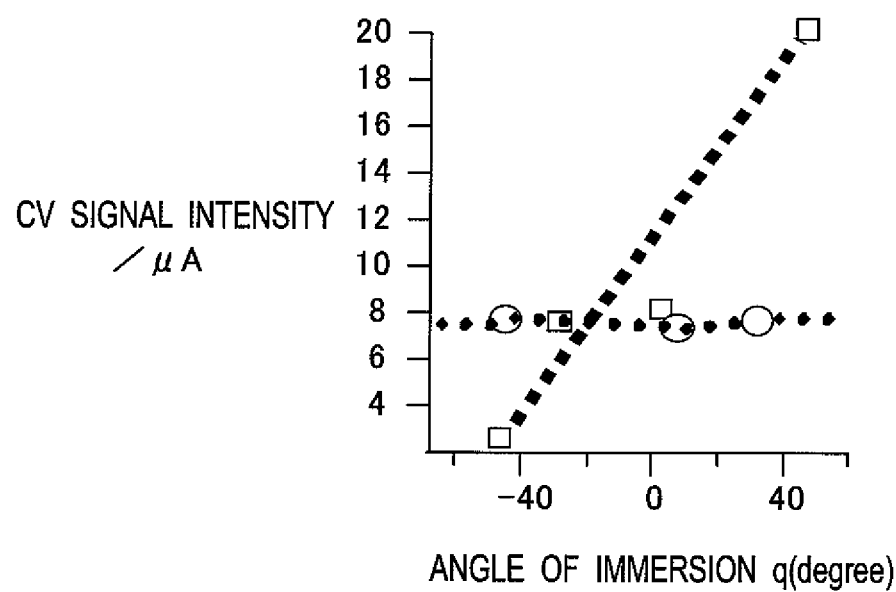
FIG. 33 is a graph illustrating the measurement result of the maximum value of a current, which is a CV signal for the angle θ of immersion, when the sensors shown in FIG. 30 are used to perform analysis while changing the angle of immersion.

Example 13 of the invention has an effect of stably performing analysis without the immersion state of a substrate (inclination). The effect was verified by the following analysis. A copper plating solution including a monovalent copper chemical species was used as an analysis target. As schematically shown in FIG. 32, a sensor according to the invention in which a coverlay was provided on wiring lines on a polyimide (PI) substrate (FIG. 32(A)) and the sensor according to the related art in which gold wires with a width of 3 mm were formed on glass by vapor deposition (FIG. 32(B) were immersed in the copper plating solution, and analysis was performed while changing the angle (θ) of immersion, as shown in FIG. 32. FIG. 33 is a graph illustrating the analyze results (graph ○) when the sensor according to the invention is used and the analyze results (graph □) when the sensor according to the related art is used. As can be seen from the graph of FIG. 33, the sensor according to the invention stably performs analysis regardless of the angle of immersion, but the analysis result of the sensor according to the related art in which the gold wires with a width of 3 mm are formed by vapor deposition varies greatly depending on the angle of immersion. In FIG. 32, PI indicates polyimide, glass indicates glass, W indicates the working electrode, R indicates the reference electrode, and C indicates the counter electrode.

Example 14

As described above, the exposure of the gold-plated portion that is not covered with the carbon including layer is likely to prevent analysis. For example, as described in Example 13, similar to when the area of the electrode varies depending on the angle of immersion, the gold plated portion that is not covered with the carbon including layer causes a variation in the area of the electrode between the sensor substrates. In the recession structure of the coverlay, it is preferable that the wiring line extend from the electrode in the thickness direction of the substrate, that is, the vertical direction, not in the plane direction of the substrate. According to Example 14 of the invention, in a method of drawing the wiring line in the plane direction, it is also possible to ensure reproducibility between the substrates by covering the gold-plated portion with the carbon including layer, and it is possible to achieve durability capable of repeatedly performing measurement with the same substrate. In Example 14, the effects were verified as follows.

Figure 34:
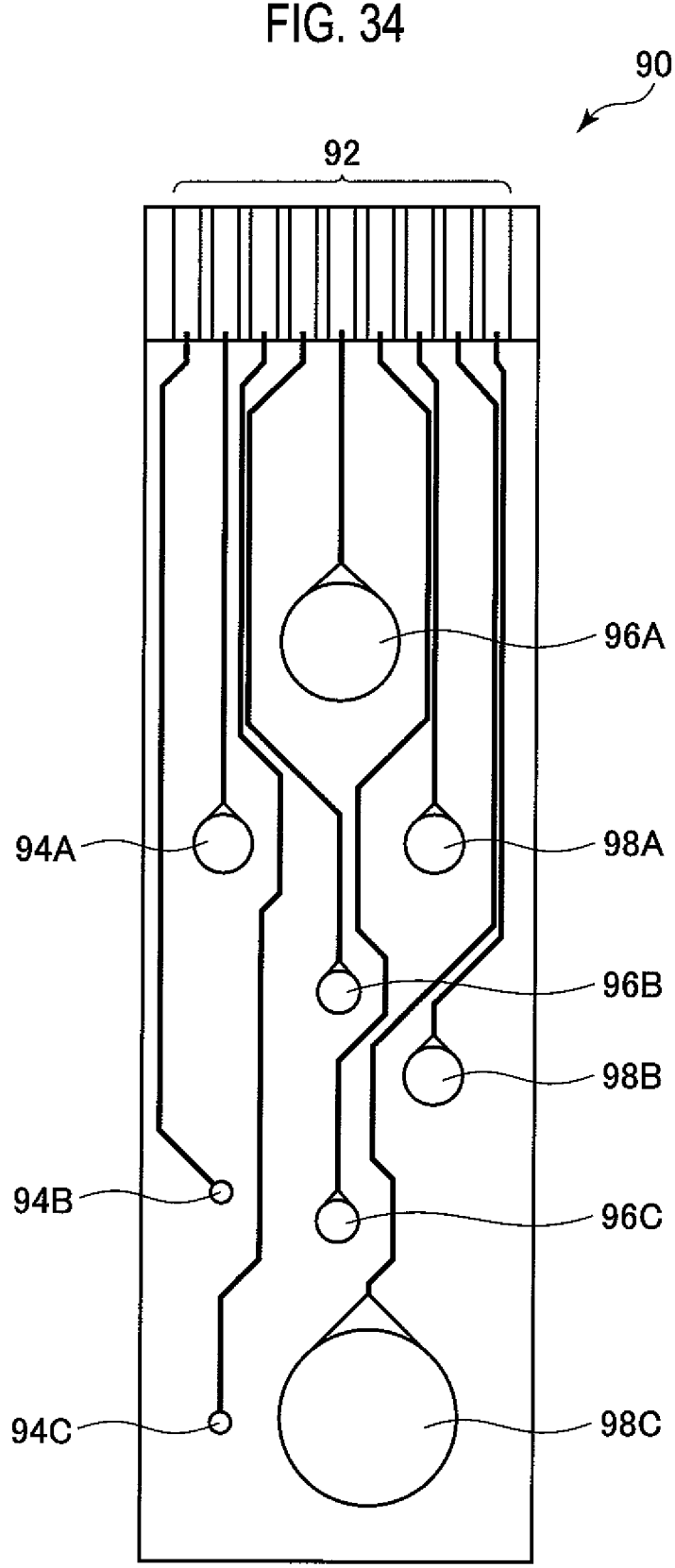
FIG. 34 is a top view illustrating a sensor substrate used in Example 14.
Figure 35:
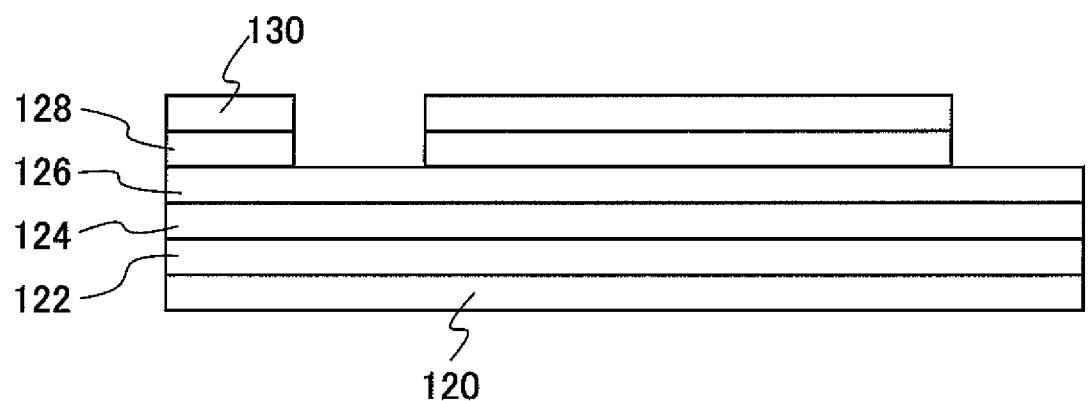
FIG. 35 is a diagram schematically illustrating the cross section of the sensor substrate shown in Example 14.

FIG. 34 is a plan view illustrating a sensor substrate including nine electrodes. The sensor substrate includes three sets of a counter electrode (C), a reference electrode (R), and a working electrode (W). Specifically, a sensor substrate 90 has nine measuring terminals 92 at the edge thereof, and measuring electrodes 94A, 94B, 94C, 96A, 96B, 96C, 98A, 98B, and 98C are connected to the measuring terminals 92 through the wiring lines. Any three sets of measuring electrodes are used as the counter electrode (C), the reference electrode (R), and the working electrode (W). As a connector, a 1 mm pitch connector FH12-9S-1SH (product number) manufactured by Hirose Electric Co., Ltd. was used, and the outer width of the substrate and the arrangement of the terminals were designed according to the connectors. A polyimide film with a copper foil was used as the substrate. In this case, the thickness of a terminal portion fitted to the connector in the substrate thickness including the thickness of the terminal is 0.3±0.05 mm. A sensor substrate having a cross-sectional structure shown in FIG. 35 was designed and manufactured based on the dimensions of the connector. That is, as shown in FIG. 35, the manufactured sensor substrate has a structure in which a base polyimide 124 is adhered to a reinforcing plate polyimide 120 with a thermosetting adhesive layer 122 interposed therebetween, a copper foil 126 is provided on the base polyimide 124, and a coverlay film (polyimide film) 130 is adhered to the copper foil 126 with an adhesive layer 128 interposed therebetween. The thickness of the reinforcing plate polyimide 120 is 180 μm, the thickness of the thermosetting adhesive layer 122 is 50 μm, the thickness of the base polyimide 124 is 25 μm, the thickness of the copper foil 126 is 35 μm, the thickness of the adhesive layer 128 is 25 μm, and the thickness of the coverlay film (polyimide film) 130 is 25 μm.

The coverlay was formed by integrating a polyimide film with an adhesive. The adhesive was heated in advance to be hardened, thereby controlling flowability or expanding the clearance. In this way, the contamination of the electrode by the adhesive was prevented and a variation in the area of the electrode due to the flow of the adhesive did not occur. In addition, the coverlay was adhered to a hatched region in FIG. 36.

The positional deviation between the electrode and an opening is large in the plane, which may cause a large variation in wiring lines in the opening. In Example 14, after the coverlay was adhered, any of the following preprocesses was performed before carbon paste was applied: the radiation of oxygen plasma (300 W and 60 seconds); the radiation of UV and ozone (the amount of oxygen introduced is 0.1 mL/min) for 50 minutes; and immersion in methanol for 3 minutes (application of US) and immersion in ultrapure water for 3 minutes (application of US). It was possible to ensure adhesion stability when an ink jet method was used to apply and form carbon paste by appropriately selecting the pre-process.

Then, as the working electrode and the reference electrode, carbon paste manufactured by HITACHI CHEMICAL CO., LTD was applied by an ink jet method to form square electrodes with a side length of 2.9 mm (an opening in the electrode: Φ2.5). In addition, similarly, as the counter electrode, carbon paste was applied to form a square electrode with a side length of 3.9 mm (an opening in the electrode: Φ3.5). The carbon paste was dried by a heater having a temperature adjusting function at a temperature of 160° C. for one hour. Then, only the working electrode portion and the counter electrode portion were exposed and gold was deposited with a thickness of 2000 Å using the terminal portion fitted to the connector and the reference electrode as a mask. The vapor deposition speed is preferably 1.8 Å/sec. When control is unavailable, it is preferable that the vapor deposition speed be in the range of 0.1 Å/sec to 10 Å/sec. The substrate manufactured in this way makes it possible to ensure durability capable of repeatedly performing measurement with the same substrate and reproducibility between the substrates.

Figure 37:
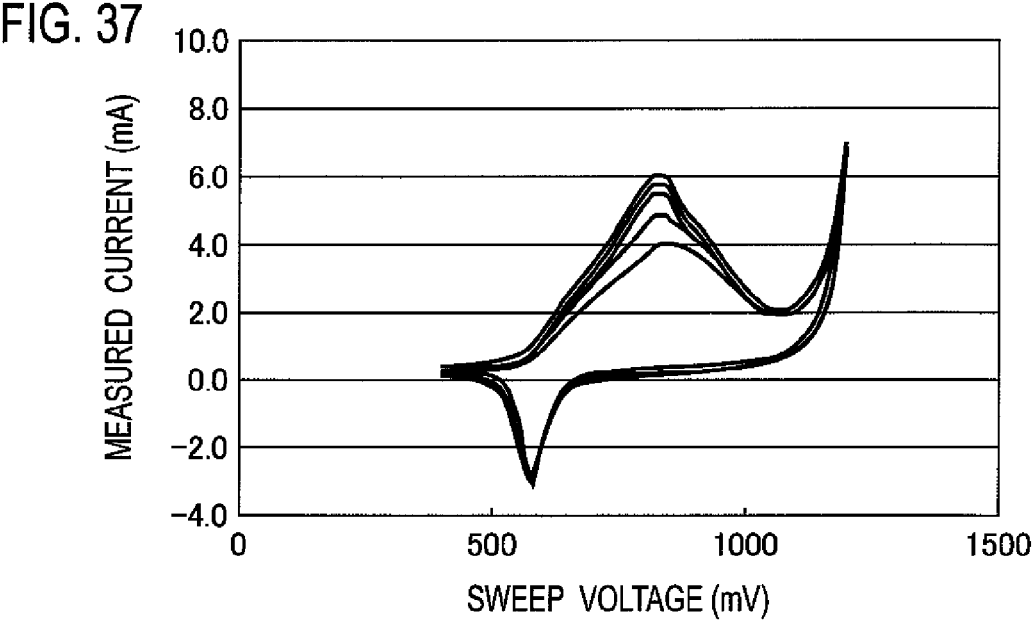
FIG. 37 is a graph illustrating the analysis result of a filled copper plating solution by six sensors according to Example 14.

Then, the following operation was performed to verify that the reproducibility between the substrates was ensured. Six substrates were manufactured by the above-mentioned method, and the amount of solution used for filled copper plating was measured by each substrate. As could be seen from FIG. 37, in the reaction of the electrode with monovalent copper, the base current was stabilized, and a variation in the potential position of a monovalent copper peak was removed. Six graphs shown in FIG. 37 show the measurement results of the six substrates.

However, there is about ±20% of variation in the current value between the substrates from the average value. This tendency also appears in an initial make-up bath. That is, this is because the peak of a monovalent copper chemical species overlaps the oxidation reaction of gold. In this case, R3, C3, and W3 shown in FIG. 36 were used as the reference electrode, the counter electrode, and the working electrode.

Figure 38:
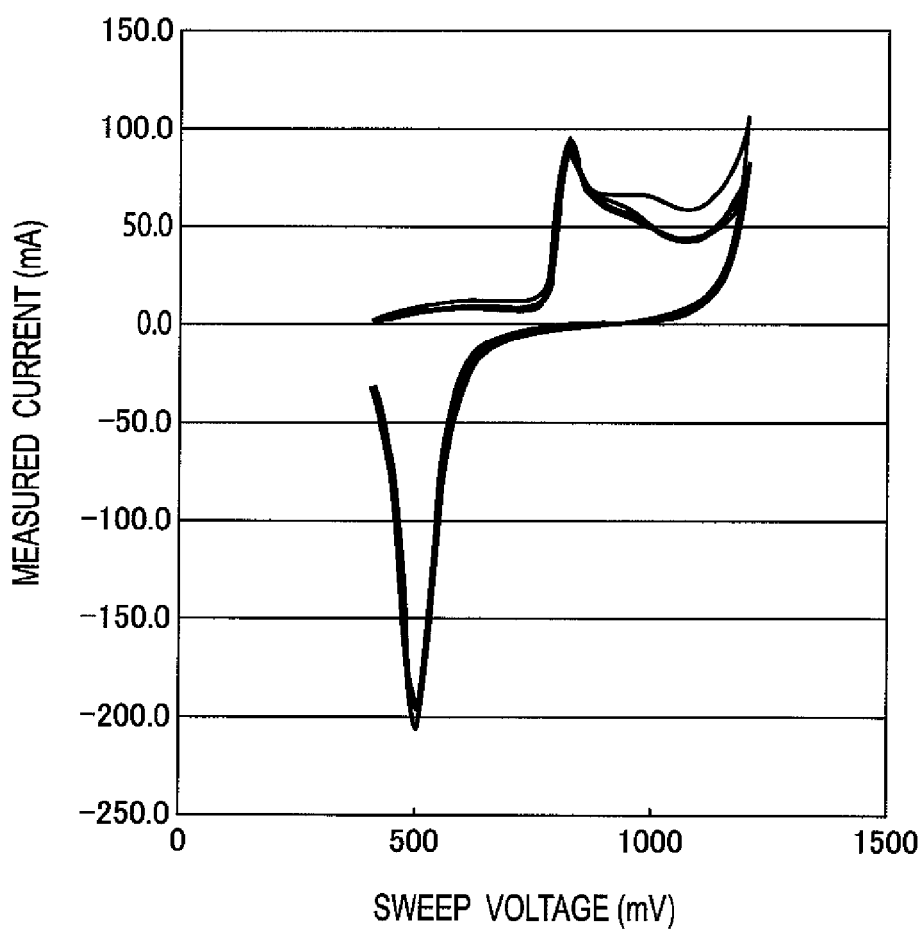
FIG. 38 is a graph illustrating the analysis result of an initial make-up bath solution by six sensors according to Example 14.

Then, carbon paste was applied to the working electrode and the counter electrode of each of the six substrates, and gold was deposited thereon by vapor deposition. In this case, R3, C3, and C2 shown in FIG. 36 were used as the reference electrode, the counter electrode, and the working electrode. That is, the reference electrode was arranged between the counter electrode and the working electrode. Then, as shown in the graph of FIG. 38, the measurement result of an initial make-up bath solution proved that a variation in the current value was removed. Similar to FIG. 37, six graphs shown in FIG. 38 show the measurement results of the six substrates. It was possible to increase the detected current by increasing the size of the working electrode and arranging the reference electrode so as to be opposite to the working electrode. In addition, it was possible to reduce the variation to ±7% or less.

Figure 39:
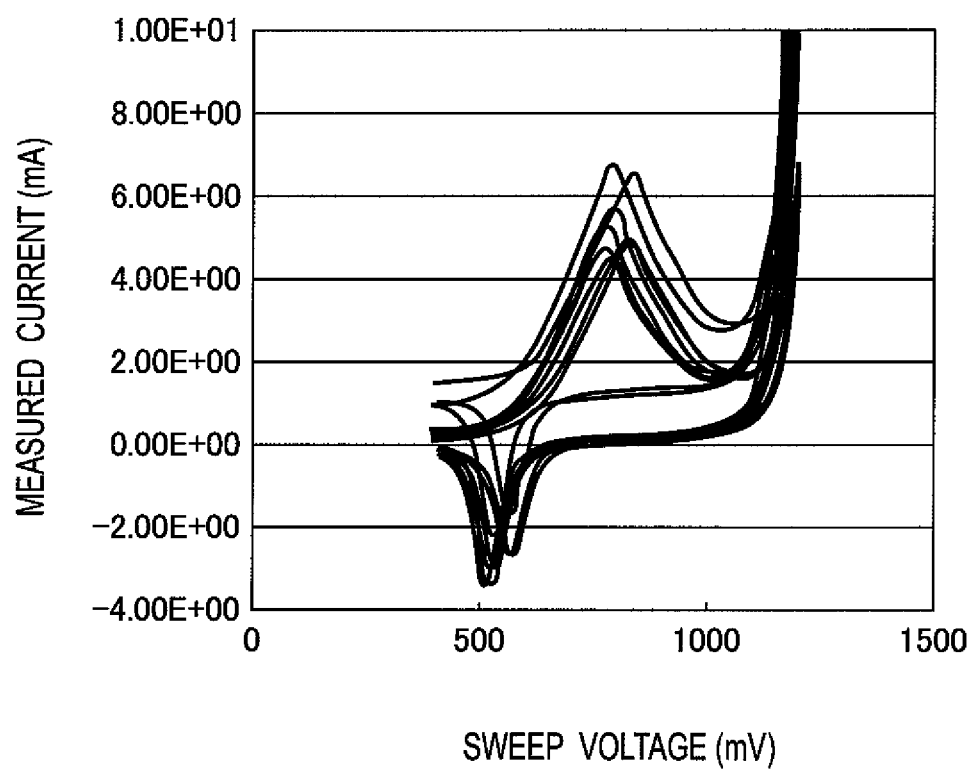
FIG. 39 is a graph illustrating the analysis result of a filled copper plating solution by ten sensors without the structure according to the invention.

All the electrodes were formed by directly plating copper with gold, unlike the structure according to the invention, and the amount of solution used for filled copper plating was measured. In this case, the electrode reacted with monovalent copper, as shown in FIG. 39. As a result, there was a variation in the base current, the potential position of a monovalent copper peak, or the current value.

It is considered that the instability of the base current and the variation in the potential position of the monovalent copper peak and the current value are caused by an alloy of gold and copper on the outer layer and the formation of an oxide on the surface, according to the cross-sectional observation of the electrode portion by FIB, an electron microscope, or EDX analysis. The detailed examination results proved that chrome or nickel as well as gold could be formed as an underlying layer on the carbon including layer, and an alloy of gold and copper could be formed. In addition, it was possible to closely deposit titanium or titanium oxide using vapor deposition. In this case, in the gold-copper alloy, the ratio of the weight of gold to the weight of copper was 9.25:1.

It was possible to improve the surface roughness of the electrode during etching by covering the electrode formed by etching with the carbon including layer. It was possible to reduce the centerline average roughness from 1500 to 2000 Å to 50 Å by repeatedly performing application and drying three times or more, and control the centerline average roughness to an atomic flat level that is equal to the wall interface of mica. In this way, it is possible to improve the formability of a self-assembled organic monolayer after gold is deposited by vapor deposition.

An example using a polyimide film has been described above. Another example in which a liquid crystal polymer is used as a base material in the pattern shown in FIG. 34 will be described below.

A liquid crystal polymer (manufactured by JAPAN GORE-TEX INC.) BIAC-C was prepared as a base material, and a copper foil with a thickness of 12 μm was directly attached to a substrate with a thickness of 300 μm and then patterned by etching. An adhesive layer KS-7003 manufactured by HITACHI CHEMICAL CO., LTD. (25 μm) was adhered to a coverlay with a thickness of 125 μm by press bonding at a temperature of 110° C., and boring plates having holes with clearances of +1.0 mm and +0.5 mm (500 μm and 250 μm on one side) with respect to the diameter of the electrode were prepared. The former that was disposed on the lower side was temporarily adhered to the latter that was disposed on the upper side by a pin-lamination method and vacuum pressing was performed at a temperature of 160° C. and at a pressure of 2M Pa.

The recession structure was formed in the coverlay by the above-mentioned process, and the same examination was performed. However, in the ink jet method, since the extending wiring line in the recession structure was not covered, an unstable oxidation reaction occurred in the gold-copper alloy. That is, it was important to draw the extending wiring line immediately below the electrode. However, in this case, oxygen plasma processing was performed with an output of 300 W for one minute, or UV and ozone processing was performed for 50 minutes to improve wettability, and a predetermined amount of material (0.004 μL in a φ1.5 electrode) was applied by a micropipette technique to cover the wiring line in the recession structure. However, in this case, production efficiency was reduced. When the oxygen plasma processing and the UV and ozone processing were performed, the wettability of a test solution as well as the wettability of a base material was improved. When the liquid crystal polymer was used, a mysterious phenomenon in which a current signal was not output even though the voltage was swept occurred. In this case, when the surface was wetted by pure water before it was immersed in the test solution, a signal was output. Therefore, the inventor considered that the phenomenon occurred because surface energy was low and water-repellency was high. After the process, it was possible to measure the output of the current signal even though the surface was directly immersed in the test solution. As described above, after the wiring line below the recession structure was covered, it was possible to form the carbon including layer on the electrode and the coverlay so as to be insulated from the surface of the coverlay using an ink jet method.

Figure 40:
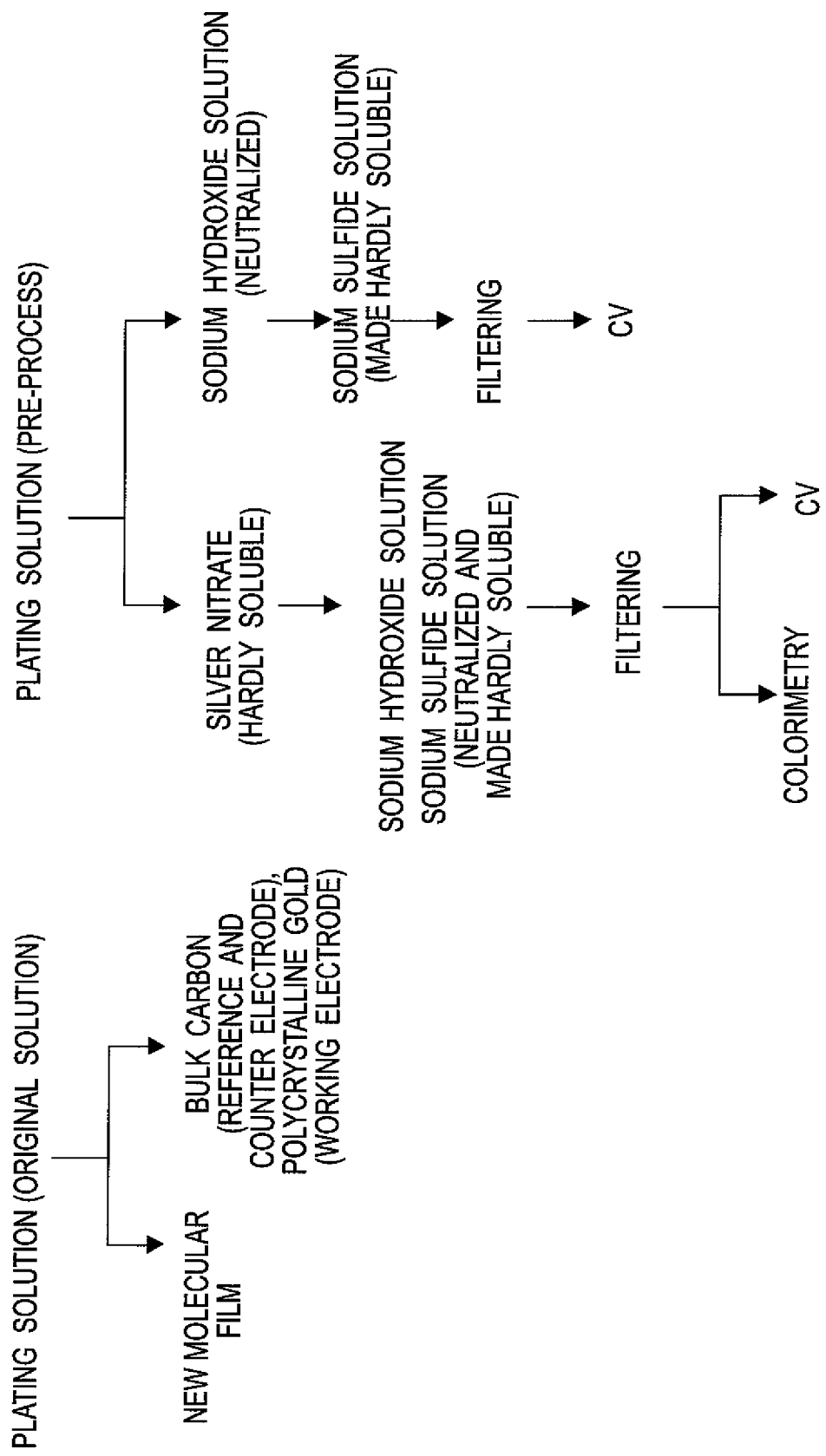
FIG. 40 is a diagram illustrating an analysis sequence according to the invention.

According to the invention, it was possible to construct an analysis sequence shown in FIG. 40. The invention can be applied to metal ions, such as cadmium, or a related chemical species as well as monovalent copper. The invention can be used to analyze, for example, an etchant, tap water, soil, and the contamination of a food and a plant, such as a rice plant or vegetable, from soil, in addition to the plating solution.

The invention claimed is:

1. A sensor comprising:
   first and second conductive electrodes;
   first and second conductive wiring lines that are respectively connected to the first and second conductive electrodes,
   wherein the first and second wiring lines are connected to corresponding connection terminals;
   an insulating portion that insulates the first wiring line from the second wiring line and insulates the first and second wiring lines from a liquid including an analyte,
   wherein the insulating portion is made of an organic material, and
   at least the surfaces of portions of the first and second electrodes that come into contact with the liquid including the analyte are made of a material that is insoluble by the liquid including the analyte;
   an insulating substrate that is made of an organic material;
   at east one electrode group that includes the first and second electrodes and is arranged on the insulating substrate;
   at least one connection wiring line group that is electrical connected to the at least one electrode group and has at least one layer including the first and second wiring lines;
   at least one connection terminal group that is electrically connected to the at least one connection wiring line group; and
   at least a coverlay that is provided on the insulating substrate, has openings through which the at least one electrode group is exposed to the outside, and covers the at least one connection wiring line group,
   wherein at least the coverlay and the insulating substrate form the insulating portion that insulates the at least one connection wiring line group and insulates the conductive wiring lines from the liquid including the analyte.

2. The sensor according to claim 1, further comprising:
   a third electrode on the insulating substrate that supplies at least a portion of the potential thereof to the first electrode or the second electrode at the same polarity or different polarities; and
   a third wiring line that is connected to the third electrode,
   wherein at least the surface of a portion of the third electrode that comes into contact with the liquid including the analyte is made of a material that is insoluble by the liquid including the analyte.

3. The sensor according to claim 2, wherein
   at least the coverlay that is provided on the insulating substrate, has the openings through which the third electrode is exposed to the outside, and covers the third wiring line,
   wherein at least the coverlay and the insulating substrate form the insulating portion that insulates the third connection wiring line from the liquid including the analyte.

4. The sensor according to claim 3,
   wherein each of the openings of the coverlay is provided so as to be arranged inside each electrode including the third electrode.

5. The sensor according to claim 4, further comprising:
   at least a carbon including layer that is provided on the insulating substrate,
   wherein the carbon including layer is formed on the surface of the coverlay surface and at least a portion of the surface of each electrode disposed in the openings.

6. The sensor according to claim 5,
   wherein an opening of the openings of the coverlay is formed such that the diameter thereof is increased from an upper surface to a lower surface.

7. The sensor according to claim 5,
   wherein the coverlay is formed such that the area of an opening of the openings in an upper surface is less than the area of the opening in a lower surface.

8. The sensor according to claim 5,
   wherein the coverlay includes at least two layers, that is, a coverlay film and an adhesive layer, and
   the edge of an opening in the adhesive layer and the edge of an opening of the coverlay film are arranged at the same position, or the edge of the opening in the adhesive layer is arranged outside the edge of the opening of the coverlay film.

9. The sensor according to claim 4,
   wherein an opening of the openings of the coverlay is formed such that the diameter thereof is increased from an upper surface to a lower surface.

10. The sensor according to claim 4,
    wherein the coverlay is formed such that the area of an opening of the openings in an upper surface is less than the area of the opening in a lower surface.

11. The sensor according to claim 4,
    wherein the coverlay includes at least two layers, that is, a coverlay film and an adhesive layer, and
    the edge of an opening in the adhesive layer and the edge of an opening of the coverlay film are arranged at the same position, or the edge of the opening in the adhesive layer is arranged outside the edge of the opening of the coverlay film.

12. The sensor according to claim 3,
    wherein each of the openings of the coverlay is provided so as to be arranged outside each electrode including the third electrode.

13. The sensor according to claim 12, further comprising:
    at least a carbon including layer that is provided on the insulating substrate, wherein the carbon including layer is formed on the surface of the coverlay surface and at least a portion of the surface of each electrode disposed in the openings.

14. The sensor according to claim 13, wherein an opening of the openings of the coverlay is formed such that the diameter thereof is increased from an upper surface to a lower surface.

15. The sensor according to claim 13, wherein the coverlay is formed such that the area of an opening of the openings in an upper surface is less than the area of the opening in a lower surface.

16. The sensor according to claim 13, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

17. The sensor according to claim 12, wherein an opening of the openings of the coverlay is formed such that the diameter thereof is increased from an upper surface to a lower surface.

18. The sensor according to claim 12, wherein the coverlay is formed such that the area of an opening of the openings in an upper surface is less than the area of the opening in a lower surface.

19. The sensor according to claim 12, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

20. The sensor according to claim 3, wherein an opening of the openings of the coverlay is formed such that the diameter thereof is increased from an upper surface to a lower surface.

21. The sensor according to claim 1, wherein each of the openings of the coverlay is provided so as to be arranged inside each electrode of the at least one electrode group.

22. The sensor according to claim 21, further comprising: at least a carbon including layer that is provided on the insulating substrate, wherein the carbon including layer is formed on the surface of the coverlay surface and at least a portion of the surface of each electrode disposed in the openings.

23. The sensor according to claim 22, wherein an opening of the openings of the coverlay is formed such that the diameter thereof is increased from an upper surface to a lower surface.

24. The sensor according to claim 22, wherein the coverlay is formed such that the area of an opening of the openings in an upper surface is less than the area of the opening in a lower surface.

25. The sensor according to claim 22, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

26. The sensor according to claim 21, wherein the coverlay is formed such that the area of an opening of the openings in an upper surface is less than the area of the opening in a lower surface.

27. The sensor according to claim 21, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

28. The sensor according to claim 21, wherein an opening of the openings of the coverlay is formed such that the diameter thereof is increased from an upper surface to a lower surface.

29. The sensor according to claim 1, wherein each of the openings of the coverlay is provided so as to be arranged outside each electrode of the at least one electrode group that is exposed through the openings.

30. The sensor according to claim 29, further comprising: at least a carbon including layer that is provided on the insulating substrate, wherein the carbon including layer is formed on the surface of the coverlay surface and at least a portion of the surface of each electrode disposed in the openings.

31. The sensor according to claim 30, wherein an opening of the openings of the coverlay is formed such that the diameter thereof is increased from an upper surface to a lower surface.

32. The sensor according to claim 30, wherein the coverlay is formed such that the area of an opening of the openings in an upper surface is less than the area of the opening in a lower surface.

33. The sensor according to claim 30, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

34. The sensor according to claim 29, wherein an opening of the openings of the coverlay is formed such that the diameter thereof is increased from an upper surface to a lower surface.

35. The sensor according to claim 29, wherein the coverlay is formed such that the area of an opening of the openings in an upper surface is less than the area of the opening in a lower surface.

36. The sensor according to claim 29, wherein the coverlay includes at least two layers, that is, a coverlay film and an adhesive layer, and the edge of an opening in the adhesive layer and the edge of an opening of the coverlay film are arranged at the same position, or the edge of the opening in the adhesive layer is arranged outside the edge of the opening of the coverlay film.

37. The sensor according to claim 1, wherein an opening of the openings of the coverlay is formed such that the diameter thereof is increased from an upper surface to a lower surface.

* * * * *